United States Patent
Ueda

(10) Patent No.: US 9,617,324 B2
(45) Date of Patent: Apr. 11, 2017

(54) AMELIORATING AGENT FOR BLOOD-BRAIN BARRIER DYSFUNCTION

(71) Applicants:Nagasaki University, Bunkyo-machi, Nagasaki-shi, Nagasaki (JP); Shin Nippon Biomedical Laboratories, Ltd., Miyanoura-cho, Kagoshima-shi, Kagoshima (JP)

(72) Inventor: Hiroshi Ueda, Nagasaki (JP)

(73) Assignee: NAGASAKI UNIVERSITY, Nagasaki (JP)

( * ) Notice: Subject to any disclaimer, the term of this patent is extended or adjusted under 35 U.S.C. 154(b) by 0 days.

(21) Appl. No.: 14/378,323

(22) PCT Filed: Feb. 13, 2013

(86) PCT No.: PCT/JP2013/053436
§ 371 (c)(1),
(2) Date: Sep. 11, 2014

(87) PCT Pub. No.: WO2013/122116
PCT Pub. Date: Aug. 22, 2013

(65) Prior Publication Data
US 2015/0166626 A1  Jun. 18, 2015

(30) Foreign Application Priority Data

Feb. 13, 2012 (JP) ................................ 2012-028918
Nov. 30, 2012 (JP) ................................ 2012-262007

(51) Int. Cl.
*C07K 14/575* (2006.01)
*A61K 38/08* (2006.01)
*A61K 45/06* (2006.01)
*A61K 38/00* (2006.01)

(52) U.S. Cl.
CPC ........ *C07K 14/57581* (2013.01); *A61K 38/00* (2013.01); *A61K 38/08* (2013.01); *A61K 45/06* (2013.01)

(58) Field of Classification Search
None
See application file for complete search history.

(56) References Cited

U.S. PATENT DOCUMENTS

2003/0138926 A1* 7/2003 Prayaga ................. C07K 14/47
435/183

FOREIGN PATENT DOCUMENTS

JP  WO2004064861 A1  8/2004
JP  WO2011019023 A1  2/2011

OTHER PUBLICATIONS

Zhang et al. ("Breakdown of the gut barrier in patients with multiple organ dysfunction syndrome is attenuated by continuous blood purification: effects on tight junction structural proteins"; Int J Artif Organs, Jan. 2010;33(1):5-14).*
Zampieri et al. (Clinics 2011; 66(10);1825-1831).*
The Merck Manual (http://www.merckmanuals.com/professional/neurologic-disorders/stroke-cva/intracerebral-hemorrhage accessed Sep. 19, 2016).*
WebMD states (http://www.webmd.com/brain/brain-hemorrhage-bleeding-causes-symptoms-treatments#2 accessed Sep. 19, 2016).*
International Search Report of international patent application No. PCT/JP2013/053436 completed on Mar. 27, 2013 and mailed Apr. 9, 2013 (4 pages).
Hiroshi Ueda, "No o Mamoru Tanpakushitsu Prothymosin ex Atarashii Nosocchu Chiryoyaku no Kaihatsu ni Mukete" , 2008, Medical Bio, vo1.5, No. 2, pp. 83 to 89.
Yomiuri shinbun online, Oct. 25, 2005, http://www.yomiuri.co.jp/iryou/medi/saisin/20051025ik14. htm.
Journal of Cell Biology (2007), 176, 853-862.
Cell Death and Differentiation (2007), 14, 1839-1842.
Cell Death and Differentiation (2009), 16, 349-358.

* cited by examiner

*Primary Examiner* — James H Alstrum Acevedo
*Assistant Examiner* — Tara Martinez
(74) *Attorney, Agent, or Firm* — Pyprus pte Ltd

(57) ABSTRACT

To provide a peptide which can be produced and processed more readily compared with prothymosin α , which is conventionally known, or a peptide thereof and has an activity at a level equivalent to or higher than that of prothymosin α or a peptide thereof. The present invention provides an ameliorating agent for blood-organ barrier dysfunction, a therapeutic agent for diseases associated with blood-organ barrier dysfunction or ischemic diseases or a nerve cell death inhibitor, each comprising, as an active ingredient, a peptide comprising the amino acid sequence represented by SEQ ID NO: 1 or a peptide having substantially the same function as that of the aforementioned peptide.

6 Claims, 30 Drawing Sheets

Fig. 1A

```
                                              10         20         30         40         50         60
Seq.No.7: PROTHYMOSIN DERIVED FROM HUMAN  MSDAAVDTSS EITTKDLKEK KEVVEEAENG RDAPANGNA- NEENGEQEAD NEVDEEEEEG
Seq.No.9: PROTHYMOSIN DERIVED FROM RAT    MSDAAVDTSS EITTKDLKEK KEVVEEAENG RDAPANGNAQ NEENGEQEAD NEVDEEEEG
Seq.No.8: PROTHYMOSIN DERIVED FROM MOUSE  MSDAAVDTSS EITTKDLKEK KEVVEEAENG RDAPANGNAQ NEENGEQEAD NEVDEEEEEG
                              THYMOSIN            SDAAVDTSS EITTKDLKEK KEVVEEAEN 70         80         90        100        110
Seq.No.7: PROTHYMOSIN DERIVED FROM HUMAN  GEEE------G DGEEEDGDED EGAESATGKR AEDDEDDDV DTKQK-TDE DD
Seq.No.9: PROTHYMOSIN DERIVED FROM RAT    GEEEEEEEEG DGEEEDGDED EEAEAPTGKR VAEDDEDDDV ETKKQKKTDE DD
Seq.No.8: PROTHYMOSIN DERIVED FROM MOUSE  GEEEEEEEEG DGEEEDGDED EEAEAPTGKR VAEDDEDDDV DTKKQK-TEE DD
```

Fig. 1B

Rat Prothymosin alpha (1-112) :Seq.No.9
    MSDAAVDTSS EITTKDLKEK KEVVEEAENG RDAPANGNAQ NEENGEQEAD
    NEVDEEEEG GEEEEEEEEG DGEEEDGDED EEAEAPTGKR VAEDDEDDDV
    ETKKQKKTDE DD
C-terminal: Prothymosin alpha (102-112)
    TKKQKKTDE DD
P30: Prothymosin alpha (49-78) :Seq.No.10
    AD NEVDEEEEG GEEEEEEEEG DGEEEDGD

| | | |
|---|---|---|
| P1-9 | EVDEEEEEG | (PEPTIDE P9) :Seq.No.11 |
| P2-9: | VDEEEEEG | |
| P3-9: | DEEEEEG | |
| P1-8: | EVDEEEEE | |
| P1-7: | EVDEEEE | |
| P1-6: | EVDEEE | |
| P+1N/-1C: | NEVDEEEE | :Seq.No.30 |
| P+2N/-2C: | D NEVDEEEE | :Seq.No.31 |
| P+3N/-3C: | AD NEVDEEE | :Seq.No.13 |
| P+1N/-3C: | NEVDEEE | :Seq.No.32 |
| P+1N/-4C: | NEVDEE | (PEPTIDE P6) :Seq.No.1 |
| P+1N/-5C: | NEVDE | |

Fig. 2

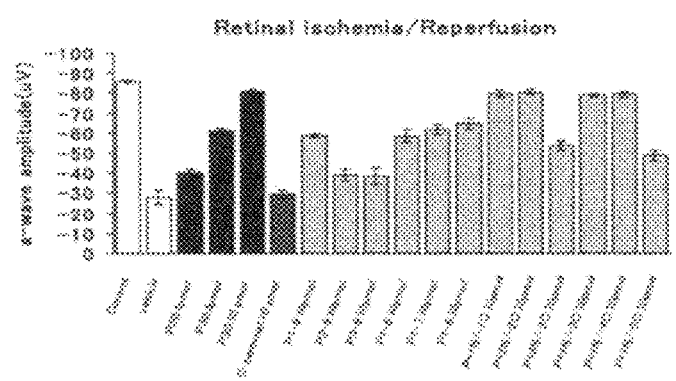

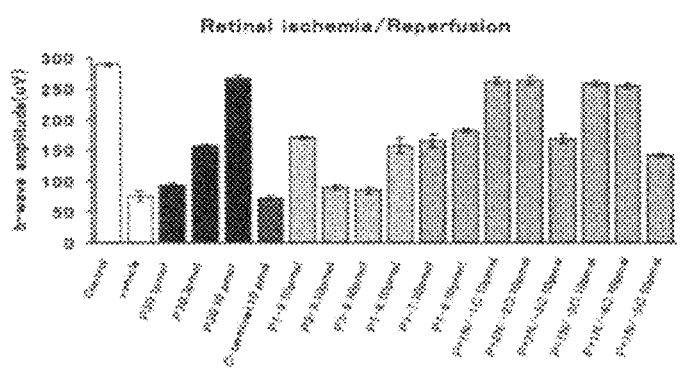

Fig. 5
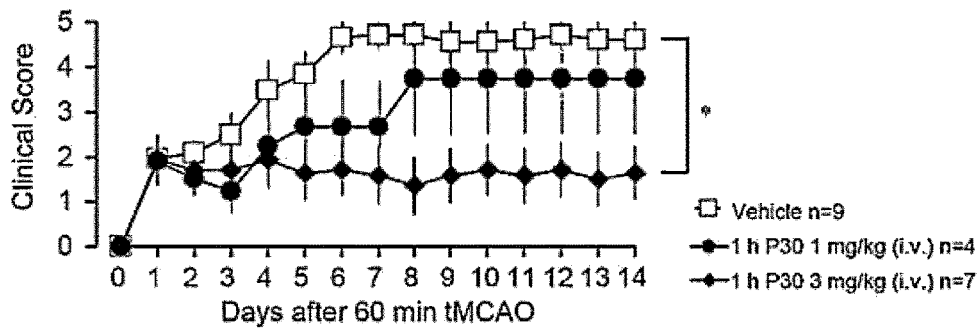
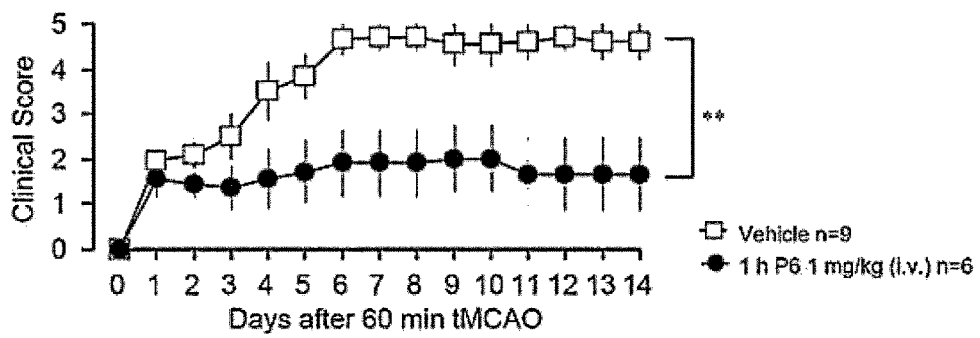
Fig. 6
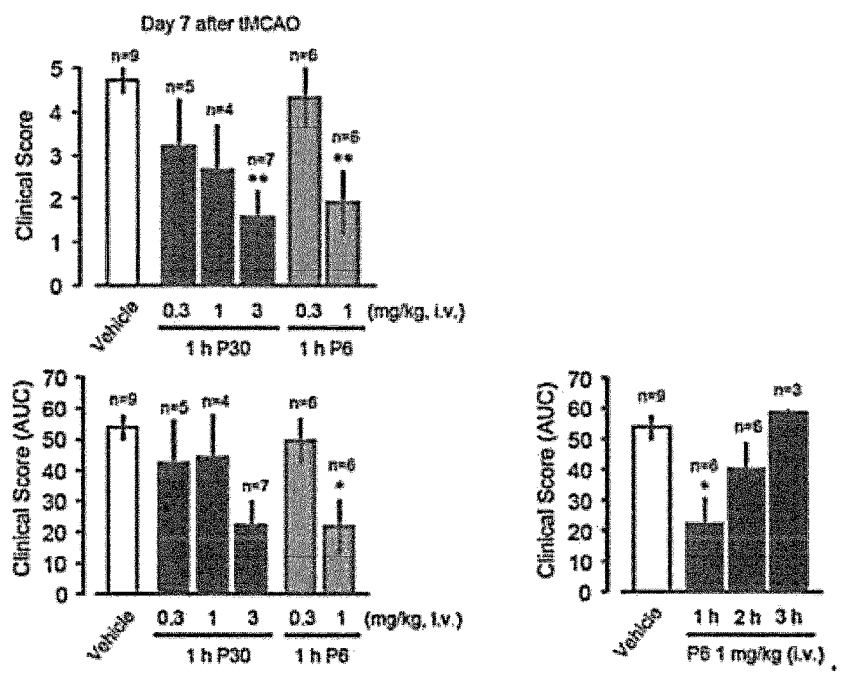

BASIC PEPTIDE P6 (n=3)

* WHEN CASES FROM 1 TO 4 ARE OBVIOUSLY OBSERVED, 0.5 POINTS ARE ADDED.

| PEPTIDE NAME | PEPTIDE SEQUENCE (DIFFERENCE FROM P6) |
|---|---|
| BASIC PEPTIDE: P6:Seq. No. 1 | NEVDEE |
| PEPTIDE A:Seq. No. 2 | NEVDQE |
| PEPTIDE B:Seq. No. 3 | pEEVNEE |
| PEPTIDE C:Seq. No. 4 | NEVEEE |
| PEPTIDE D:Seq. No. 5 | pEEVDEE |
| PEPTIDE E:Seq. No. 6 | NEVDEE-NH$_2$ |

| | | | | | |
|---|---|---|---|---|---|
| A | NEVDQE: Seq. No. 2 | H | NvaEVDEE: Seq. No. 16 | O | NEVDEQ: Seq. No. 23 |
| B | pEEVNEE: Seq. No. 3 | I | NleEVDEE: Seq. No. 17 | P | pEEVNEE-NH$_2$: Seq. No. 24 |
| C | NEVEEE: Seq. No. 4 | J | NQVDEE: Seq. No. 18 | Q | pEEVDQE: Seq. No. 25 |
| D | pEEVDEE: Seq. No. 5 | K | NELDEE: Seq. No. 19 | R | pEEVDQE-NH$_2$: Seq. No. 26 |
| E | NEVDEE-NH$_2$: Seq. No. 6 | L | NEIDEE: Seq. No. 20 | S | pEEVDEE-NH$_2$: Seq. No. 27 |
| F | Ac-NEVDEE-NH$_2$: Seq. No. 14 | M | NEVNEE: Seq. No. 21 | T | NEVNEE-NH$_2$: Seq. No. 28 |
| G | Ac-NEVDEE: Seq. No. 15 | N | NEVDED: Seq. No. 22 | U | NEVDQE-NH$_2$: Seq. No. 29 |

SEQUENCE LISTING

```
<160> NUMBER OF SEQ ID NOS: 32

<210> SEQ ID NO 1
<211> LENGTH: 6
<212> TYPE: PRT
<213> ORGANISM: Homo sapiens

<400> SEQUENCE: 1

Asn Glu Val Asp Glu Glu
1               5

<210> SEQ ID NO 2
<211> LENGTH: 6
<212> TYPE: PRT
<213> ORGANISM: Homo sapiens

<400> SEQUENCE: 2

Asn Glu Val Asp Gln Glu
1               5

<210> SEQ ID NO 3
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION

<400> SEQUENCE: 3

Glu Glu Val Asn Glu Glu
1               5

<210> SEQ ID NO 4
<211> LENGTH: 6
<212> TYPE: PRT
```

-continued

```
<213> ORGANISM: Homo sapiens

<400> SEQUENCE: 4

Asn Glu Val Glu Glu Glu
1               5

<210> SEQ ID NO 5
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION

<400> SEQUENCE: 5

Glu Glu Val Asp Glu Glu
1               5

<210> SEQ ID NO 6
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: AMIDATION

<400> SEQUENCE: 6

Asn Glu Val Asp Glu Glu
1               5

<210> SEQ ID NO 7
<211> LENGTH: 105
<212> TYPE: PRT
<213> ORGANISM: Homo sapiens

<400> SEQUENCE: 7

Met Ser Asp Ala Ala Val Asp Thr Ser Ser Glu Ile Thr Thr Glu Asp
1               5                   10                  15

Leu Lys Glu Lys Lys Glu Val Val Glu Glu Ala Glu Asn Gly Arg Asp
                20                  25                  30

Ala Pro Ala His Gly Asn Ala Asn Glu Glu Asn Gly Glu Pro Glu Ala
            35                  40                  45

Asp Asn Glu Val Asp Glu Glu Glu Glu Gly Gly Glu Glu Glu Glu Gly
        50                  55                  60

Asp Gly Glu Glu Glu Asp Gly Asp Glu Asp Glu Asp Gly Ala Glu Ser Ala
65                  70                  75                  80

Thr Gly Lys Arg Ala Ala Glu Asp Asp Glu Asp Asp Asp Val Asp Thr
                85                  90                  95

Gln Lys Gln Lys Thr Asp Glu Asp Asp
            100                 105

<210> SEQ ID NO 8
<211> LENGTH: 111
<212> TYPE: PRT
<213> ORGANISM: Mus musculus

<400> SEQUENCE: 8

Met Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Gly Arg Asp
                20                  25                  30
```

```
Ala Pro Ala Asn Gly Asn Ala Gln Asn Glu Glu Asn Gly Glu Gln Glu
            35                  40                  45

Ala Asp Asn Glu Val Asp Glu Glu Glu Glu Gly Gly Glu Glu Glu Glu
 50                  55                  60

Glu Glu Glu Glu Glu Gly Asp Gly Glu Glu Asp Gly Asp Glu Asp
 65                  70                  75                  80

Glu Glu Ala Glu Ala Pro Thr Gly Lys Arg Val Ala Glu Asp Asp Glu
            85                  90                  95

Asp Asp Asp Val Asp Thr Lys Lys Gln Lys Thr Glu Asp Asp
            100                 105                 110
```

```
<210> SEQ ID NO 9
<211> LENGTH: 112
<212> TYPE: PRT
<213> ORGANISM: Rattus norvegicus

<400> SEQUENCE: 9
```

```
Met Ser Asp Ala Ala Val Asp Thr Ser Ser Glu Ile Thr Thr Lys Asp
 1               5                   10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
            35                  40                  45

Ala Asp Asn Glu Val Asp Glu Glu Glu Glu Gly Gly Glu Glu Glu Glu
 50                  55                  60

Glu Glu Glu Glu Glu Gly Asp Gly Glu Glu Asp Gly Asp Glu Asp
 65                  70                  75                  80

Glu Glu Ala Glu Ala Pro Thr Gly Lys Arg Val Ala Glu Asp Asp Glu
            85                  90                  95

Asp Asp Asp Val Glu Thr Lys Lys Gln Lys Thr Asp Glu Asp Asp
            100                 105                 110
```

```
<210> SEQ ID NO 10
<211> LENGTH: 30
<212> TYPE: PRT
<213> ORGANISM: Artificial Sequence
<220> FEATURE:
<223> OTHER INFORMATION: Synthesized

<400> SEQUENCE: 10
```

```
Ala Asp Asn Glu Val Asp Glu Glu Glu Glu Gly Gly Glu Glu Glu
 1               5                   10                  15

Glu Glu Glu Glu Glu Gly Asp Gly Glu Glu Asp Gly Asp
            20                  25                  30
```

```
<210> SEQ ID NO 11
<211> LENGTH: 9
<212> TYPE: PRT
<213> ORGANISM: Artificial Sequence
<220> FEATURE:
<223> OTHER INFORMATION: Synthesized

<400> SEQUENCE: 11
```

```
Glu Val Asp Glu Glu Glu Glu Glu Gly
 1               5
```

```
<210> SEQ ID NO 12
<211> LENGTH: 7
<212> TYPE: PRT
<213> ORGANISM: Artificial Sequence
```

```
<220> FEATURE:
<223> OTHER INFORMATION: Synthesized

<400> SEQUENCE: 12

Asp Asn Glu Val Asp Glu Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthesized

<400> SEQUENCE: 13

Asn Glu Val Asp Glu Glu Glu
1               5

<210> SEQ ID NO 14
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 14

Asn Glu Val Asp Glu Glu
1               5

<210> SEQ ID NO 15
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: ACETYLATION

<400> SEQUENCE: 15

Asn Glu Val Asp Glu Glu
1               5

<210> SEQ ID NO 16
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (1)..(1)
<223> OTHER INFORMATION: Nva

<400> SEQUENCE: 16

Asn Glu Val Asp Glu Glu
1               5

<210> SEQ ID NO 17
<211> LENGTH: 6
```

```
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (1)..(1)
<223> OTHER INFORMATION: Nle

<400> SEQUENCE: 17

Asn Glu Val Asp Glu Glu
1               5

<210> SEQ ID NO 18
<211> LENGTH: 6
<212> TYPE: PRT
<213> ORGANISM: Artificial Sequence
<220> FEATURE:
<223> OTHER INFORMATION: Synthesized

<400> SEQUENCE: 18

Asn Gln Val Asp Glu Glu
1               5

<210> SEQ ID NO 19
<211> LENGTH: 6
<212> TYPE: PRT
<213> ORGANISM: Artificial Sequence
<220> FEATURE:
<223> OTHER INFORMATION: Synthesized

<400> SEQUENCE: 19

Asn Glu Leu Asp Glu Glu
1               5

<210> SEQ ID NO 20
<211> LENGTH: 6
<212> TYPE: PRT
<213> ORGANISM: Artificial Sequence
<220> FEATURE:
<223> OTHER INFORMATION: Synthesized

<400> SEQUENCE: 20

Asn Glu Ile Asp Glu Glu
1               5

<210> SEQ ID NO 21
<211> LENGTH: 6
<212> TYPE: PRT
<213> ORGANISM: Artificial Sequence
<220> FEATURE:
<223> OTHER INFORMATION: Synthesized

<400> SEQUENCE: 21

Asn Glu Val Asn Glu Glu
1               5

<210> SEQ ID NO 22
<211> LENGTH: 6
<212> TYPE: PRT
<213> ORGANISM: Artificial Sequence
<220> FEATURE:
<223> OTHER INFORMATION: Synthesized

<400> SEQUENCE: 22

Asn Glu Val Asp Glu Asp
1               5
```

```
<210> SEQ ID NO 23
<211> LENGTH: 6
<212> TYPE: PRT
<213> ORGANISM: Artificial Sequence
<220> FEATURE:
<223> OTHER INFORMATION: Synthesized

<400> SEQUENCE: 23

Asn Glu Val Asp Glu Gln
1               5

<210> SEQ ID NO 24
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION
<220> FEATURE:
<221> NAME/KEY: MOD_RES
<222> LOCATION: (6)..(6)
<223> OTHER INFORMATION: AMIDATION

<400> SEQUENCE: 24

Glu Glu Val Asn Glu Glu
1               5

<210> SEQ ID NO 25
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION

<400> SEQUENCE: 25

Glu Glu Val Asp Gln Glu
1               5

<210> SEQ ID NO 26
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION

<400> SEQUENCE: 26

Glu Glu Val Asp Gln Glu
1               5

<210> SEQ ID NO 27
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: GAMMA-CARBOXYGLUTAMIC ACID HYDROXYLATION
```

```
<220> FEATURE:
<221> NAME/KEY: MOD_RES
<222> LOCATION: (6)..(6)
<223> OTHER INFORMATION: AMIDATION

<400> SEQUENCE: 27

Glu Glu Val Asp Glu Glu
1               5

<210> SEQ ID NO 28
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (6)..(6)
<223> OTHER INFORMATION: AMIDATION

<400> SEQUENCE: 28

Asn Glu Val Asn Glu Glu
1               5

<210> SEQ ID NO 29
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (6)..(6)
<223> OTHER INFORMATION: AMIDATION

<400> SEQUENCE: 29

Asn Glu Val Asp Gln Glu
1               5

<210> SEQ ID NO 30
<211> LENGTH: 9
<212> TYPE: PRT
<213> ORGANISM: Rattus norvegicus

<400> SEQUENCE: 30

Asn Glu Val Asp Glu Glu Glu Glu Glu
1               5

<210> SEQ ID NO 31
<211> LENGTH: 9
<212> TYPE: PRT
<213> ORGANISM: Rattus norvegicus

<400> SEQUENCE: 31

Asp Asn Glu Val Asp Glu Glu Glu Glu
1               5

<210> SEQ ID NO 32
<211> LENGTH: 7
<212> TYPE: PRT
<213> ORGANISM: Rattus norvegicus

<400> SEQUENCE: 32

Asn Glu Val Asp Glu Glu Glu
1               5
```

AMELIORATING AGENT FOR BLOOD-BRAIN BARRIER DYSFUNCTION

TECHNICAL FIELD

The present invention relates to a peptide derived from prothymosin α, an ameliorating agent for blood-organ barrier dysfunction which contains the peptide as an active ingredient, and the like.

BACKGROUND ART

Cerebral stroke is an important disorder, which ranks fourth in Japanese mortality and ranks first in the causes of being bedridden, and is a disease caused due to cerebral ischemia. It can be said that treatment in the acute phase is important for cerebral ischemic diseases including cerebral stroke to improve the prognosis. A leading therapeutic method which has presently attracted the attention is a thrombolytic agent including a plasminogen activator (hereinafter, described as "tPA"); however, the use thereof is limited to within 4.5 hours and only a dozen or so percent of patients can benefit from the effects thereof (see Non Patent Literature 1). Part of the reason is that a blood-brain barrier becomes weak over time after cerebral ischemia and that the risk of hemorrhagic cerebral stroke increases due to the use of a thrombolytic agent such as tPA.

In recent years, the inventors have found for the first time that prothymosin α is a substance having a protective action on nerve cell death and cerebral apoplectic diseases can be alleviated by this inhibitory effect on nerve cell death (see Patent Literature 1). The inventors have also found that prothymosin α has an inhibitory effect on cerebral stroke and ischemic glaucoma in mice and rats (see Non Patent Literatures 2 to 4). The inventors have further found that prothymosin α has an action to protect a blood-brain barrier from a weakening in the blood-brain barrier, and have revealed an active body comprising 30 amino acids in rat prothymosin α and 9 amino acids in the sequence, which are important for the expression of its activity (see Patent Literature 2).

CITATION LIST

Patent Literatures

Patent Literature 1: WO 2004/064861 A
Patent Literature 2: WO 2011/019023 A

Non Patent Literatures

Non Patent Literature 1: Current medical practice: Medical practice: Medical practice and Nursing care: Yomiuri online article for Oct. 25, 2005, "New Drug tPA for Cerebral Infarction", http://www.yomiuri.co.jp/iryou/medi/saisin/20051025ik14.htm
Non Patent Literature 2: Journal of Cell Biology (2007), 176, 853-862
Non Patent Literature 3: Cell Death and Differentiation (2007), 14, 1839-1842
Non Patent Literature 4: Cell Death and Differentiation (2009), 16, 349-358

SUMMARY OF INVENTION

Technical Problem

A substance which can inhibit a weakening in a blood-organ barrier, which can be caused by ischemia, and can protect the blood-organ barrier is demanded, wherein the substance can be handled more readily than currently known peptides with an eye to an application to agents and the like. It is desired that the substance have a length of ten amino acids or less particularly in consideration of production readiness and profitability in the market.

Solution to Problem

As a result of intensive studies to solve the above-described problem, the present inventors found that a peptide comprising 6 amino acids from position 51 to 56 in prothymosin α (ProTα6, Peptide P6: SEQ ID NO:1) and peptides related to the peptide had characteristics such as improvement activity on blood-brain barrier dysfunction. The present inventors further intensively studied, thereby completing the present invention.

The above-described invention is basically based on the following knowledge. It has been found that in a polypeptide comprising the amino acid at position 52 to the amino acid at position 60 in rat prothymosin α described by ProTα9 disclosed in WO 2011/019023 A (Patent Literature 2), a peptide comprising the amino acid sequence in which one or two amino acids are deleted, added, substituted or inserted, or a peptide salt thereof (particularly a peptide shown in SEQ ID NO:30 or 31) shows a higher protective action on retinal ischemic dysfunction than that of ProTα9. Examples of these peptide are partial peptides obtained by transferring one to several residues on the N-terminus and C-terminus based on the above-described ProTα9.

```
                              (SEQ ID NO: 30)
P + 1N/-1C:   NEVDEEEEE (SEQ ID NO: 31)
P + 2N/-2C: D NEVDEEEE
```

It has been also found that ProTα6 (Peptide P6) previously explained and a peptide comprising 7 amino acids from position 51 to 57 in prothymosin α (ProTα7, Peptide P7: SEQ ID NO:32) have a protective action on retinal ischemic dysfunction.

```
                              (SEQ ID NO: 32)
Peptide P7 NEVDEEE
```

Peptide P6 was recognized to have an action on cerebral infarction-ischemia dysfunction by intravenous administration.

Among Peptide P6 derivatives, as peptides showing activity equal to or higher than that of P6, 20 peptides, Peptides A, B, C, D, E, F, G, H, I, J, K, M, N, O, P, Q, R, S, T and U, were found in a model of retinal ischemia.

As peptides showing a particularly high protective action on brain by systemic (intravenous) administration, in addition to P6, Peptides A and B, Peptide A showing an inhibitory action on hemorrhagic action during cerebral infarction by tPA, and Peptides A and F prolonging the effective time of the inhibitory action on cerebral infarction by tPA showed particularly excellent availability.

The first aspect of the present invention relates to a peptide comprising the amino acid sequence shown in SEQ ID NO:1 or the amino acid sequence shown in SEQ ID NO:1 in which one or two amino acids are deleted, added, substituted or inserted, or a peptide salt thereof. It is preferred that this peptide be a peptide having a function substantially equal to that of a peptide having the amino acid sequence shown in SEQ ID NO:1.

The peptide in this aspect or a salt thereof is preferably a peptide comprising the amino acid sequence shown in SEQ ID NO:1, SEQ ID NO:2, SEQ ID NO:3, SEQ ID NO:4, SEQ ID NO:5, SEQ ID NO:6, SEQ ID NO:12 or SEQ ID NO:13 or a salt thereof, and particularly preferably a peptide comprising the amino acid sequence shown in SEQ ID NO:2 or a salt thereof.

The second aspect of the present invention relates to a therapeutic agent for diseases associated with blood-organ barrier dysfunction, which contains any peptide described above or a salt thereof as an active ingredient. Thus, the therapeutic agent containing the peptide of the present invention or a salt thereof as an active ingredient is also referred to as the therapeutic agent of the present invention. This therapeutic agent contains any peptide described above or a salt thereof in an effective amount to be able to display its function. To put it more concretely, it can be said that this therapeutic agent is a therapeutic agent for diseases associated with blood-brain barrier dysfunction. To put it still more concretely, this therapeutic agent is a therapeutic agent for secondary vascular diseases due to atherosclerosis or hypertension, transient impairment of blood flow, hypertensive encephalopathy, intracranial and extracranial arterial embolism, infarction resulting from thrombosis, aneurysm, arteriovenous malformations, stenotic lesions of cerebral arteries, dural arteriovenous fistulas, vascular trauma, vascular tumors, virus encephalitis, edema due to weak angiogenesis after cerebral infarction, or hemorrhagic diseases due to weak angiogenesis after cerebral infarction. In the preferred mode, the therapeutic agent of the present invention is a therapeutic agent for ischemic diseases. Furthermore, in the preferred mode, the therapeutic agent of the present invention is a therapeutic agent for cerebral infarction. In the preferred mode, the therapeutic agent of the present invention is a therapeutic agent or a prophylactic agent for motor dysfunction or cerebral hemorrhage elicited by a thrombolytic agent. In the preferred mode, the therapeutic agent of the present invention is a nerve cell death inhibitor.

The third aspect of the present invention relates to a therapeutic agent for cerebral ischemic diseases, which contains the peptide of the present invention or a salt thereof and a thrombolytic agent as active ingredients. Since the peptide of the present invention or a salt thereof can treat or prevent motor dysfunction or cerebral hemorrhage elicited by a thrombolytic agent, combined use with a thrombolytic agent is effective. In this aspect, a preferred thrombolytic agent is a plasminogen activator. Furthermore, in this aspect, preferred indication is cerebral infarction. In this aspect, the peptide of the present invention or a salt thereof and a thrombolytic agent can be coadministered to an intended patient. In addition, a therapeutic effect by a thrombolytic agent 6 hours after cerebral infarction can be expected to be enhanced by preadministration of the peptide of the present invention or a salt thereof an hour before administration of the thrombolytic agent. By coadministration, characteristics by which critical side effects can be alleviated can be also expected, for example inhibiting the hemorrhagic action of a thrombolytic agent administered after 4 hours of cerebral infarction. The thrombolytic agent can elicit various side effects. By administering the peptide of the present invention or a salt thereof to patients suspected of having cerebral infarction, for example, more time to administer a thrombolytic agent can be obtained. Because of this, a thrombolytic agent will be able to be administered after cerebral infarction is revealed by a thorough medical examination.

Advantageous Effects of Invention

The ameliorating agent for blood-organ barrier dysfunction of the present invention can inhibit a weakening in blood-organ barriers which can be caused by ischemia and ameliorate blood-organ barrier dysfunction, and is particularly useful to inhibit a weakening in a blood-brain barrier which can be caused by cerebral ischemia (cerebral stroke etc.) and ameliorate blood-retina barrier dysfunction which can be caused by retinal ischemia. Therefore, the agent of the present invention can be a therapeutic agent for diseases caused by blood-organ barrier dysfunction.

Alternatively, even when a blood-organ barrier is weakened by each organ ischemia and a thrombolytic agent is decided not to be applied, ischemic diseases can be treated by using a conventionally known thrombolytic agent and the agent of the present invention in combination, without having to worry about side effects such as hemorrhage from the blood-organ barrier by a thrombolytic agent.

The active ingredient in the ameliorating agent for blood-organ barrier dysfunction of the present invention is a peptide comprising 6 amino acids from position 51 to 56 in prothymosin α (in the present description, can be described as "ProTα6" or "P6"; SEQ ID NO:1) or the like, wherein the peptide is more readily produced and processed than the full-length of conventionally known prothymosin α and a peptide derived from prothymosin α, and has an ameliorating effect on ischemia equal to or higher than that thereof. Therefore, such peptide is more useful as an active ingredient in an ameliorating agent for blood-organ barrier dysfunction, a therapeutic agent for diseases associated with blood-organ barrier dysfunction, a therapeutic agent for ischemic diseases and the like.

BRIEF DESCRIPTION OF DRAWINGS

FIG. 1A is a figure showing the amino acid sequences of prothymosin α derived from human, rat and mouse.

FIG. 1B is a figure showing peptides related to the present invention.

FIG. 2 shows figures in which the effects of peptides, in which the sequence of Peptide 9 is transferred or deleted on the sequence of rat prothymosin α, on functional disorders after a week of retinal ischemia were evaluated in ERG.

FIG. 5 shows figures showing the effects of ProTα peptides (P30 and P6) on clinical scores in a tMCAO ischemia model. In the figures, * and ** indicate P<0.05 and P<0.01, respectively, in the Repeated Measure ANOVA test.

FIG. 6, in the upper row, shows the results at 7 days after ischemia in FIG. 5 using a column graph, and the left graph in the lower row is a graph showing cumulative clinical scores for 14 days using AUC. The right graph in the lower row is a graph showing cumulative clinical scores for 14 days when administration timing of P6 after tMCAO is changed. In the figures, the Shirley-Williams test is used for statistics and * and ** indicate P<0.05 and P<0.01, respectively.

FIG. 10A is a graph showing retinal thickness.

FIG. 10B is a graph showing retinal potential values using a-wave.

FIG. 10C is a graph showing retinal potential values using b-wave.

FIG. 11A is a graph showing retinal potential values using a-wave.

FIG. 11B is a graph showing retinal potential values using b-wave.

FIG. 12A is a graph showing retinal potential values using a-wave.

FIG. 12B is a graph showing retinal potential values using b-wave.

FIG. 15A is a graph showing retinal potential values using a-wave when 10 mg/kg Peptide A or Peptide B is intravenously administered 24 hours after retinal ischemia.

FIG. 15B is a graph showing retinal potential values using b-wave when 10 mg/kg Peptide A or Peptide B is intravenously administered 24 hours after retinal ischemia.

FIG. 16B shows the scores in the cases of control (Vehicle), 1, 3 and 10 mg/kg P6 administration, tPA-alone control, and coadministration of tPA and 1, 3 and 10 mg/kg P6.

FIG. 16C shows the scores in the cases of control, 1, 3 and 10 mg/kg P6 administration, tPA-alone control, and coadministration of tPA+1, 3 and 10 mg/kg P6.

FIG. 17B shows the scores in the cases of intravenous coadministration of control, 10 mg/kg Peptides A, B, C, D or E with tPA.

FIG. 17C shows the scores in the cases of control, tPA-alone control, and coadministration of tPA and 10 mg/kg Peptides A, B, C, D or E.

FIG. 20A shows the results of control, tPA-alone control, combined use with 10 or 30 mg/kg Peptide A, and 30 mg/kg Peptide A-alone.

FIG. 20C shows the results of control, tPA-alone control, combined use with 10 or 30 mg/kg Peptide A, and 30 mg/kg Peptide A-alone.

MODE FOR CARRYING OUT THE INVENTION

Figure 3:
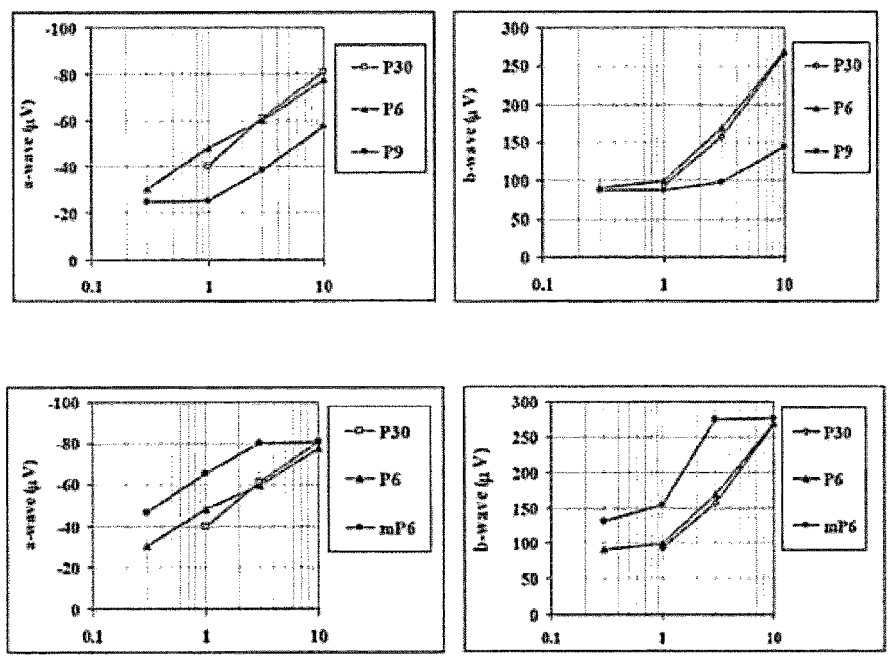
FIG. 3 shows figures showing the effects of P30, P9, P6 and mP6 (N-acetyl-P6-amide or Peptide F) on functional disorders by retinal ischemia. The left figures and right figures show the a-wave and b-wave, respectively, at the peptide concentrations shown.

The present invention will be described in detail.

Prothymosin α (hereinafter, can be described by "ProTα") is a known protein which is known to have a protective function against nerve cell death and an inhibitory function on nerve cell death and also have "the functions of remarkably inhibiting a weakening in a blood-brain barrier by cerebral ischemia and ameliorating blood-brain barrier dysfunction".

The above-described invention is basically based on the following knowledge. It has been found that in a polypeptide comprising the amino acid at position 52 to the amino acid at position 60 in rat prothymosin α described by ProTα9 disclosed in WO 2011/019023 A (Patent Literature 2), a peptide comprising the amino acid sequence in which one or two amino acids are deleted, added, substituted or inserted, or a peptide salt thereof (particularly a peptide shown in SEQ ID NO:30 or 31) shows a higher protective action on retinal ischemic dysfunction than that of ProTα9. Examples of these peptide are partial peptides obtained by transferring one to several residues on the N-terminus and C-terminus based on the above-described ProTα9.

```
                                      (SEQ ID NO: 30)
      P + 1N/-1C: NEVDEEEE (SEQ ID NO: 31)
      P + 2N/-2C: D NEVDEEEE
```

It has been also found that ProTα6 (Peptide P6) previously explained and a peptide comprising 7 amino acids from position 51 to 57 in prothymosin α (ProTα7, Peptide P7: SEQ ID NO:32) have a protective action on retinal ischemic dysfunction.

```
                                      (SEQ ID NO: 32)
      Peptide P7 NEVDEEE
```

Peptide P6 was recognized to have an action on cerebral infarction-ischemia dysfunction by intravenous administration.

Among Peptide P6 derivatives, as peptides showing activity equal to or higher than that of P6 in a model of retinal ischemia, 20 peptides, Peptides A, B, C, D, E, F, G, H, I, J, K, M, N, O, P, Q, R, S, T and U, were found.

As peptides showing a particularly high protective action on brain by systemic (intravenous) administration, in addition to P6, Peptides A and B, Peptide A showing an inhibitory action on hemorrhagic action during cerebral infarction by tPA, and Peptides A and F prolonging the effective time of the inhibitory action on cerebral infarction by tPA showed particularly excellent availability.

The peptide of the present invention or a salt thereof (can be simply referred to as the peptide of the present invention) is a peptide containing the same or the substantially same amino acid sequence shown in SEQ ID NO:1 or a salt thereof, and having the same activity as or higher activity than that of a peptide having the amino acid sequence shown in SEQ ID NO:1. The activity of a peptide having the amino acid sequence shown in SEQ ID NO:1 can be any one of activities evaluated in examples described below. Thus, the peptide of the present invention or a salt thereof is an isolated peptide or an isolated and purified peptide.

The peptide of the present invention can be also a peptide derived from cells of human and a mammal (e.g., guinea pig, rat, mouse, rabbit, pig, sheep, cattle or monkey). The peptide of the present invention can be also a partial peptide of prothymosin α or a peptide derived therefrom. Furthermore, the peptide of the present invention can be a synthetic peptide.

Examples of the peptide of the present invention are peptides comprising the amino acid sequence shown in SEQ ID NO:1 or the amino acid sequence shown in SEQ ID NO:1 in which one or two amino acids are deleted, added, substituted or inserted, or salts thereof. In the peptide of the present invention, for example, two or more types of deletions, additions, substitutions and insertions can exist like a peptide comprising an amino acid sequence in which one amino acid is deleted and one amino acid is substituted or a salt thereof.

It should be noted, for example, that those in which an amino acid residue and a terminus are modified are also contained in the substitutions. Examples of such substitutions are those in which an amino acid residue or a peptide terminus is acetylated or amidated.

Preferred examples of the peptide of the present invention are peptides comprising the amino acid sequence shown in SEQ ID NO:1, SEQ ID NO:2, SEQ ID NO:3, SEQ ID NO:4, SEQ ID NO:5 or SEQ ID NO:6, or salts thereof. Among these, preferred examples of the peptide of the present invention are peptides comprising the amino acid sequence shown in SEQ ID NO:2, or salts thereof.

In peptides in the present description, the left end is their N-terminus (amino terminus) and the right end is their C-terminus (carboxyl terminus) according to the practice of peptide notation. In the peptide of the present invention, the C-terminus can be a carboxyl group (—COOH), a carboxylate (—COO—), an amide (—CONH$_2$) or an ester (—COOR). Examples of R in the ester are a C$_{1-6}$ alkyl group, a C$_{3-8}$ cycloalkyl group, a C$_{6-12}$ aryl group, a C$_{7-14}$ aralkyl group and a pivaloyloxymethyl group. Examples of the C$_{1-6}$ alkyl group are a methyl group, an ethyl group, an n-propyl group, an isopropyl group, an n-butyl group, an s-butyl group and a t-butyl group. Examples of the C$_{3-8}$ cycloalkyl group are a cyclopentyl group and a cyclohexyl group. Examples of the C$_{6-12}$ aryl group are a phenyl group and an α-naphthyl group. Examples of the C$_{7-14}$ aralkyl group are a phenyl-C$_{1-2}$ alkyl group such as a benzyl group or a phenethyl group; and an α-naphthyl-C$_{1-2}$ alkyl group such as an α-naphthylmethyl group.

When the peptide of the present invention has a carboxyl group (or a carboxylate) excepting on the C-terminus thereof, those in which the carboxyl group is amidated or esterified are also contained in the peptide of the present invention. Examples of esters in this case are esters of the C-terminus described above.

In the peptides described above, those in which the amino group of a methionine residue on the N-terminus is protected with a protecting group, those in which a glutamyl group generated by in vivo cutting of the N-terminus side is pyroglutamylated, those in which a substituent on the side chain of an amino acid in a molecule is protected with a suitable protecting group, or conjugated peptides and conjugated proteins such as so-called glycopeptides and glycoproteins to which a sugar chain is bound, or the like are also contained in the peptide of the present invention. An example of the protecting group of the amino group of a methionine residue on the N-terminus is a C$_{1-6}$ acyl group, and an example of the C$_{1-6}$ acyl group is a C$_{2-6}$ alkanoyl group such as a formyl group or an acetyl group. Examples of substituents on the side chain of an amino acid in a molecule are —OH, —SH, an amino group, an imidazole group, an indole group and a guanidino group. An example of protecting group of a substituent on the side chain of an amino acid in a molecule is a C$_{1-6}$ acyl group, and an example of the C$_{1-6}$ acyl group is a C$_{2-6}$ alkanoyl group such as a formyl group or an acetyl group.

The salt of the peptide of the present invention is preferably a physiologically acceptable acid addition salt. Examples of such salts are salts with inorganic acids (such as hydrochloric acid, phosphoric acid, hydrobromic acid and sulfuric acid) and salts with organic acids (such as acetic acid, formic acid, propionic acid, fumaric acid, maleic acid, succinic acid, tartaric acid, citric acid, malic acid, oxalic acid, benzoic acid, methanesulfonic acid and benzenesulfonic acid).

The salt of the peptide of the present invention has the substantially same action as of the peptide of the present invention. Because of this, a case where a peptide salt is used and a case where a peptide salt is contained exist in examples of the present description. For convenience, even such cases are described as a case where only a peptide is used.

The peptide of the present invention can be produced by cutting prothymosin α disclosed in Patent Literature 1 or 2 or a polypeptide derived from prothymosin α using a suitable peptidase.

Therapeutic agent for various diseases in which the peptide of the present invention is involved The ameliorating agent for blood-brain barrier dysfunction of the present invention contains the peptide of the present invention as an active ingredient. Because of this, the ameliorating agent for blood-brain barrier dysfunction of the present invention can protect a blood-brain barrier from a weakening in the blood-brain barrier caused by cerebral ischemia and ameliorate blood-brain barrier dysfunction. Therefore, the ameliorating agent for blood-brain barrier dysfunction of the present invention can protect a blood-brain barrier by its neuroprotective action, as well as also ameliorate a blood-brain barrier weakened by cerebrovascular dysfunction, and thus is useful to prevent or treat all cerebral ischemic diseases, particularly diseases associated with blood-brain barrier dysfunction.

The "diseases associated with blood-brain barrier dysfunction" in the present invention includes all diseases known to cause abnormalities in a brood-brain barrier (e.g., diseases in which tight junctions of a blood-brain barrier is physically weakened, and diseases which result in abnormalities in substance transport in a blood-brain barrier, etc.), diseases resulting from abnormalities in a blood-brain barrier, and the like. Many of such diseases are diseases associated with cerebral ischemia, and specifically include secondary vascular diseases due to atherosclerosis or hypertension, transient impairment of blood flow, hypertensive encephalopathy, intracranial and extracranial arterial embolism, infarction resulting from thrombosis, aneurysm, arteriovenous malformations, stenotic lesions of cerebral arteries, dural arteriovenous fistulas, vascular trauma, vascular tumors, virus encephalitis, or edema or hemorrhagic diseases due to weak angiogenesis after cerebral infarction and the like, as well as cerebral stroke, traumatic encephalopathy, glaucoma, diabetic retinopathy or compressive disorders during treatment of detachment of the retina and the like. It should be noted that "treatment" as used herein contains not only a case where a disease is completely cured, but also a case where a disease condition is alleviated and a case where the worsening of disease condition is hindered, and the like.

As the "ameliorating agent for blood-brain barrier dysfunction" and "therapeutic agent for diseases associated with blood-brain barrier dysfunction" of the present invention, the preparations are produced by mixing the peptide of the present invention with a pharmaceutically acceptable carrier or diluent according to a known method. The appropriate pharmaceutically acceptable carrier or diluent is not particularly limited and a known carrier or diluent can be applied. Examples thereof include those described in Remington's Pharmaceutical Science and the like.

The "blood-organ barrier" in the present description means a system to control substance exchange between blood in a blood vessel and tissue fluid in an organ. The system to control substance exchange by a blood-organ barrier is supported by a mechanism to incorporate essential endogenous substances including amino acids and glucose, which are energy sources of nervous activity, in an organ, and a mechanism to discharge toxic substances, unnecessary foreign substances and the like in an organ into blood. These mechanisms can be controlled by many transporter transport systems expressed in capillary endothelial cells in each organ.

By anatomically observing a blood-brain barrier, which is a typical blood-organ barrier, it is understandable that cerebral capillary endothelial cells constituting the blood-brain barrier form tight junctions, which restricts substance permeability into intracellular spaces. That is, intravascular components do not flow into the central nervous system including brain tissues by the existence of the blood-brain barrier, and thus the biochemical homeostasis of the central nervous system is highly maintained. When abnormalities in a blood-brain barrier are caused, abnormalities in selective substance permeability between cerebrovascular vessels and brain are caused and these abnormalities will end up affecting the central nervous system.

Specifically, the blood-organ barriers include blood-brain barrier, blood-retinal barrier, blood-cerebrospinal fluid barrier, blood-bile barrier, blood-*thymus* barrier, blood-testis barrier and the like, and are preferably blood-organ barriers in the cranial nervous system organs such as blood-brain barrier and blood-retinal barrier.

In vessel infarction, ischemic symptoms are caused in not only an infarct site but also a blood-organ barrier. Since a vessel in a portion in which ischemic symptoms are caused is rapidly weakened, when blood flow is reperfused, there is a high possibility of hemorrhage from a blood-organ barrier. Particularly in the case of cerebral ischemia such as cerebral infarction, the vessel walls in a blood-brain barrier are rapidly weakened, which has a very high risk for hemorrhage with blood reperfusion.

Therefore, a thrombolytic agent such as tPA which should be examined whether or not to apply to the treatment of vessel infarction, for example in the case of cerebral infarction, can be used only when a morbid state thereof can be confirmed within 6 hours (preferably 3 hours) after infarction, and thus in most cases, the agent cannot be used.

In contrast, ProTα can be used for the treatment of diseases like cerebral infarction in which removal of a thrombus is urgently required but hemorrhage should be certainly avoided. That is, ProTα not only can inhibit nerve cell death around the infarct site to maintain organ homeostasis and can ameliorate the infarct site lesion, but also, as described below, can be used for the purpose of ameliorating the fragility of a blood-organ barrier such as a blood-brain barrier so that a thrombolytic agent such as tPA can be used in combination therewith.

The "blood-organ barrier dysfunction" in the present invention means to cause some kind of abnormality in a blood-organ barrier. Such abnormalities include abnormalities in selective substance permeability in a blood-organ barrier, the breakdown of tight junctions of capillary endothelial cells (expansion of intracellular spaces), a decrease in capillary endothelial cells, and further disorders resulting from hypofunction of a blood-organ barrier, such as edema and jaundice.

The "blood-organ barrier dysfunction" in the present invention specifically includes not only symptoms generally caused in the above-described blood-organ barrier dysfunction, but also, for example, a decrease in cerebral capillary endothelial cells associated with blood-brain barrier dysfunction and fever associated therewith, encephalitic symptoms such as cerebral edema, every possible higher cerebral functional disorder such as memory and learning, appetite and sleep disorders and emotional pain, autonomic diseases associated with blood pressure, respiration and digestive organ symptoms, headache, vomiting and cerebral herniation associated with increased intracranial pressure symptoms, and the like. In addition, when an organ is a retina, the dysfunction, for example, includes central serous chorioretinopathy.

The ameliorating agent for blood-organ barrier dysfunction of the present invention ameliorates such blood-organ barrier dysfunction and protects the blood-organ barrier.

An abnormality in a blood-organ barrier can be found by confirming the quantity and length of capillary vessels around the blood-organ barrier.

When an abnormality in a blood-brain barrier is confirmed, for example, the quantity and length of capillary vessels in the perceptual domain of cerebral cortex are compared with those in the normal state. That is, when the quantity and/or length of capillary vessels are reduced in the perceptual domain of cerebral cortex, it can be decided that abnormalities in the blood-brain barrier are caused with cerebral infarction, and when the quantity and/or length of capillary vessels in the perceptual domain of cerebral cortex are appropriate, it can be decided that there are no abnormalities in the blood-brain barrier. The length and quantity of capillary vessels can be discriminated by methods known per se, and such methods include staining of vessel endothelial cells by lectin (e.g., tomato lectin) described in "Seitai no Kagaku; Volume 55(3), page 266-272 (by Shunichi Morikawa and Taichi Ezaki), 2004".

The peptide comprising the amino acid sequence (NEVDEE) shown in SEQ ID NO:1 can be utilized as an active ingredient of the ameliorating agent for blood-organ barrier dysfunction, the therapeutic agent for diseases associated with blood-organ barrier dysfunction or ischemic diseases, the nerve cell death inhibitor of the present invention and the like.

The peptide comprising the amino acid sequence shown in SEQ ID NO:1 is a peptide (referred to as ProTα6) comprising 6 amino acids from position 51 to 56 in rat prothymosin α. Such peptide has the same sequence as in any animal species, for example, not only prothymosin α derived from rat (SEQ ID NO:8) but also a corresponding peptide in prothymosin α derived from human (SEQ ID NO:6), a corresponding peptide in prothymosin α derived from mouse (SEQ ID NO:7) (FIG. 1).

The peptide comprising the amino acid sequence shown in SEQ ID NO:1 is a peptide having the functions of prothymosin α, for example protective and ameliorative functions on blood-organ barrier dysfunction (e.g., an action to promote translocation of GLUT4 to the cell membrane surface etc.), a protective function against nerve cell death and an inhibitory function on nerve cell death (e.g., an inhibitory function on nerve cell necrosis, a promoting function on nerve cell apoptosis, an inhibitory function on indirect apoptosis of nerve cells etc.) and the like. Such peptide is a peptide which is made even shorter than a peptide derived from conventionally known prothymosin α with the function maintained for the purpose of easier application to drug seeds.

As previously explained, in the present invention, a "peptide having a substantially equal function" to that of a peptide comprising the amino acid sequence shown in SEQ ID NO:1 or the amino acid sequence shown in SEQ ID NO:1 in which one or two amino acids are deleted, added, substituted and/or inserted or a salt thereof, wherein the peptide comprises the amino acid sequence shown in SEQ ID NO:1, can be also used in place of the peptide comprising the amino acid sequence shown in SEQ ID NO:1. The "peptide having a substantially equal function" as used herein has the same functions as of the above-described "peptide comprising the amino acid sequence shown in SEQ ID NO:1" ("equal function" as used herein means that the quality of functions is equal and does not mention the strength of activity and action thereof), for example protective and ameliorative functions on blood-organ barrier dysfunction (e.g., an action to promote translocation of GLUT4 to the cell membrane surface etc.), a protective function against nerve cell death and an inhibitory function on nerve cell death (e.g., an inhibitory function on nerve cell necrosis, a promoting function on nerve cell apoptosis, an inhibitory function on indirect apoptosis of nerve cells etc.) and the like, and includes a peptide having the amino acid sequence of "a peptide comprising the amino acid sequence shown in SEQ ID NO:1" in which one or several amino acids are deleted, added, substituted and/or translocated. Here, as long as a peptide has the same functions as of prothymosin α, the number of amino acids to be deleted, added, substituted and/or translocated is not particularly limited and is preferably within 2 amino acids and more preferably one amino acid. Amino acids which can be deleted, added, substituted and/or translocated can be suitably decided depending on a balance between desired functions and peptide modification described below by those skilled in the art.

The present inventors have found, however, that a 7 amino acid peptide comprising amino acids from position 50 to 56 in rat prothymosin α and a 7 amino acid peptide comprising amino acids from position 51 to 57 therein also have an activity equal to that of a peptide comprising the amino acid sequence shown in SEQ ID NO:1, but in a 5 amino acid peptide comprising amino acids from position 51 to 55 and a 8 amino acid peptide comprising amino acids from position 49 to 56, the activity declines (data not shown). Therefore, preferred examples of peptides having a function substantially equal to that of a peptide comprising the amino acid sequence shown in SEQ ID NO:1 include peptides in which an amino acid is added, specifically SEQ ID NO:12 (position 50 to 56) and SEQ ID NO:13 (position 51 to 57).

These peptides can be non-naturally occurring peptides and can be produced by peptide synthesis methods known per se. The deletion, addition, substitution or translocation of amino acids can be carried out by methods known per se.

The peptide of the present invention can be modified as long as the peptide has the functions of prothymosin α, for example protective and ameliorative functions on blood-organ barrier dysfunction (e.g., an action to promote translocation of GLUT4 to the cell membrane surface etc.), a protective function against nerve cell death and an inhibitory function on nerve cell death (e.g., an inhibitory function on necrosis, an apoptosis promoting function, an inhibitory function on indirect apoptosis of nerve cells etc.) and the like.

The modification of peptides includes fluorescent labeling (e.g., FITC labeled, Dns labeled, Nma labeled etc.), other labeling (e.g., biotin labeling etc.), modification by a fatty acid (e.g., DHA modification etc.), phosphorylation, sulfonation, hydroxylation, methylation, acetylation, prenylation, palmitoylation, carboxylation modification of amino groups (e.g., acetylation, formylation, pyroglutamylation, amidation, succinylation, biotinylation, benzyloxycarbonylation, Dnp labeled, Dns labeled, myristoylation etc.), modification of thiol groups (e.g., farnesylation, geranylation etc.), modification by sugars (e.g., an Asn (Glc-NAc)-containing peptide etc.), addition of glycosylphosphatidylinositol, ubiquitination, modification of peptide bonds (e.g., a reduced form, a statin form etc.) and the like. In order to adjust desired functions, preferred modification modes can be suitably selected by those skilled in the art.

When the peptide of the present invention is modified, a modified position in the peptide is not particularly limited and modification on the peptide termini is preferable.

The modification method of the peptide termini is not particularly limited without inhibiting the above-described functions of the peptide of the present invention, and is desirably acetylation or amidation in terms of improving such functions or inhibiting the in vivo degradation of the peptide of the present invention. The functions of the peptide of the present invention can be improved or the in vivo degradation can be inhibited by acetylating or amidating the peptide termini of the peptide of the present invention.

The acetylation or amidation of the peptide termini can be carried out by suitably selecting an appropriate technique by those skilled in the art. The peptide of the present invention is, for example, a peptide in which the N-terminus is acetylated and/or the C-terminus is amidated. The most preferred peptide of the present invention is a peptide which has the amino acid sequence shown in SEQ ID NO:1 and in which the N-terminus is acetylated and the C-terminus is amidated (N-acetyl-P6-amide; also referred to as mP6 and Peptide F).

The "ameliorating agent for blood-brain barrier dysfunction" of the present invention contains the peptide of the present invention as an active ingredient, and thus not only can inhibit nerve cell death around an infarct site to maintain homeostasis in an organ and ameliorate dysfunction in the infarct site, but also further can ameliorate a weakening in a blood-organ barrier caused by ischemia, and protect the blood-organ barrier.

That is, the ameliorating agent for blood-organ barrier dysfunction of the present invention can protect nervous tissue around a blood-organ barrier by the cytoprotective action of the peptide of the present invention, as well as also can ameliorate a blood-organ barrier weakened by vascular diseases, and protect the blood-organ barrier. Therefore, the ameliorating agent for blood-organ barrier dysfunction of the present invention is useful to prevent or treat all ischemic diseases and diseases associated with blood-organ barrier dysfunction, particularly ischemic diseases in cranial nervous system tissue and diseases associated with blood-organ barrier dysfunction in the cranial nervous system organ.

The "diseases associated with blood-organ barrier dysfunction" in the present invention includes all diseases known to cause abnormalities in a blood-organ barrier, diseases resulting from abnormalities in a blood-organ barrier and the like. Such diseases include diseases resulting from a physically weakening in the tight junctions of a blood-organ barrier, diseases resulting from abnormalities in substance transport in a blood-organ barrier, and the like.

The organ is preferably the cranial nervous system organ. The "peptide of the present invention" contained in "the therapeutic agent for diseases associated with blood-organ barrier dysfunction" of the present invention effectively works against particularly blood-organ barrier dysfunction in the cranial nervous system, and thus such agent is useful to treat diseases associated with blood-organ barrier dysfunction in the cranial nervous system.

When the blood-organ barrier dysfunction is blood-brain barrier dysfunction, most of diseases associated with blood-brain barrier dysfunction are diseases associated with cerebral ischemia, and such diseases specifically include secondary vascular diseases due to atherosclerosis or hypertension, transient impairment of blood flow, hypertensive encephalopathy, intracranial and extracranial arterial embolism, infarction resulting from thrombosis, aneurysm, arteriovenous malformations, stenotic lesions of cerebral arteries, dural arteriovenous fistulas, vascular trauma, vascular tumors, virus encephalitis, or edema, jaundice or hemorrhagic diseases due to weak angiogenesis after cerebral infarction and the like, as well as cerebral stroke, traumatic encephalopathy, and the like.

In addition, when the blood-organ barrier dysfunction is blood-retina barrier dysfunction, diseases associated with blood-retinal barrier dysfunction specifically include glaucoma, diabetic retinopathy or compressive disorders during treatment of detachment of the retina and the like.

It should be noted that "treatment" of diseases as used herein contains not only a case where a disease is completely cured, but also a case where a disease condition is alleviated and a case where the worsening of disease condition is hindered, and the like.

The "ischemic diseases" in the present invention mean various diseases caused by ischemia. Ischemia is caused by various causes such as arterial infarction due to a thrombus, and stenosis of an artery itself.

The ischemic diseases include ischemic diseases caused by ischemia of cranial nervous system tissue (cerebral stroke, cerebral infarction, cerebral thrombosis, transient cerebral ischemic attack etc.), ischemic diseases caused by ischemia of cardiac tissue (ischemic heart diseases; e.g., myocardial infarction, angina pectoris etc.), and ischemic bowel diseases caused by ischemia of intestinal tissue (ischemic bowel diseases; e.g., acute mesenteric artery occlusion, ischemic colitis, abdominal angina etc.), and are preferably ischemic diseases caused by ischemia of cranial nervous system tissue.

By using "the therapeutic agent for ischemic diseases" of the present invention in combination with a thrombolytic agent, meanwhile, the application range of the thrombolytic agent can be expanded. By using "the therapeutic agent for ischemic diseases" of the present invention in combination with a thrombolytic agent, in particular, ischemic diseases resulting from vessel infarction can be more effectively treated.

In general, a thrombolytic agent can be used only for patients in the acute phase of vessel infarction, that is, within a period in which a conventional vessel structure is maintained (e.g., in the case of cerebral infarction, within 3 hours after the onset of the disease), and it is therefore required that the agent be used after confirming no hemorrhage by CT, MRI and the like. This is because, since a blood-organ barrier is weakened by ischemia, in the case of not the early phase of the disease onset in which the structure of the blood-organ barrier is relatively maintained, the risk of causing side effects such as hemorrhage by the effect of a thrombolytic agent is increased. Therefore, it is desired that, in the case of cerebrovascular diseases including cerebral infarction, in particular, a thrombolytic agent be used in the state in which intracranial hemorrhage is not observed or there are no risks of hemorrhage, and thus it is often that many doctors facing cerebrovascular diseases do not use a thrombolytic agent which they originally want to use in fear of a risk of hemorrhage.

The peptide of the present invention contained in "the therapeutic agent for ischemic diseases" of the present invention, however, not only can inhibit nerve cell death around an infarct site to maintain homeostasis in an organ and ameliorate dysfunction in the infarct site, but also further can ameliorate a weakening in a blood-organ barrier caused by ischemia, and protect the blood-organ barrier. The peptide of the present invention does not cause hemorrhage and thus can be early administered in the treatment of ischemic diseases and the like without confirming the presence or absence of hemorrhage. By using the peptide of the present invention, or "the therapeutic agent for ischemic diseases" of the present invention, therefore, the structure of a blood-organ barrier is maintained and the risk of hemorrhage from weak vessels believed to be side effects by a thrombolytic agent becomes extremely low.

By, when using a thrombolytic agent, using "the therapeutic agent for ischemic diseases" of the present invention in combination therewith, therefore, the thrombolytic agent can be used without depending on the time of the onset of vessel infarction. Because of this, various ischemic diseases can be effectively treated. In cerebral ischemic diseases (e.g., cerebral infarction, cerebral stroke etc.), in particular, a thrombolytic agent could have been used only for 3 hours after the disease onset, but by combined use with the therapeutic agent for ischemic diseases of the present invention, a thrombolytic agent can be used even after a lapse of 3 hours, and the selection range of treatment routes for cerebral ischemic diseases in the acute phase is dramatically expanded.

Therefore, the present invention provides a therapeutic agent for ischemic diseases, which contains the peptide of the present invention as an active ingredient, as well as a combination of the therapeutic agent for ischemic diseases and a thrombolytic component. It should be noted that such thrombolytic component can be contained in the therapeutic agent for ischemic diseases of the present invention, or can be used as a thrombolytic agent different from the therapeutic agent for ischemic diseases.

The thrombolytic agents (thrombolytic components) which can be used in combination with the therapeutic agent for ischemic diseases of the present invention specifically include, but not limited to, tPA, urokinase, streptokinase, nattokinase, pro-urokinase, staphylokinase, desmoteplase, APSAC and the like, or peptides derived from these thrombolytic components. A preferred thrombolytic agent is tPA. As used herein, "the peptides derived from these thrombolytic components" mean peptides which each have the activities of the above-described thrombolytic components and peptides which have the same amino acid sequence as a part of or the whole full length amino acid sequence of each component derived from a thrombus (protein).

Commercially available tPA can be used or one which is synthesized by a known method can be used.

Furthermore, the therapeutic agent for ischemic diseases of the present invention can be used in combination with other known therapeutic agents for vascular diseases (therapeutic components for vascular diseases). Other known therapeutic agents for vascular diseases are not particularly limited and include, for example, radical scavenger (edaravone) in addition to the above-described thrombolytic agents.

The combinations of the therapeutic agent for ischemic diseases of the present invention and a thrombolytic agent (thrombolytic component) include (1) a method in which a preparation is produced using the therapeutic agent for ischemic diseases of the present invention together with a thrombolytic component, which is administered as a single agent (combination drug), (2) a method in which preparations of the therapeutic agent for ischemic diseases of the present invention and a thrombolytic component are individually produced, which are simultaneously administered, (3) a method in which preparations of the therapeutic agent for ischemic diseases of the present invention and a thrombolytic component are individually produced, which are administered at an interval (e.g., the therapeutic agent for ischemic diseases of the present invention is first administered and a thrombolytic component is then administered), and the like, but can be administered by an administration method which is not limited to these methods.

The dosage of other known therapeutic agents for vascular diseases which are combined can be suitably changed depending on required conditions such as its purpose, and the age, body weight, sex and extent of a disease of a subject to be administered, and, for example in the case of tPA, an amount which is generally used for the treatment of ischemic diseases can be used, and is commonly about 10 mg/kg for rodents and about 0.6 mg/kg for human.

In the combination of the therapeutic agent for ischemic diseases of the present invention and a thrombolytic composition, a period in which the thrombolytic component can be used can be prolonged. In order to display such effect, in the case of human, the peptide of the present invention can be administered in an amount of about 0.1 mg/kg to 10 mg/kg, preferably about 0.3 mg/kg to 3.0 mg/kg and most preferably about 1 mg/kg with respect to about 0.1 mg/kg to 1.0 mg/kg, preferably about 0.3 mg/kg to about 0.9 mg/kg and most preferably about 0.6 mg/kg of tPA. In the case of mouse, the peptide of the present invention can be administered in an amount of about 0.1 mg/kg to 10 mg/kg, preferably about 0.3 mg/kg to 3.0 mg/kg and most preferably about 1 mg/kg with respect to about 1 mg/kg to 30 mg/kg, preferably about 3 mg/kg to about 20 mg/kg and most preferably about 10 mg/kg of tPA.

As described above, the peptide of the present invention is a peptide having a protective function against nerve cell death and an inhibitory function on nerve cell death (e.g., an inhibitory function on nerve cell necrosis, a promoting function on nerve cell apoptosis, an inhibitory function on indirect apoptosis of nerve cells etc.), and thus an agent comprising the peptide of the present invention can be used as nerve cell death inhibitor.

Therefore, the present invention provides a nerve cell death inhibitor, which contains the peptide of the present invention as an active ingredient.

The preparations of "the ameliorating agent for blood-organ barrier dysfunction", "the therapeutic agent for diseases associated with blood-organ barrier dysfunction", "the therapeutic agent for ischemic diseases" and "the nerve cell death inhibitor" of the present invention (hereinafter, these can be collectively described as "the agents of the present invention") are produced by mixing the peptide of the present invention with a pharmaceutically acceptable carrier or diluent and further, as necessary, the above-described combination components according to a known method.

The appropriate pharmaceutically acceptable carrier or diluent is not particularly limited, and carriers or diluents known per se can be applied and, for example, include those described in Remington's Pharmaceutical Sciences and the like.

The dosage form of the agents of the present invention is not particularly limited and dosage forms known per se can be applied. However, as is the case with known therapeutic drugs for vascular diseases in an organ, the agents of the present invention are preferably prepared as injections for vascular administration, and in the case of an agent for blood-brain barrier dysfunction, in particular, the agents are preferably prepared as injections for cerebroventricular administration.

More specifically, an injection is obtained by dissolving the peptide of the present invention in a suitable solvent such as water, a physiological saline solution or an isotonic buffer solution. At this time, polyethylene glycol, glucose, various kinds of amino acids, collagen, albumin or the like can be added as a protective agent to prepare injections. In addition, the peptide can be embedded in an inclusion body such as ribosome and administered.

When the peptide of the present invention is used for treatment of the above-described diseases, the dose of the peptide of the present invention as an active ingredient is not particularly limited, and varies depending on the age, body weight and conditions of a subject, administration routes and other elements, and can be easily and suitably decided by doctors who administer it and the like.

The administration method for the peptide of the present invention or the agents of the present invention is not particularly limited, and various administration methods which are actually carried out can be applied. An example of such administration methods can include intracisternal administration. The intracisternal administration is advantageous in terms of not injuring cerebral parenchyma. The administration can be also carried out by parenteral administration (e.g., intravascular administration (e.g., intravenous administration), cerebroventricular administration etc.), oral administration and the like.

When the peptide of the present invention is systemically administered, for example intravenously administered, the daily dosage is, for example, about 0.1 mg/kg to 10 mg/kg, preferably about 0.3 mg/kg to 3.0 mg/kg and most preferably about 1 mg/kg. In addition, when the peptide of the present invention is locally administered, for example intravitreally administered, the peptide is administered so that the one dosage will be about 0.1 pmol to 20 pmol and preferably about 1 pmol to 10 pmol.

In the preferred mode, the therapeutic agent of the present invention is a therapeutic agent or a prophylactic agent for motor dysfunction or cerebral hemorrhage elicited by a thrombolytic agent. As proved in examples, the peptide of the present invention or a salt thereof can prevent motor dysfunction or cerebral hemorrhage elicited by a thrombolytic agent. Because of this, for example, by using the peptide of the present invention or a salt thereof in combination with a thrombolytic agent, motor dysfunction and cerebral hemorrhage elicited by a thrombolytic agent can be prevented.

In the preferred mode, the agents of the present invention are therapeutic agents for cerebral ischemic diseases, which contain the peptide of the present invention or a salt thereof and a thrombolytic agent as active ingredients. Since the peptide of the present invention or a salt thereof can treat or prevent motor dysfunction or cerebral hemorrhage elicited by a thrombolytic agent, combined use with a thrombolytic agent is effective. In this aspect, a preferred thrombolytic agent is a plasminogen activator. Furthermore, in this aspect, preferred indication is cerebral infarction. In this aspect, the peptide of the present invention or a salt thereof and a thrombolytic agent can be coadministered to an intended patient. In addition, a thrombolytic agent can be administered within 30 minutes to 5 hours (or within an hour to 3 hours) after the peptide of the present invention or a salt thereof is administered to a subject. A thrombolytic agent can elicit various side effects. By administrating the peptide of the present invention or a salt thereof to patients suspected of having cerebral infarction, for example, more time to administer a thrombolytic agent can be obtained. Because of this, a thrombolytic agent can be administered after cerebral infarction is revealed by a thorough medical examination.

The present invention also provides a method for treating diseases associated with blood-brain barrier dysfunction, the method comprising the step of administering the peptide of the present invention (the peptide comprising the amino acid sequence shown in SEQ ID NO:1 or the amino acid sequence shown in SEQ ID NO:1 in which one or two amino acids are deleted, added, substituted and/or inserted, or a salt thereof) to a subject (e.g., human) in an amount effective to treat diseases associated with blood-brain barrier dysfunction.

Examples of diseases associated with blood-brain barrier dysfunction are secondary vascular diseases due to atherosclerosis or hypertension, transient impairment of blood flow, hypertensive encephalopathy, intracranial and extracranial arterial embolism, infarction resulting from thrombosis, aneurysm, arteriovenous malformations, stenotic lesions of cerebral arteries, dural arteriovenous fistulas, vascular trauma, vascular tumors, virus encephalitis, edema due to weak angiogenesis after cerebral infarction, and hemorrhagic diseases caused due to weak angiogenesis after cerebral infarction.

The present invention also provides a method for treating cerebral infarction, the method comprising the step of administering the peptide of the present invention to a subject (e.g., human) in an amount effective to treat cerebral infarction.

The present invention also provides a method for treating cerebral ischemic diseases, the method comprising the step of administering the peptide of the present invention and a thrombolytic agent to a subject (e.g., human) in an amount effective to treat cerebral ischemic diseases. An example of the thrombolytic agent is a plasminogen activator. This method is effective particularly for treatment of cerebral infarction. That is, by using a thrombolytic agent in combination with the peptide of the present invention, time for which treatment using a thrombolytic agent can be carried out can be prolonged, and further hypanakinesia by a thrombolytic agent can be prevented. The peptide of the present invention and a thrombolytic agent can be coadministered to a subject. On the other hand, for example, when cerebral stroke is suspected, the peptide of the present invention is quickly administered, and after that, a thrombolytic agent can be administered to a subject within 30 minutes to 5 hours (or within an hour to 3 hours) depending on test results.

EXAMPLES

The present invention will now be described in more detail by way of examples thereof.

Example 1

Search for P6

With the aim of derivatization of Peptide 9 (=ProTα9) having been already specified in Patent Literature 2, the effects of 11 types of peptides were evaluated, in which the amino acid sequence is shifted back and forth or the N-terminus and the C-terminus are deleted, or the like. In the activity evaluation, ERG after a week in a model of retinal ischemia was used as an index. The results are shown in FIG. 2. In the figure, P1-9 indicates Peptide 9 and +1N/−1C indicates that in the sequence of Peptide 9, one amino acid was added on the N-terminal side and one amino acid was deleted on the C-terminal side.

A 9 amino acid peptide comprising amino acids from position 50 to 58 in rat prothymosin α (P+2N/−2C) and a 7 amino acid peptide comprising amino acids from position 51 to 57 (P+1N/−3C) also had an activity equal to that of a peptide comprising amino acids from position 51 to 56 (P+1N/−4C), but in a 5 amino acid peptide comprising amino acids from position 51 to 55 (P+1N/−5C) and a 9 amino acid peptide comprising amino acids from position 49 to 57 (P+3N/−3C), the activity declined. Therefore, Peptide P6 (P+1N/−4C; i.e., ProTα6) having the amino acid sequence shown in SEQ ID NO:1 was found as a peptide sequence which is the shortest and maintains its activity.

FIG. 1B is a figure showing peptides related to the present invention. The rat prothymosin α (1-112) described in FIG. 1B is the full length rat prothymosin α having the sequence shown in SEQ ID NO:9. The C-terminal rat prothymosin α is a peptide having the amino acid sequence from position 102 to 112 in the full length rat prothymosin α having the amino acid sequence shown in SEQ ID NO:9. P30 is ProTα30 shown in SEQ ID NO:10 (a peptide having the amino acid sequence from position 49 to 78 in the full length rat prothymosin α having the sequence shown in SEQ ID NO:9). P1-9 is a peptide having the amino acid sequence shown in SEQ ID NO:11 (Peptide P9, ProTα9). ProTα9 is a peptide having the amino acid sequence from position 52 to 60 in the full length rat prothymosin α having the amino acid sequence shown in SEQ ID NO:9. P2-9 is a peptide having the amino acid sequence from position 2 to 9 in ProTα9. P3-9 is a peptide having the amino acid sequence from position 3 to 9 in ProTα9. P1-8 is a peptide having the amino acid sequence from position 1 to 8 in ProTα9. P1-7 is a peptide having the amino acid sequence from position 1 to 7 in ProTα9. P1-6 is a peptide having the amino acid sequence from position 1 to 6 in ProTα9. P+1N/−1C is a peptide (peptide shown in SEQ ID NO:30) having the sequence in which one returns to the N-terminal side and one returns on the C-terminal side in ProTα9 (the amino acid sequence from position 51 to 59 in the full length rat prothymosin α having the amino acid sequence shown in SEQ ID NO:9). P+2N/−2C is a peptide (peptide shown in SEQ ID NO:31) having the amino acid sequence from position 50 to 58 in the full length rat prothymosin α having the amino acid sequence shown in SEQ ID NO:9. P+3N/−3C is a peptide (peptide shown in SEQ ID NO:13) having the amino acid sequence from position 49 to 57 in the full length rat prothymosin α having the amino acid sequence shown in SEQ ID NO:9. P+1N/−3C is a peptide (Peptide P7 shown in SEQ ID NO:32) having the amino acid sequence from position 51 to 57 in the full length rat prothymosin α having the amino acid sequence shown in SEQ ID NO:9. P+1N/−4C is a peptide (Peptide P6: peptide shown in SEQ ID NO:1) having the amino acid sequence from position 51 to 56 in the full length rat prothymosin α having the amino acid sequence shown in SEQ ID NO:9. P+1N/−5C is a peptide having the amino acid sequence from position 51 to 55 in the full length rat prothymosin α having the amino acid sequence shown in SEQ ID NO:9.

Among these, P+1N/−1C (SEQ ID NO:30), P+2N/−2C (SEQ ID NO:31), P+1N/−3C (SEQ ID NO:32) and P+1N/−4C (SEQ ID NO:1) had a high protective action on retinal ischemic dysfunction.

Example 2

Inhibitory Effects of Peptides Derived from Prothymosin α on Retinal Dysfunction Induced by Retinal Ischemia The activity from photoirradiation to the optic nerve (ganglion cell) can be evaluated in ERG. The potential difference between the cornea and the posterior pole is +2 to 17 mV (the resting potential of the retina). After photic stimulation, an inward voltage change, a-wave, is generated at a latency of 15 msec, and subsequently, an outward voltage change, b-wave, is generated. The a-wave reflects the action of external granular layer (visual cell) and the b-wave reflects the function of from internal granular layer to ganglion cell layer. The a-wave and b-wave almost completely disappear at a week after ischemic treatment, and the electric potential becomes flat. The disappearance of a-wave and b-wave shows a decline in retinal function by retinal ischemic dysfunction. It is known that when 1 pmol prothymosin α, neuroprotective protein, (in a PBS solution) is injected into a vitreous body after 24 hours of ischemia, the inward and outward currents are almost completely recovered (Non Patent Literature 4 (Fujita et al., Cell Death and Differ, 2009)).

The effect of each prothymosin α-derived peptide (i.e., ProTα30 (a peptide comprising amino acids from position 49 to 78 in rat prothymosin α; SEQ ID NO:10), ProTα9 (a peptide comprising amino acids from position 52 to 60 in rat prothymosin α; SEQ ID NO:11), ProTα6 and a peptide in which the N-terminus of ProTα6 is acetylated and the C-terminus thereof is amidated (abbreviated as P30, P9, P6 and mP6, respectively)) on retinal ischemic dysfunction after ischemic treatment was measured using ERG (Electroretinogram). The ischemic treatment was carried out by applying a water pressure of 130 mmHg to the anterior chamber of mouse eyes for 45 minutes. The retinal potential was measured after a week of ischemic treatment. After a week of ischemic treatment, mice were dark-adapted for 3 hours. Thereafter, light was irradiated for a short time and changes in resting potential were measured using electrodes fitted on the cornea.

In this example, partial peptides of prothymosin α, P30 and P9 (Patent Literature 2), as well as P6 and a derivative of P6, mP6 (N-acetyl-P6-amide), were administered into a vitreous body after 24 hours of ischemia.

The results are shown in FIG. 3 (left figures: a-wave; right figures: b-wave). The ordinate indicates changes in voltage and the abscissa indicates the dosage (pmol) of each peptide. As can be seen from FIG. 3, P30 and P6 showed an almost equal and excellent inhibitory effect on retinal ischemic dysfunction in a concentration range of 1 to 10 pmol. The activity of P9 was weaker rather than that of P30 and P6 and an about 6-fold higher concentration was required to obtain an equal effect. Furthermore, mP6, a derivative in which the termini of Peptide P6 were modified, had a higher effect than P30 and P6, and showed an equal inhibitory effect on retinal ischemic dysfunction even in a 4-fold lower concentration than that of P6.

Example 3

Inhibitory Effects of P6 and Derivatives of P6 on an Increase in Activity of MMP Induced by Retinal Ischemia It is known that a tight junction protein, occluding, is degraded by metalloproteinases (MMP) whose expression is increased by ischemia (J Cereb Blood Flow Metab, 2007. 27(4): p. 697-709). It is believed that MMP-9, in particular, plays a primary role in a failure of a blood-organ barrier by ischemia (J Cereb Blood Flow Metab, 2000. 20(12): p. 1681-9).

The expression level of MMP-9 is commonly low and the expression is derived by various stimuli by ischemia. When the activity of MMP-9 was evaluated by gelatin zymography, the activity of proMMP-9 after 12 hours of retinal ischemia significantly increased, but when 10 pmol P6 was intravitreally administered after 3 hours of retinal ischemia, an increase in activity of proMMP-9 by ischemia was inhibited to about half.

Similarly, 10 pmol P6-NH$_2$, in which the C-terminus of P6 was amidated, also inhibited the activity of proMMP-9 to half or less. In addition, 1 pmol mP6, in which the N-terminus of P6 was acetylated and the C-terminus was amidated, showed an effect equal to that of P6.

Figure 4:
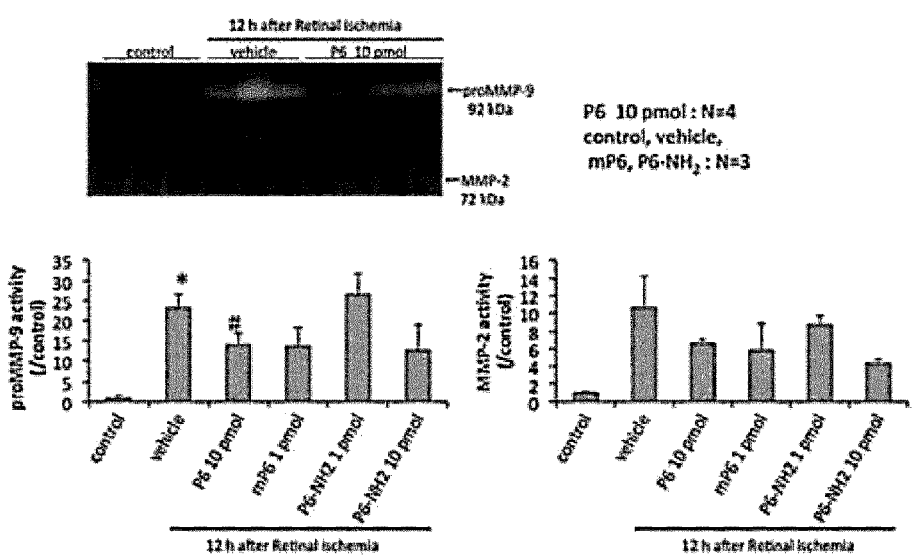
FIG. 4 shows figures showing the effects of P6 and P6 derivatives on an increase in activity of MMP after 12 hours of ischemia in a model of retinal ischemia. In the figure, * indicates P<0.05 vs control and # indicates P<0.05 vs Vehicle in the Student's t test.

MMP-2 is constantly expressed and the activity significantly increased by retinal ischemia. In reference to MMP-2, when a P6-derived peptide was administered, the activity was inhibited as is the case with proMMP-9 (FIG. 4).

Example 4

Effects of P30 and P6 in a Model Mouse of tMCAO (Transient Middle Cerebral Artery Occlusion) Ischemia The model mice of cerebral ischemia produced by left middle cerebral artery occlusion in C57BL/J6 mice were maintained for an hour, followed by reperfusion. P30 (1 mg/kg or 3 mg/kg) or P6 (1 mg/kg) was administered into the caudal vein after an hour of reperfusion. Thereafter, the course of the mice was observed every 24 hours to evaluate motor function and existence. The clinical scores showing motor dysfunction are evaluated using the following five grades: 1: unable to completely extend the right front limb, 2: clockwise circling behavior, 3: unable to hold the position and incline to the right, 4: disappearance of spontaneous movement, and 5: death.

In FIG. 5, the data indicated by white squire indicate values when 0.1% DMSO in PBS (vehicle) was administered into the caudal vein in an amount of 100 μl/10 g after an hour of tMCAO for an hour. When the mice were evaluated every day for 14 days, the almost maximum deterioration in clinical scores was shown after 6 days on average and almost all mice were died (n=9). Black circle and black rhombus in the upper graph indicate the results of 1 mg/kg and 3 mg/kg P30 intravenous (i.v.) administration, respectively, and black circle in the lower graph indicates the results of 1 mg/kg P6 intravenous (i.v.) administration.

As can be seen from FIG. 5, a significant protective effect was observed by 3 mg/kg P30 administration and the clinical score declined to approximately 2 on average. The protective effect was low by 1 mg/kg administration and the score was approximately 4 on average after 8 days. In contrast, the clinical score about P6 declines to approximately 2 on average even by 1 mg/kg, and it has been shown that P6 has a significant protective effect. The validity by 1 mg/kg P6 was almost equal to that by 3 mg/kg P30.

The upper row in FIG. 6 shows the results at 7 days after ischemia in FIG. 5 using a bar graph and the left graph in the lower row is a graph showing the cumulative clinical scores for 14 days as AUC (Area Under Curve).

The right graph in the lower row in FIG. 6 is a graph showing the cumulative clinical scores for 14 days as AUC when administration timing of P6 (1 mg/kg) was changed (after an hour, two hours and three hours of tMCAO for an hour). When P6 was administered after two hours, the protective effect is relatively lower than when administered after an hour, but the protective effect almost equal to that of P30 at the same concentration was shown (compared to the left graph in the lower row).

The state of tMCAO for an hour and after two hours of reperfusion corresponds to the state after three hours of the actual occurrence of cerebral stroke. That is, it can be said that even when P6 is administered after three hours after a fall due to cerebral stroke, a sufficient protective effect on cerebral stroke is displayed.

Example 5

Ameliorative Effect of Peptide P6 on Blood-brain Barrier Dysfunction

Cerebral ischemia by left middle cerebral artery occlusion in C57BL/J6 mice (male, body weight 21 to 26 g) was maintained for an hour, followed by reperfusion. Vehicle or P6 (0.1 mg/kg) was intravenously (i.v.) administered twice after 0.5 hours and 3 hours of reperfusion, and further a general anesthesia was given after 24 hours of reperfusion by intraperitoneal administration of 50 mg/kg pentobarbital. The treated mouse was statically placed on a bed kept at 37° C. and 100 μL of 1 mg/mL biotinylated tomato lectin (SIGMA, Lot No. 048K3786) dissolved in PBS was slowly intravenously administered over 2 to 3 minutes. After 5 minutes, systemic perfusion fixation was carried out using paraformaldehyde (PFA), and brain was taken off and treated with 4% PFA at room temperature for another 3 hours, and thereafter, put into a 25% sucrose solution and acclimatized at 4° C. overnight. The brain was frozen-embedded with OCT Compound and a slice in a thickness of 50 μm was produced from the surface containing the cerebral sensory area S1 (CS1) and S2 (CS2), and attached on a silane-coated slide glass and dried on a heater overnight. Thereafter, tomato lectin was fluorescently stained using Alexa Fluor 488-labeled streptavidin (300-fold diluted using a 2% BSA/PBST solution), and then fixed using Fluoromount (Japan Tanner Corporation), which is a fluorescence-fading inhibitor, and statically placed in a dark place overnight, and then observed by a confocal laser microscope LSM5 PASCAL (Carl Zeiss). As fluorescence signals, the total amount of fluorescence in a range of approximately 30 μm was integrated and analyzed by a deconvolution method.

Figure 7:
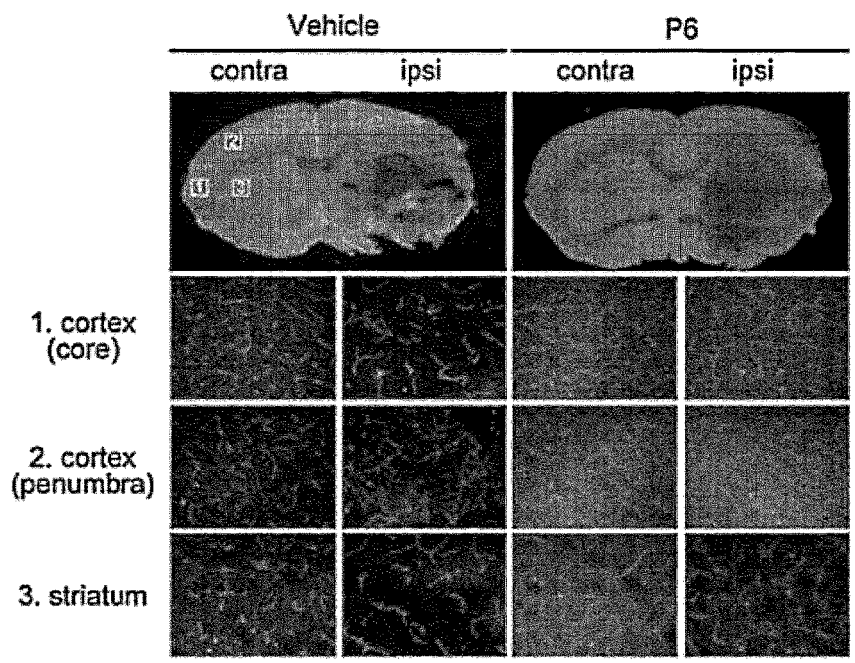
FIG. 7 shows figures of tomato lectin staining which show the inhibitory effect of Peptide P6 on blood-brain barrier dysfunction. The contra indicates the non-arterial infarction side and the ipsi indicates the arterial infarction side. The numbers 1 to 3 in the lower row correspond to 1 to 3 in the left figure in the upper row and indicate the cerebral cortex (ischemic core: core), the cerebral cortex (peri-ischemia: penumbra) and the corpus striatum, respectively.

When the whole slice was observed, tissue damage in the P6 administered group was slight as compared to that in the control group (Vehicle) (the right and left in the upper row in FIG. 7). About the portions indicated by the numbers 1 to 3 on the contra side (contralateral) (i.e., non arterial infarction side) and the portions 1 to 3 on the ipsi side (ipsilateral) (i.e., arterial infarction side) corresponding thereto in the photographs in the upper row, each enlarged figure is shown thereunder.

In the mice in the control group, vessel density decreased in the ipse as compared to the contra in the ischemic core (core) of the cerebral cortex and the corpus striatum (striatum) region, but in the P6 administered group, the improvement of vessel density in both the core and the striatum was observed, and the fluorescence results were obtained even in the ipsi in the same degree as in the contra. An action to protect vessels in the striatum was particularly remarkable.

Example 6

Inhibitory Effect of P6 on tPA-Induced Motor Dysfunction

Figure 8:
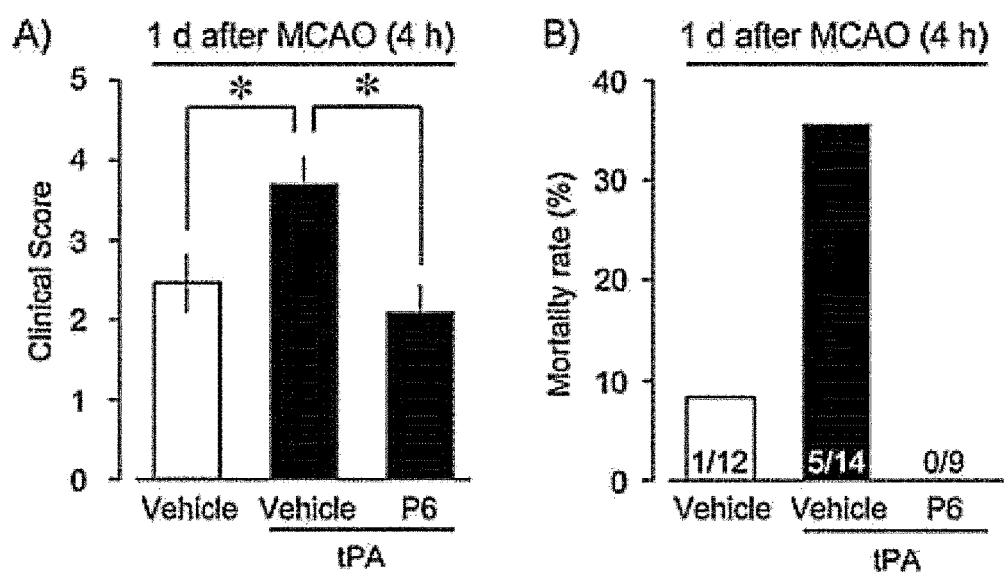
FIG. 8, the left figure, is a figure showing the combined effect of P6 with tPA on clinical scores after a day of MCAO for four hours. Vehicle, 10 mg/kg tPA and tPA+1 mg/kg P6 were administered to the caudal vein immediately before reperfusion. In the figure, * indicates P<0.05 in the Student's t test. The right figure in FIG. 8 is a figure showing the combined effect of P6 with tPA on mortality rate after a day of MCAO for four hours.

After tMCAO for four hours, the clinical score and mortality rate were evaluated after a day (FIG. 8). Immediately before reperfusion, Vehicle, 10 mg/kg tPA and tPA+P6 1 mg/kg were administered into the caudal vein. The tMCAO for four hours corresponds to the state after 3 hours from the onset of ischemic diseases. Motor dysfunction deteriorated by tPA treatment as compared to the vehicle group, but was significantly inhibited by using tPA and P6 in combination (the left graph).

As a result of the evaluation of mortality rate after a day of ischemia, only 8.3% of death was observed in the vehicle administered group, while 35.7% of death was observed in the tPA administered group. However, all mice existed by using tPA and P6 in combination.

Example 7

Therapeutic Agent for Cerebral Infarction

Peptides comprising the amino acid sequence shown in SEQ ID NO:1 or the amino acid sequence shown in SEQ ID NO:1 in which one or two amino acids are deleted, added, substituted and/or inserted, or salts thereof were synthesized by a known method. The obtained peptides were 22 types. Peptides comprising the amino acid sequences shown in SEQ ID NOs:1 to 6 and salts thereof were contained in the 22 types of peptides. From Kyowa Hakko Kirin Co., Ltd. (Tokyo, Japan), tPA was purchased. The peptides comprising the amino acid sequences shown in SEQ ID NOs:1 to 6 and salts thereof were regarded as P6, Peptide A, Peptide B, Peptide C, Peptide D and Peptide E, respectively.

Animal Experiment

The 6 to 9-week-old C57/BL6J male mice (19 to 28 g) used in the present experiment were raised in a room at a constant temperature (22±2° C.) under the control of natural environment, day and night every 12 hours, and tap water and solid feed for ordinary animals (MF, Oriental Yeast Co., Ltd., Tokyo, Japan) were taken ad libitum. All experiments given below were carried out according to methods prescribed in the guideline on animal experiments of NAGASAKI UNIVERSITY.

Model of Retinal Ischemia

To apply anesthesia, 75 mg/kg pentobarbital was intraperitoneally administered to mice. The mice were placed on a constant-temperature table at 37° C. to maintain body temperature. In the vitreous body, mydriasis was induced using 1% atropine sulfate. A container for an aseptic intraocular irrigating solution (BSS PLUS dilution buffer; Alcon, Fort Worth, Tex., USA) was preliminary lifted so that the surface of the water would be a height of 135.5 cm (100 mmHg) from the eyes of the mice, and a 33G injection needle connected to a transfusion set for children was inserted into the anterior chamber of eyes for fixation with the irrigating solution slightly poured from the needle point. After inserting the needle into the anterior chamber, pressure (100 mmHg) was applied into the anterior chamber of eyes for 45 minutes by releasing the perfusion system (the normal intraocular pressure of mouse is approximately 15 mmHg). These operations were carried out under a stereoscopic microscope and it was confirmed by visual observation using an interruption of intraretinal blood flow as an index that renal ischemia was elicited by an intraocular pressure increase. After the conclusion of ischemic stress, the injection needle was pulled off, and the retina was reperfused by decreasing intraocular pressure. The model is a general glaucoma model using an ischemia-reperfusion method, and it is known that neuroprotective effects are shown by systemic administration of an angiotensin converting enzyme inhibitor, which is an existing therapeutic drug for glaucoma, and the like.

Evaluation of Tissue Damage by Hematoxylin-Eosin (HE) Staining

Production of samples: to apply anesthesia, 50 mg/kg pentobarbital was intraperitoneally administered to mice. From heart, 40 ml of K+ free PBS was perfused to remove blood and 30 ml of 4% PFA was perfused for fixation. An eyeball was removed from a mouse and immersion fixation was carried out with 4% PFA at room temperature for 3 hours, followed by replacement with 25% sucrose, and incubation was carried out at 4° C. for 8 hours or more until tissue was submerged. Thereafter, water on the surface of tissue was wiped off, followed by embedding with OCT Compound. A slice in a thickness of 10 μm was created by freezing microtome, CM1900, and attached to a silane-coated slide glass, and dried in a heater overnight.

HE staining: the cell nucleus of a specimen was stained with Gill's hematoxylin solution, and after washing, and separation was carried out with 0.2% hydrochloric acid-70% ethanol. The separation solution was washed and the specimen was combined with 95% ethanol. The tissue was counterstained with an eosin-phloxine solution. Separation and dehydration were carried out with ethanol, and the tissue was cleared with xylene. The specimen was enclosed and then observed by BIOZERO Microscope (KEYENCE, Osaka, Japan).

Evaluation of Retinal Function by Electroretinogram (ERG)

Mice were dark-adapted in a dark room for 3 hours, and 50 mg/kg pentobarbital was then intraperitoneally administered to the mice to apply anesthesia. Their pupils were dilated using a 1% atropine collyrium, and a contact electrode (KE-S; Kyoto contact lenses, Kyoto, Japan) was then placed on the corneal apex and an iron electrode was placed near the eye. A subcutaneous platinum needle electrode was placed in the abdominal region. ERG was induced by a 20 J flash using SLS-3100 (NIHON KOHDEN CORPORATION, Tokyo, Japan) and measured by MEB-9104 (NIHON KOHDEN CORPORATION) every two minutes for 30 minutes. For background correction, results in which reactions in the light time under normal conditions were measured every two minutes for 20 minutes were used. The amplification of a-wave and b-wave to be measured was determined by Neuropack (NIHON KOHDEN CORPORATION).

Model of Transient Middle Cerebral Artery Occlusion (tMCAO)

Mice were anesthetized with 3% isoflurane (Escain (registered trademark), Mylan Seiyaku Ltd., Tokyo, Japan) (Small animal anesthetizer MK-A100, Muromachi Kikai Co., Ltd., Tokyo, Japan). On a constant-temperature table at 37° C. (Ikemoto Scientific Technology Co., Ltd., Tokyo, Japan), the skin in the pharyngeal region is cut lengthwise into about 2 cm with scissors. The skin was drawn to the right using a hard silk thread (hard No. 8, Natsume Seisakusho Co., Ltd.) to secure a visual field. Using a stereoscopic microscope, the left common carotid artery which is located on the left side of the trachea is secured with a hard silk thread while exfoliating connective tissue, nerves and the like. By following the common carotid artery upward, the artery is separated into the internal carotid artery and the external carotid artery, and the external carotid artery on the left near side is tightly tied at two points with a soft silk thread and the space between the points is cut. A thin vessel extending upward from the internal carotid artery is secured with a soft silk thread. The soft silk thread and hard silk thread are strongly drawn to stop blood flow and an incision is made in the internal carotid artery with scissors. From that, an obturator is inserted 1 to 1.5 cm and the middle cerebral artery is occluded. The internal carotid artery was tied together with the obturator using a soft silk thread to fix the obturator. A soft silk thread is passed under the hard silk thread drawing and the common carotid artery is tied thereby on the near side of the hard silk thread, and the hard silk thread is then removed. The breath is sutured at two points with a soft silk thread. In the case of the model of transient middle cerebral artery occlusion (tMCAO) of the present problem, anesthesia was applied to the mice with 3% isoflurane again after an hour or 4 hours on a constant-temperature table at 37° C., and the soft silk thread suturing the breath is untied to open the breath. The soft silk thread tying the internal carotid artery was loosened and the obturator was withdrawn, and the internal carotid artery was immediately tied again.

Thrombotic Cerebral Infarction (Photochemically-Induced Thrombosis: PIT) Model

Mice were anesthetized with 3% isoflurane (Escain (registered trademark), Mylan Seiyaku Ltd., Tokyo, Japan) (Small animal anesthetizer MK-A100, Muromachi Kikai Co., Ltd., Tokyo, Japan). During the operation, the anesthetic effect was maintained with 2.5% isoflurane. On a constant-temperature table at 37° C. (Ikemoto Scientific Technology Co., Ltd., Tokyo, Japan), the skin between the left ear and the left eye was incised 5 to 6 mm. The ophthalmic scissors were put along the edge of the temporal muscle and the attachment site between the cranial bone and the temporal muscle was incised to expose the cranial bone in the region of the middle cerebral artery under the temporal muscle. The skin and temporal muscle were drawn in four directions with a soft silk thread to secure a visual field, and a small hole with a diameter of approximately 1.5 mm was then opened by a drill in the cranial bone in the region of the middle cerebral artery under a stereoscopic microscope. To the caudal vein, 30 mg/kg rose bengal (Wako) was administered, and immediately after that, the tip of the light guide (A4888; Hamamatsu Photonics K.K., Shizuoka, Japan) connected to a UV spot light source (L-4887-13; Hamamatsu Photonics K.K., Shizuoka, Japan) was perpendicularly put on the distal middle cerebral artery confirmed under the dura mater and green light was irradiated for 10 minutes. Thereafter, changes in the middle cerebral artery (getting thinner or blood red becomes lighter) were confirmed and the temporal muscle was then put back, and the skin was sutured with a soft silk thread.

Neurological Scoring

To evaluate the degree of motor function disorders associated with cerebral ischemia, the neurological scores (Clinical Scores) according to the following definition were used. In addition, two grade evaluation was carried out using numerical values 1 to 4 (when scores 1 and 2 were shown, 1.5 was used).

1: motor function disorders of the right front limb, 2: one-directional behavior, 3: unable to hold the position and incline, 4: disappearance of spontaneous movement, and 5: death.

Evaluation of Cerebral Infarction Region by TTC Staining

PBS (phosphate-buffered saline) was poured into a beaker so that a whole brain would be soaked, and dispensed into a 24 well plate in an amount of 500 µL/well, and cooled with ice. A solution of 2% TTC (2,3,5-triphenyltetrazolium chloride) is created. Brain tissue is removed and washed with PBS cooled with ice in the beaker. The brain tissue is placed on a brain slicer (Muromachi Kikai Co., Ltd., Tokyo, Japan) preliminarily cooled with ice, and 6 brain slices of the coronal section having a thickness of 1 mm are created using a razor. The range of the created brain slices is a place of 2 mm forward and 3 mm backward from bregma. Each one of the brain slices is quickly soaked in PBS cooled with ice in the 24 well plate and PBS was replaced with a 2% TTC solution. Thereafter, light was shaded and the slices were incubated at room temperature for 15 to 20 minutes and then fixed with 4% PFA, and observed.

Statistical Processing

A significant test between two individual groups was carried out using the Student's t-test after an analysis of variance by the F-test. In a multigroup analysis, a significant test was carried out using the Dunnett's test after an analysis of variance by One-factor ANOVA, repeated measure ANOVA.

Evaluation in a Model of Retinal Ischemia and Screening of Active Peptides

As evaluation by intravitreal administration treatment in a model of retinal ischemia, a histochemical analysis, which measures the thickness of a retina because of an intraocular part, a closed system, and a functional analysis by an electroretinogram (ERG) have high reproducibility and high sensitivity. Because of this, people responsible for the research regarded the present model, which is actually an in vivo analysis, as an in vitro analogous analysis, and searched an active domain based on the amino acid sequence of prothymosin α and succeeded in narrowing down to 6 amino acids (basic peptide P6).

Protective Effect of Basic Peptide P6

Figure 9:
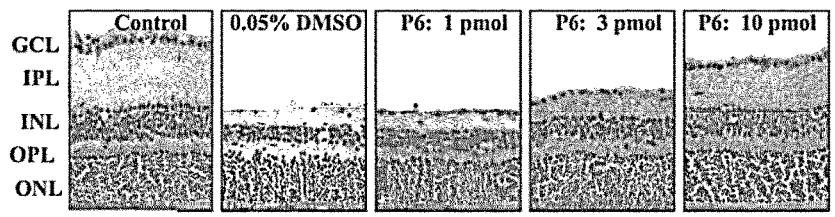
FIG. 9 shows photographs substituted for drawings, which show stained retinae to show the protective effect of basic peptide P6 on retinal ischemic dysfunction.
Figure 10A:
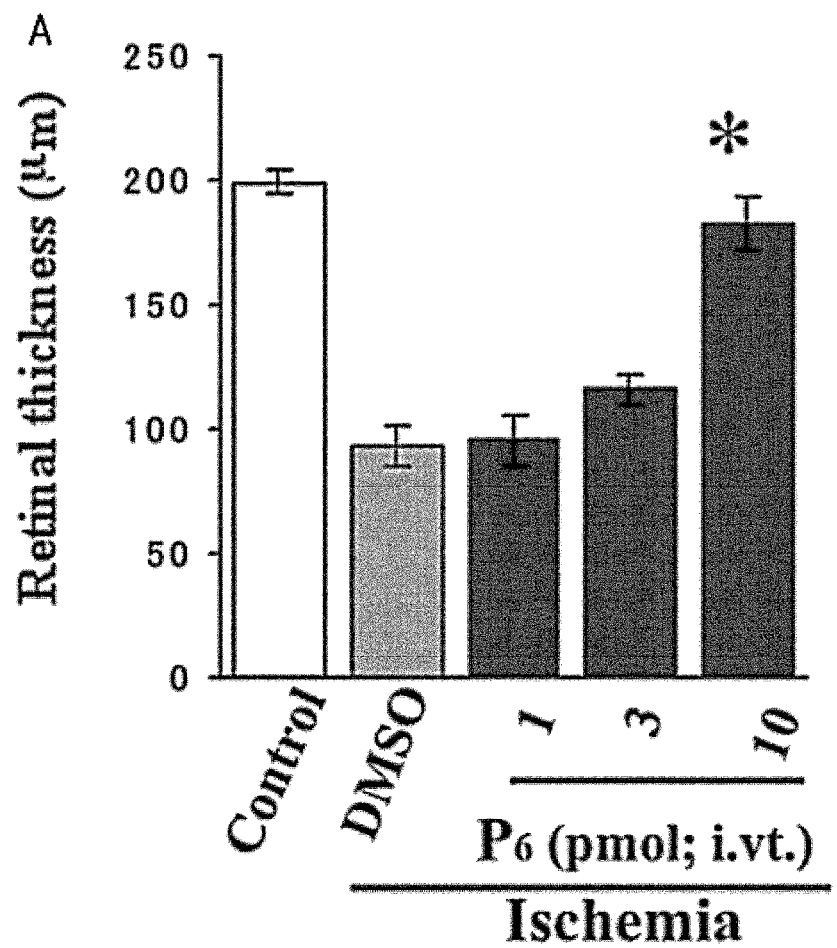
FIGS. 10A to 10C are figures of retinal thickness and retinal potential in the cases of control, DMSO administration and 1 pmol, 3 pmol and 10 pmol per eye P6 administration.
Figure 10B:
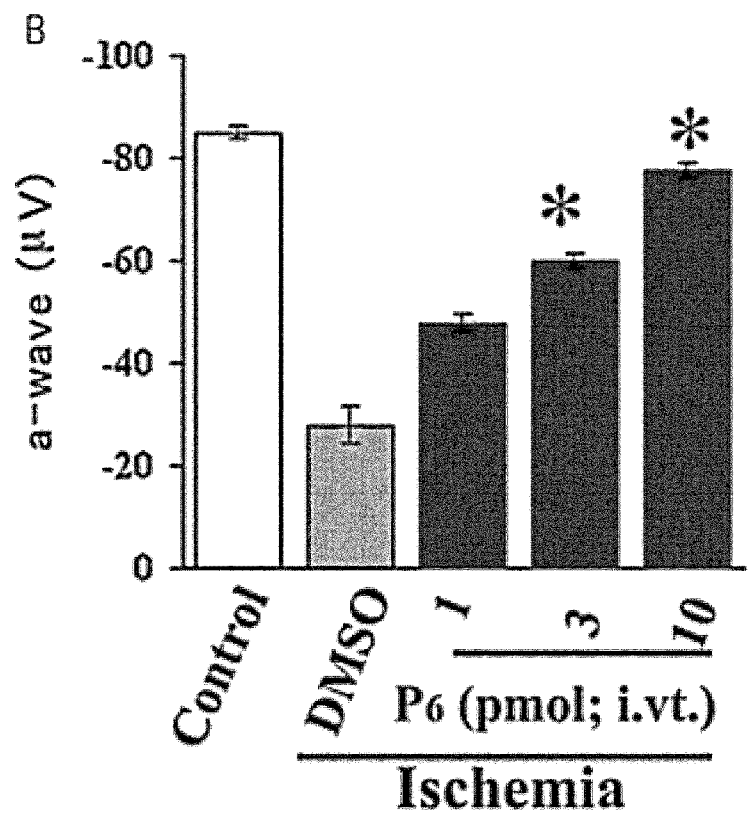
Figure 10C:
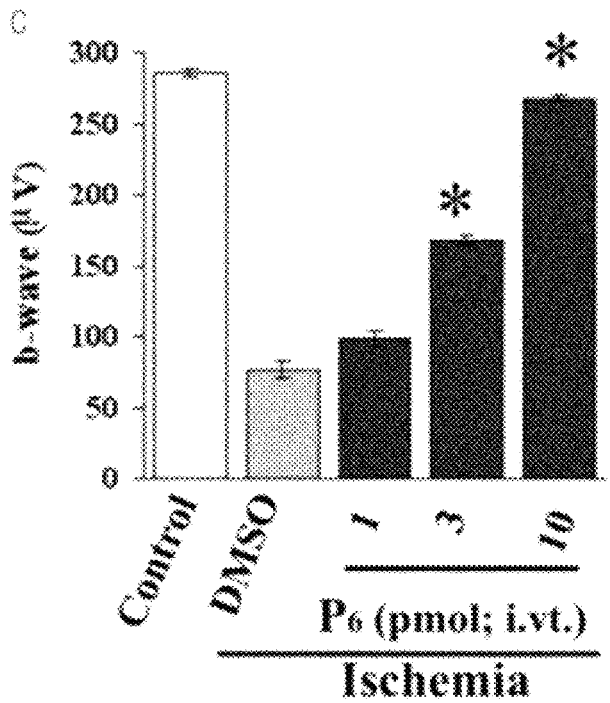

FIG. 9 are photographs substituted for drawings, which show stained retinae to show the protective effect of basic peptide P6 on retinal ischemic dysfunction. FIGS. 10A to 10C are figures of retinal thickness and retinal potential in the cases of control, DMSO administration and 1 pmol, 3 pmol and 10 pmol per eye P6 administration. FIG. 10A is a graph showing retinal thickness. FIG. 10B is a graph showing retinal potential values using a-wave. FIG. 10C is a graph showing retinal potential values using b-wave. From FIG. 9, for example, when P6 was administered in an amount of 3 pmol/eye or more, tissue damage was inhibited in a model of retinal ischemia, which shows P6 has an action to protect tissue. It should be noted that in the model of retinal ischemia, basic peptide P6 (NEVDEE) almost completely inhibited tissue damage by an intravitreal administration of 10 pmol/eye. In the functional analysis by ERG, it was revealed that a dose-dependently protective effect was shown from 3 pmol/eye (FIGS. 9 to 10C).

Screening of Active Peptides

Figure 11A:
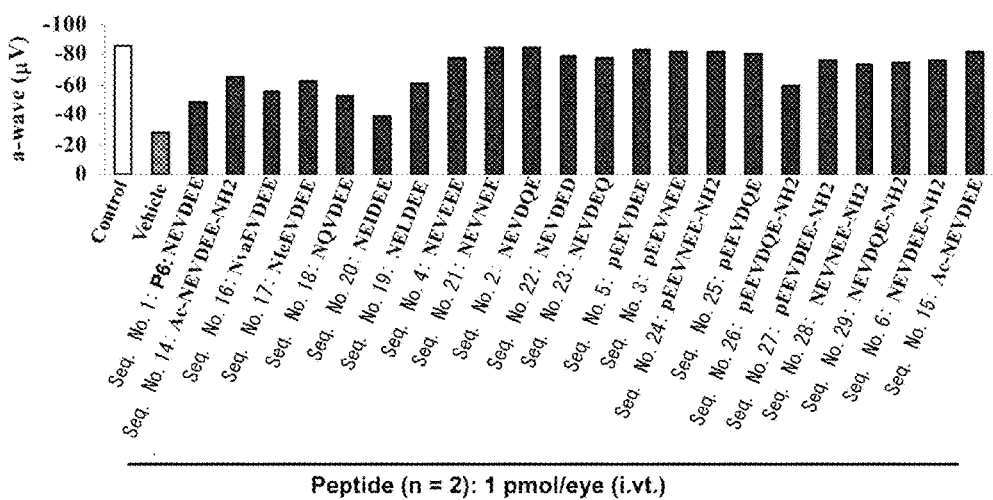
FIGS. 11A and 11B are graphs showing retinal potential values in the case of the administration of various peptides.
Figure 11B:
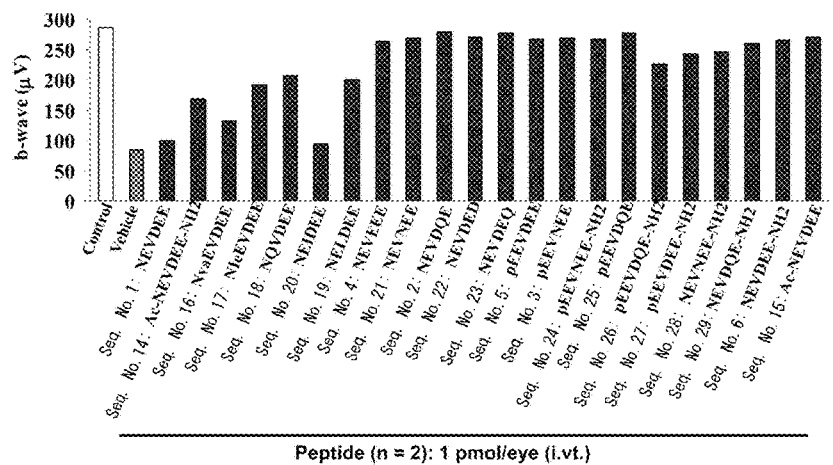

Based on the amino acid sequence of P6, 21 samples of modified peptides for screening such as amino acid-altered forms, acetylation of the N-terminus and amidation of the C-terminus were produced and evaluated by an ERG analysis in a model of retinal ischemia. As a target value, 1 pmol/eye which has an activity ten times higher than that of P6 was set, and by screening using this dose, 14 samples showed a higher activity than that of P6, which were considered as positive (FIGS. 11A and 11B). FIGS. 11A and 11B are graphs showing retinal potential values in the case of the administration of various peptides. FIG. 11A is a graph showing retinal potential values using a-wave. The peptides underlined in the figure are the derivatives of basic peptide P6, Peptide F, H, I, J, L, K, C, M, A, N, O, D, B, P, Q, R, S, T, U, E and G, respectively from the left. FIG. 11B is a graph showing retinal potential values using b-wave.

Selection of Highly Active Peptides

Figure 12A:
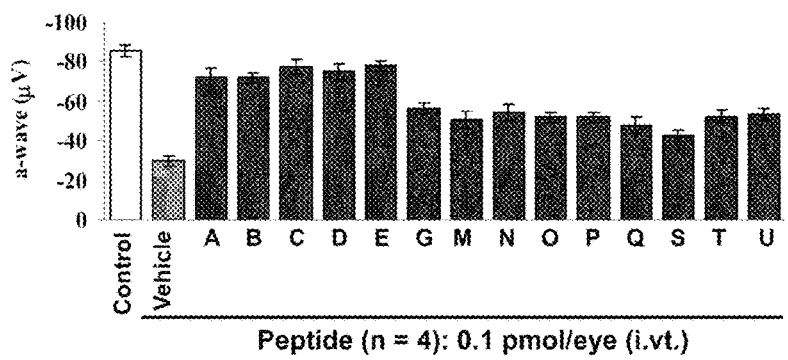
FIGS. 12A and 12B are graphs showing retinal potential values in the case of the administration of various peptides.
Figure 12B:
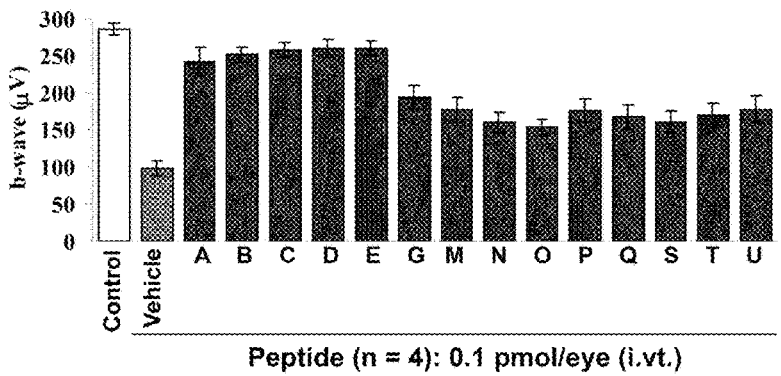

In order to select more highly active peptides from the positive peptides, a protective effect by a dose of 0.1 pmol/eye was evaluated by a functional analysis by ERG (FIGS. 12A and 12B). FIGS. 12A and 12B are graphs showing retinal potential values in the case of the administration of various peptides. In the figures, 1 to 14 correspond to the derivatives of basic peptide P6, Peptide (C, M, A, N, O, B, P, Q, E, G, U, D, T and S), respectively. FIG. 12A is a graph showing retinal potential values using a-wave. FIG. 12B is a graph showing retinal potential values using b-wave.

FIGS. 12A and 12B show that 5 samples of 14 samples have an almost complete protective activity by 0.1 pmol per eye administration. The protective effect by this dosage is significantly high as compared to that of prothymosin α.

These 5 types of highly active peptides were regarded as the highest priority peptides in the following analyses for a model of cerebral ischemia.

The sequence and modification of Peptides A to D in FIGS. 12A and 12B are simple as compared to those of P6. These sequences are shown in Table 1. In Peptide B and Peptide D, the N-terminus is phosphorylated, and in Peptide E, the C-terminus is amidated.

TABLE 1

| SEQUENCES AND MODIFICATION OF HIGHLY ACTIVE PROTOTYPE PEPTIDES | | |
|---|---|---|
| PEPTIDE NAME | PEPTIDE SEQUENCE | SEQUENCE NUMBER |
| BASIC PEPTIDE: P6 | NEVDEE | SEQ ID NO: 1 |
| PEPTIDE A | NEVDQE | SEQ ID NO: 2 |
| PEPTIDE B | pEEVNEE | SEQ ID NO: 3 |
| PEPTIDE C | NEVEEE | SEQ ID NO: 4 |
| PEPTIDE D | pEEVDEE | SEQ ID NO: 5 |
| PEPTIDE E | NEVDEE-NH$_2$ | SEQ ID NO: 6 |

Example 8

Evaluation in a tMCAO Model

Protective Effect of Basic Peptide P6 Activity on Motor Dysfunction

Figure 13A:
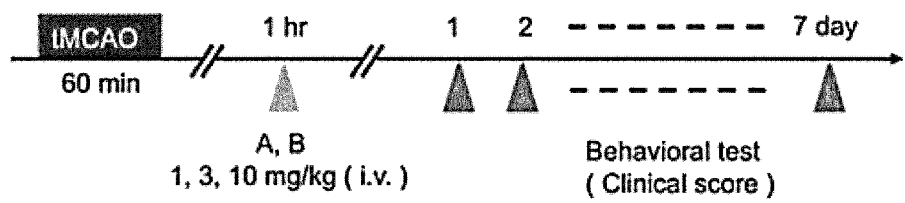
FIG. 13A shows the evaluation process in a tMCAO model.
Figure 13B:
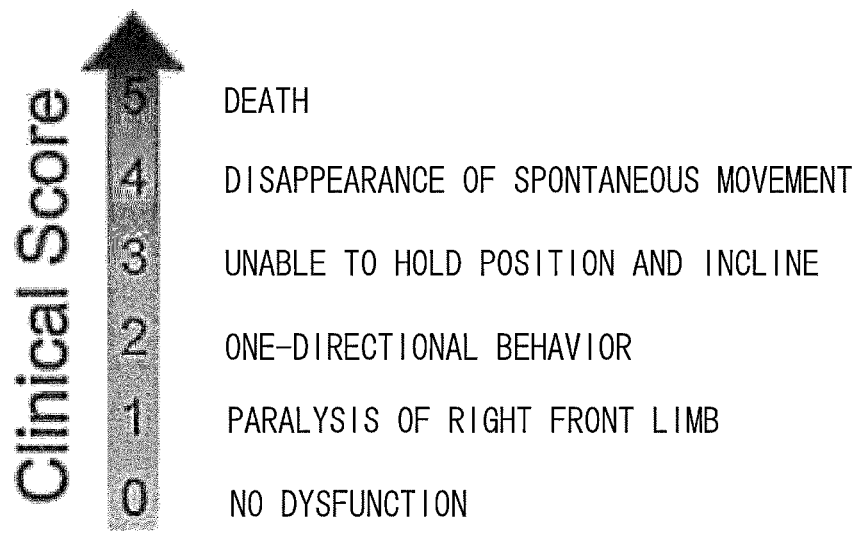
FIG. 13B shows the evaluation scores.
Figure 13:
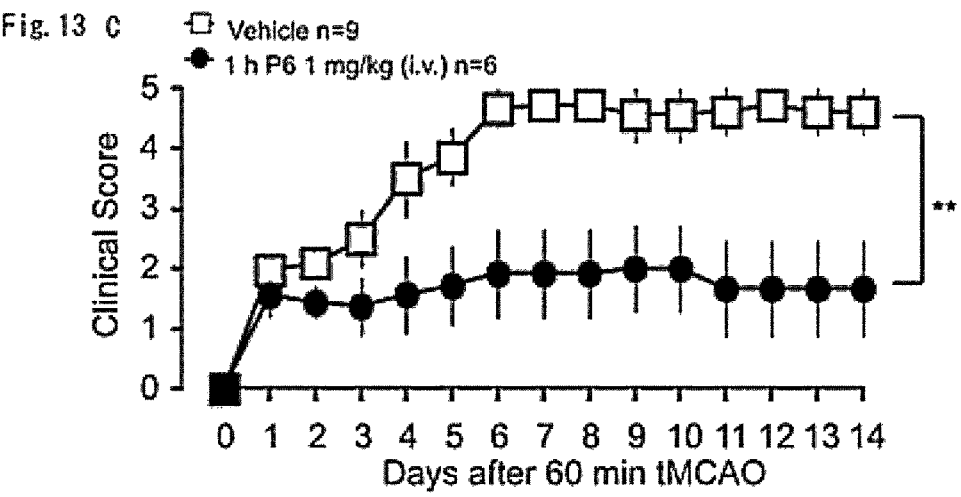
FIG. 13C shows changes in evaluation scores after tMCAO for 60 minutes.
FIG. 13D shows the scores when motor dysfunction for a day to 14 days was evaluated in control and each sample, in which 1 mg/kg P6 was administered after 1, 2 or 3 hours after tMCAO for an hour.
Figure 13D:
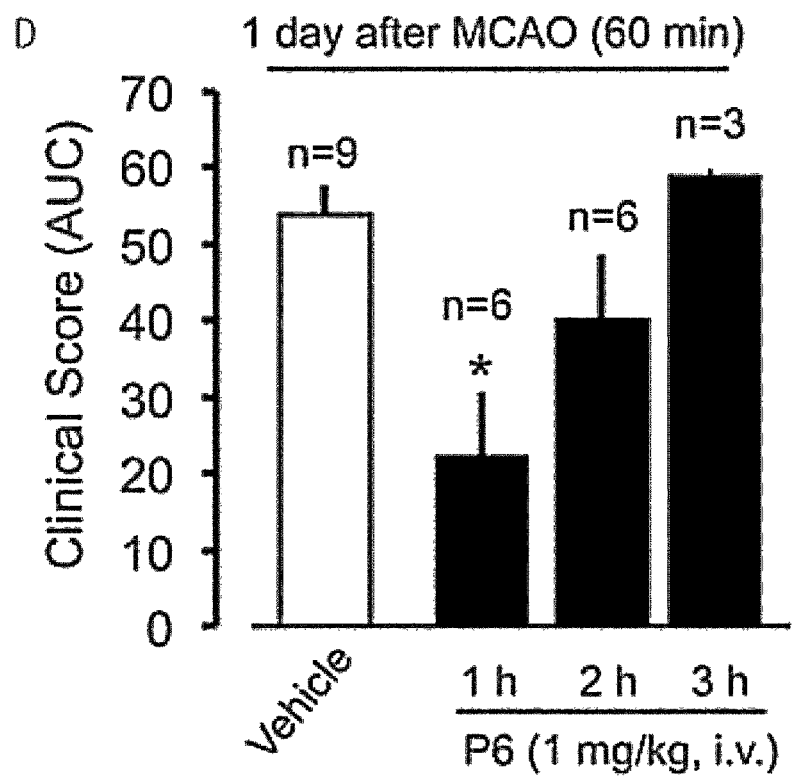

P6 was evaluated to have a protective effect on motor dysfunction by intravenous administration after an hour of ischemia, which corresponds to the hyperacute phase, in a tMCAO model (60 min ischemia). FIG. 13A shows the evaluation process in a tMCAO model. FIG. 13B shows the evaluation scores. FIG. 13C shows changes in evaluation scores after tMCAO for 60 minutes. FIG. 13D shows the scores when motor dysfunction for a day to 14 days was evaluated in control and each sample, in which 1 mg/kg P6 was administered after 1, 2 or 3 hours after tMCAO for an hour. The case when 1 mg/kg P6 was administered, for example, was confirmed to have a protective effect on motor dysfunction by intravenous administration after an hour of ischemia (FIGS. 13A to 13D).

Consequently, P6 was confirmed to have an obvious ameliorative action on motor dysfunction by 1 mg/kg administration after an hour of ischemia for an hour.

Protective Effects of Active Peptides on Motor Dysfunction

Figure 14:
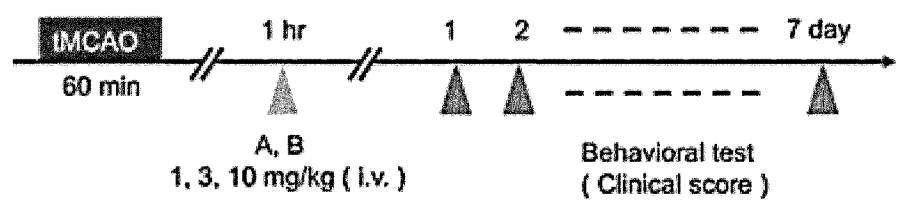
FIG. 14A shows the evaluation process in a tMCAO model.
FIG. 14B shows changes in evaluation scores of motor dysfunction in the tMCAO model when Peptide A is intravenously administered.
FIG. 14C shows changes in evaluation scores of motor dysfunction in the tMCAO model when Peptide B is intravenously administered.
Figure 14:
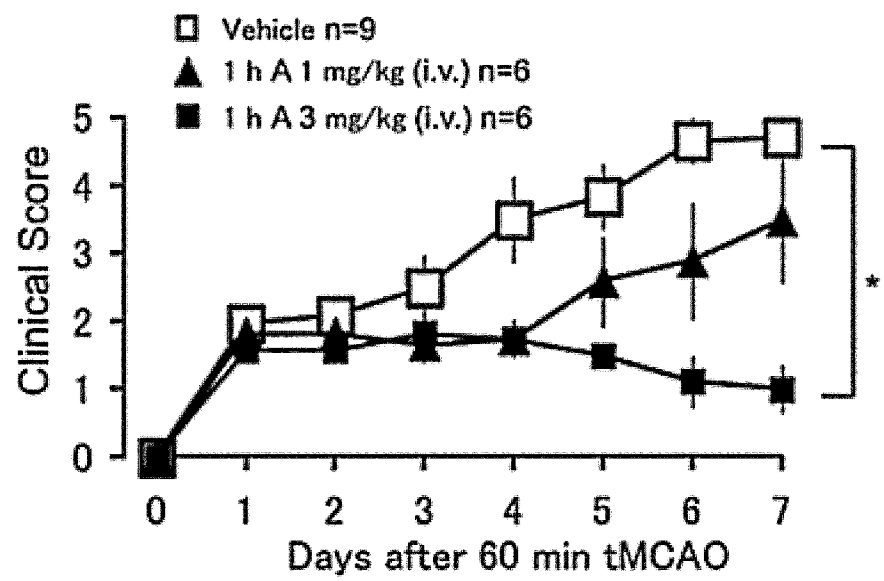
Figure 14:
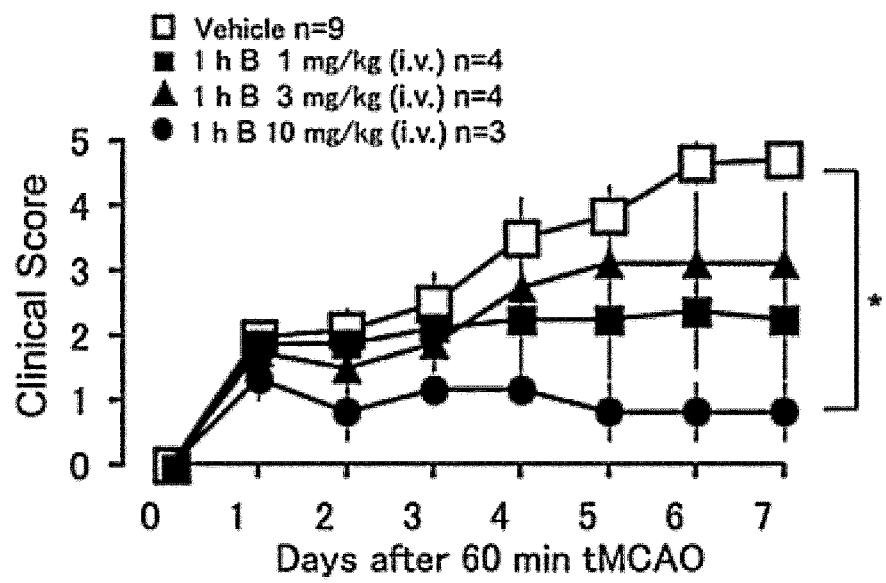

In the evaluation of highly active prototype peptides, a decrease in an effective dose or expansion of the effective concentration range (dose-dependency) was evaluated. FIG. 14A shows the evaluation process in a tMCAO model. FIG. 14B shows changes in evaluation scores of motor dysfunction in the tMCAO model when Peptide A is intravenously administered. FIG. 14C shows changes in evaluation scores of motor dysfunction in the tMCAO model when Peptide B is intravenously administered. Peptide A and Peptide B showed a dose-dependently protective effect on motor dysfunction by treatment after an hour after ischemia (1 to 10 mg/kg).

FIG. 14B showed that Peptide A showed the greatest protective effect by 3 mg/kg. On the other hand, FIG. 14C showed that Peptide B had the greatest protective effect by 10 mg/kg. Peptide C, Peptide D and Peptide E were also examined to have a protective action on motor dysfunction in the same manner. The results showed that the protective action of these peptides on motor dysfunction was not as good as that of Peptide A and Peptide B.

Figure 15A:
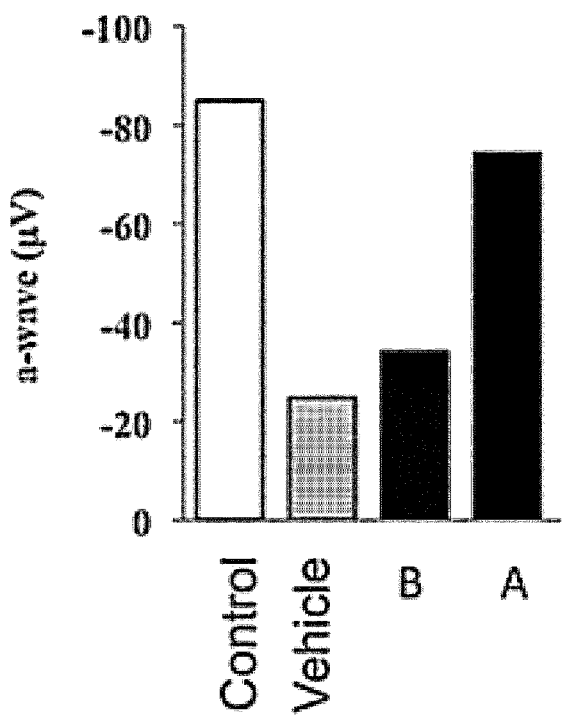
FIGS. 15A and 15B are graphs showing the results of ERG functional analysis.

Peptide A to Peptide E having a high activity in retinal ischemia were roughly classified into Peptide A and Peptide B having a high protective activity and Peptides C to E not having a high protective activity in cerebral ischemia. Furthermore, an activity difference between Peptide A and Peptide B was recognized, and thus this difference was expected to be a difference in administration methods, intravitreal administration and intravenous administration, and the protective effects of Peptide A and Peptide B by intravenous administration were examined in retinal ischemia (FIGS. 15A and 15B). FIGS. 15A and 15B are graphs showing the results of ERG functional analysis.

Figure 15:
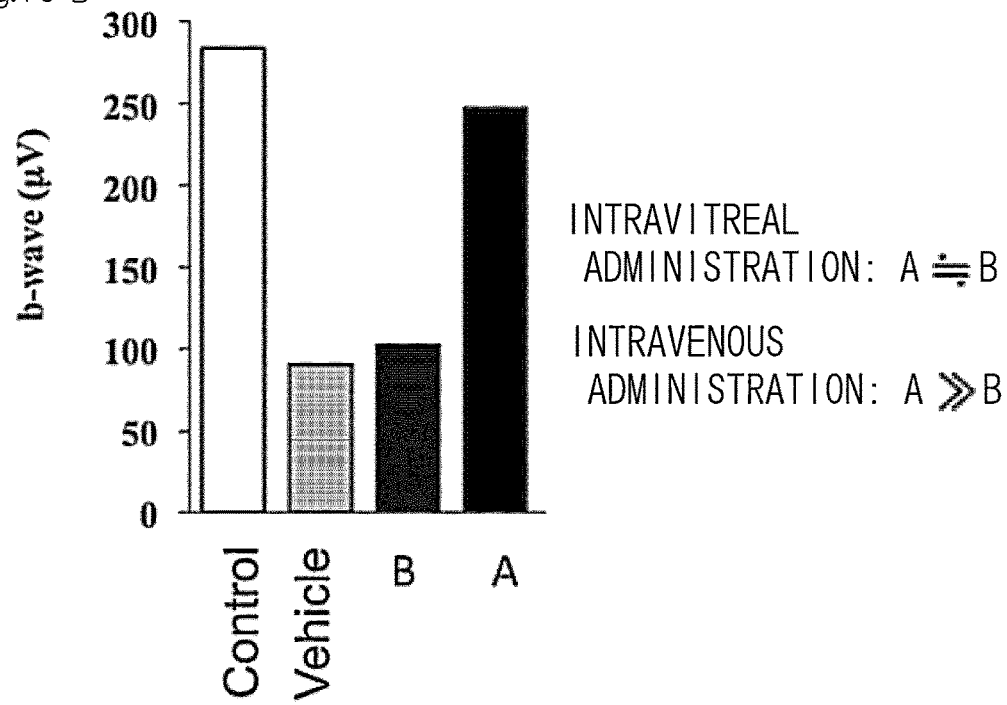

FIG. 15A is a graph showing retinal potential values using a-wave when 10 mg/kg Peptide A or Peptide B is intravenously administered 24 hours after retinal ischemia. FIG. 15B is a graph showing retinal potential values using b-wave when 10 mg/kg Peptide A or Peptide B is intravenously administered 24 hours after retinal ischemia. From FIGS. 15 A and 15B, it was revealed that when evaluating by ERG functional analyses, Peptide A had a high activity as expected.

Example 9

Side Effects of tPA: Inhibitory Effects of Active Peptides on Cerebral Hemorrhage Next, the attention was focused on the effect of P6 on vascular systems. A thrombolytic agent, tPA, used as a therapeutic agent for cerebral infarction is useful because it disappears infarction itself in treatment in the acute phase. However, tPA elicits cerebral hemorrhage as side effects, and thus image diagnosis is required when tPA is administered, and further is required to be administered within 3 hours after ischemia. Accordingly, the presence or absence of inhibitory effects on tPA-induced side effects was analyzed about P6 and 5 samples of Peptides (A-E). With the aim of significantly inducing cerebral hemorrhage by tPA, a system in which 10 mg/kg tPA is treated after treatment of ischemia for 4 hours and reperfusion is carried out was used.

Figure 16A:
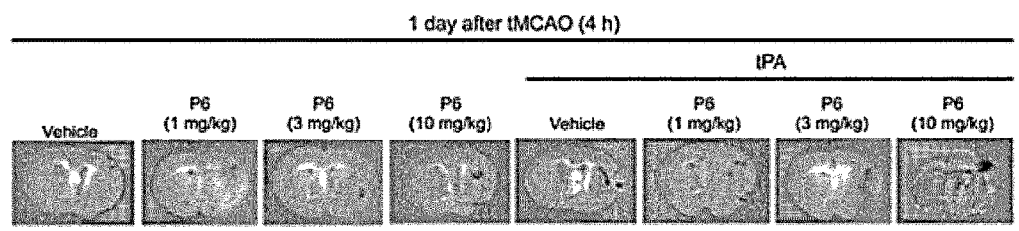
FIG. 16A shows photographs showing hemorrhagic action in the cerebral cortex and corpus striatum when P6 is used alone, or P6 and tPA is used in combination after 4 hours of tMCAO ischemia.
Figure 16B:
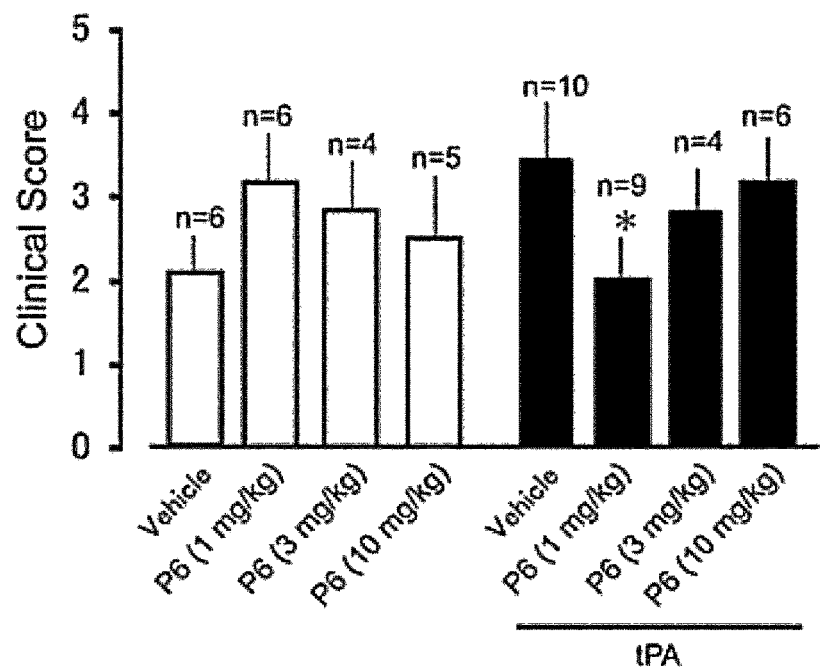
FIG. 16B shows a quantitative analysis of evaluation scores (Clinical Score) of motor dysfunction at 24 hours after ischemia when P6 is used alone, or P6 and tPA is used in combination after 4 hours of tMCAO ischemia.
Figure 16C:
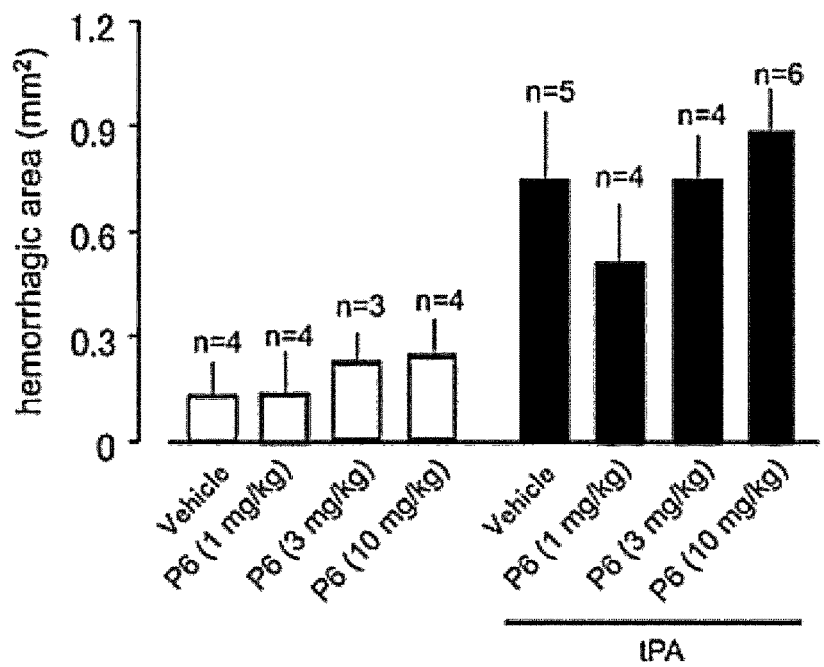
FIG. 16C shows a quantitative analysis of hemorrhagic action in the cerebral cortex and corpus striatum when P6 is used alone, or P6 and tPA is used in combination after 4 hours of tMCAO ischemia.

FIG. 16A shows photographs showing hemorrhagic action in the cerebral cortex and corpus striatum when P6 is used alone, or P6 and tPA are used in combination after 4 hours of MCAO ischemia. FIG. 16A shows photographs in the cases of control, P6 1 mg/kg administration, 3 mg/kg administration and 10 mg/kg administration, tPA-alone (control), tPA and P6 1 mg/kg administration, 3 mg/kg administration and 10 mg/kg administration. FIGS. 16B and 16C are graphs showing diverse activities of 5 samples of prototype peptides by combined use with tPA. FIG. 16B shows a quantitative analysis of evaluation scores (Clinical Score) of motor dysfunction at 24 hours after ischemia when P6 is used alone, or P6 and tPA are used in combination after 4 hours of tMCAO ischemia. FIG. 16B shows the scores in the cases of control (vehicle), 1, 3 and 10 mg/kg P6 administration, tPA-alone control, and coadministration of tPA and 1, 3 and 10 mg/kg P6. FIG. 16C shows a quantitative analysis of hemorrhagic action in the cerebral cortex and corpus striatum when P6 is used alone, or P6 and tPA is used in combination after 4 hours of tMCAO ischemia. FIG. 16C shows the scores in the cases of control, 1, 3 and 10 mg/kg P6 administration, tPA-alone control, and coadministration of tPA and 1, 3 and 10 mg/kg P6. From FIG. 16C, exacerbation of motor dysfunction and cerebral hemorrhage induced by tPA were inhibited by combined use with 1 mg/kg P6, but when a dose was increased, the inhibitory effect decreased concentration-dependently.

Example 10

Figure 17A:
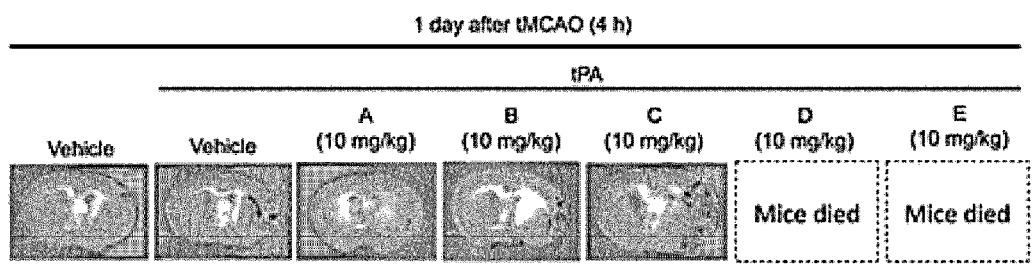
FIG. 17A shows photographs showing hemorrhagic action in the cerebral cortex and corpus striatum when Peptides A, B, C, D and E are used alone, or each peptide and tPA are used in combination after 4 hours of tMCAO ischemia.

Based on the results of P6, it was analyzed whether or not 5 samples of prototype peptides (Peptides A to E) inhibited the side effects of tPA by 10 mg/kg administration. FIG. 17A shows photographs showing hemorrhagic action in the cerebral cortex and corpus striatum when Peptides A, B, C, D and E are used alone, or each peptide and tPA are used in combination after 4 hours of tMCAO ischemia. When Peptide D and Peptide E were administered, mice were died. This is believed that the proper amounts of Peptide D and Peptide E were lower values than 10 mg/kg.

Figure 17B:
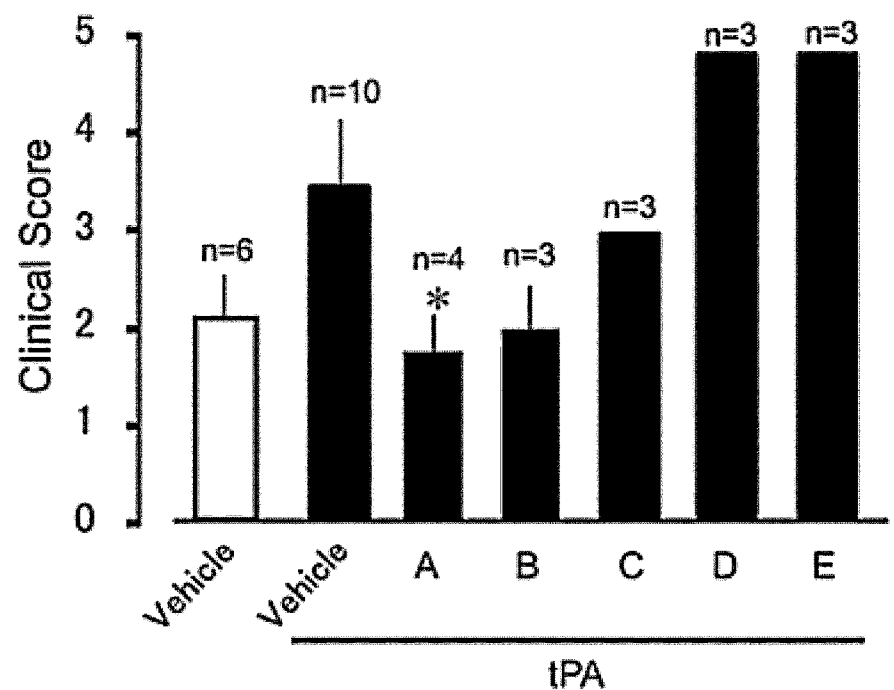
FIG. 17B shows a quantitative analysis of evaluation scores of motor dysfunction at 24 hours after ischemia when Peptides A, B, C, D or E and tPA are used in combination after 4 hours of tMCAO ischemia.
Figure 17C:
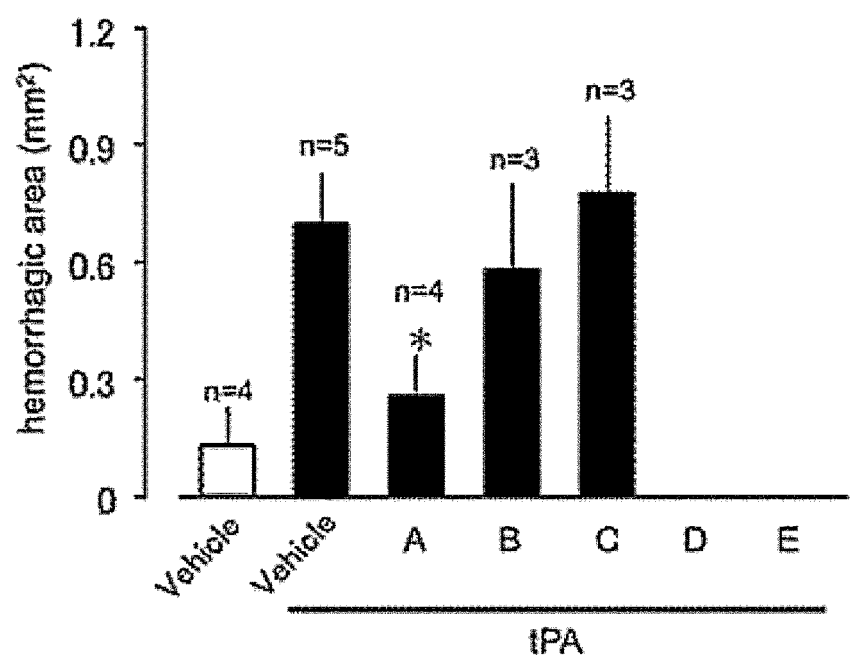
FIG. 17C shows a quantitative analysis of hemorrhagic action in the cerebral cortex and corpus striatum when Peptides A, B, C, D or E and tPA are used in combination after 4 hours of tMCAO ischemia.

FIG. 17B shows a quantitative analysis of evaluation scores of motor dysfunction after 24 hours after ischemia when Peptides A, B, C, D or E and tPA are used in combination after 4 hours of tMCAO ischemia. FIG. 17B shows the scores in the cases of intravenous coadministration of control, 10 mg/kg Peptides A, B, C, D or E with tPA. FIG. 17C shows a quantitative analysis of hemorrhagic action in the cerebral cortex and corpus striatum when Peptides A, B, C, D or E and tPA are used in combination after 4 hours of tMCAO ischemia. FIG. 17C shows the scores in the cases of control, tPA-alone control, and coadministration of tPA and 10 mg/kg Peptides A, B, C, D or E. Peptide A significantly inhibited both exacerbation of motor dysfunction and cerebral hemorrhage which are tPA-induced side effects. Peptide B tended to inhibit motor dysfunction but did not have an influence on cerebral hemorrhage. Peptide C did not show effects on any side effects. In Peptide D and Peptide E, all mice were died. Since P6 has an action on vascular systems, the possibility that some sort of action on the vascular systems was enhanced in Peptide D and Peptide E was shown.

Example 11

In Peptide A which inhibited all side effects of tPA, the dose-dependency of the inhibitory effect was examined. A tMCAO model was created by middle cerebral artery occlusion for 4 hours, and in the total 8 groups of the vehicle administered group in which PBS, a solvent of modified P6: A (Peptide A), was i.v. administered immediately after reperfusion, the Peptide A-alone administered group in which 1, 3 and 10 mg/kg Peptide A was (i.v.) administered, the tPA-alone administered group in which 10 mg/kg tPA was i.v. administered, and the coadministration group in which 10 mg/kg tPA and 1, 3 and 10 mg/kg Peptide A were (i.v.) administered, motor dysfunction after 24 hours of tMCAO treatment, as well as cerebral hemorrhage were evaluated, in which, after blood was removed by perfusion using PBS cooled with ice after 24 hours of ischemic treatment, the blood in cerebral tissue which could not be removed by perfusion was regarded as hemorrhage due to a failure of cerebral vessels.

Figure 18A:
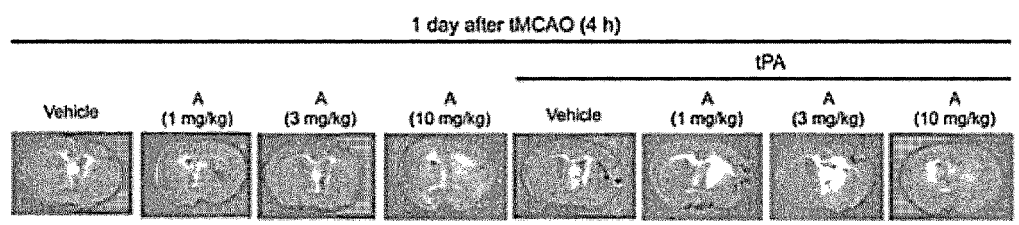
FIG. 18A shows photographs showing hemorrhagic action in the cerebral cortex and corpus striatum when 1, 3 and 10 mg/kg Peptide A is used alone, or each and tPA are used in combination after 4 hours of tMCAO ischemia.

FIG. 18A shows photographs showing hemorrhagic action in the cerebral cortex and corpus striatum when 1, 3 and 10 mg/kg Peptide A were used alone, or each and tPA were used in combination after 4 hours of tMCAO ischemia. FIG. 18A shows photographs in the cases of control, Peptide A 1 mg/kg administration, 3 mg/kg administration and 10 mg/kg administration, tPA-alone (control), and tPA and Peptide A 1 mg/kg administration, 3 mg/kg administration and 10 mg/kg administration.

Figure 18B:
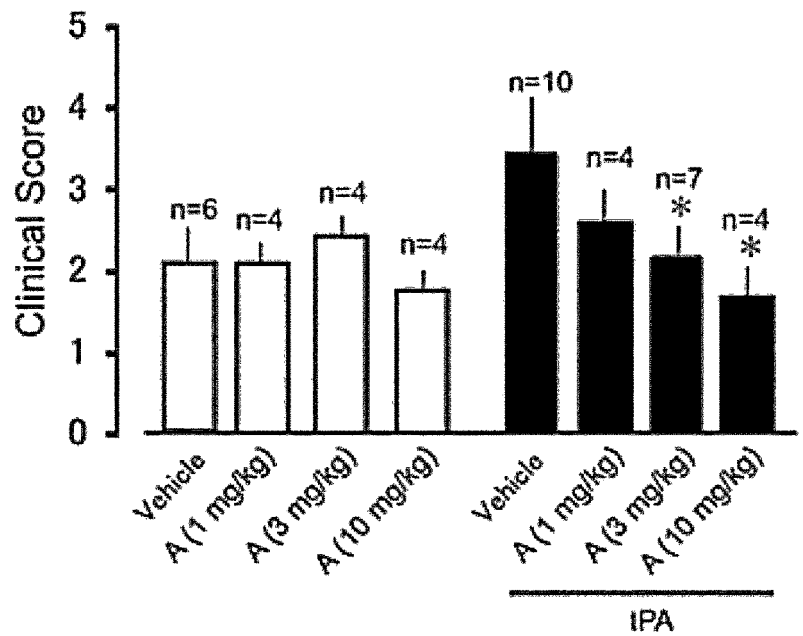
FIG. 18B shows a quantitative analysis of evaluation scores (Clinical Score) of motor dysfunction 24 hours after ischemia when 1, 3 and 10 mg/kg Peptide A is administered alone, or each and tPA are intravenously coadministered after 4 hours of tMCAO ischemia.
Figure 18C:
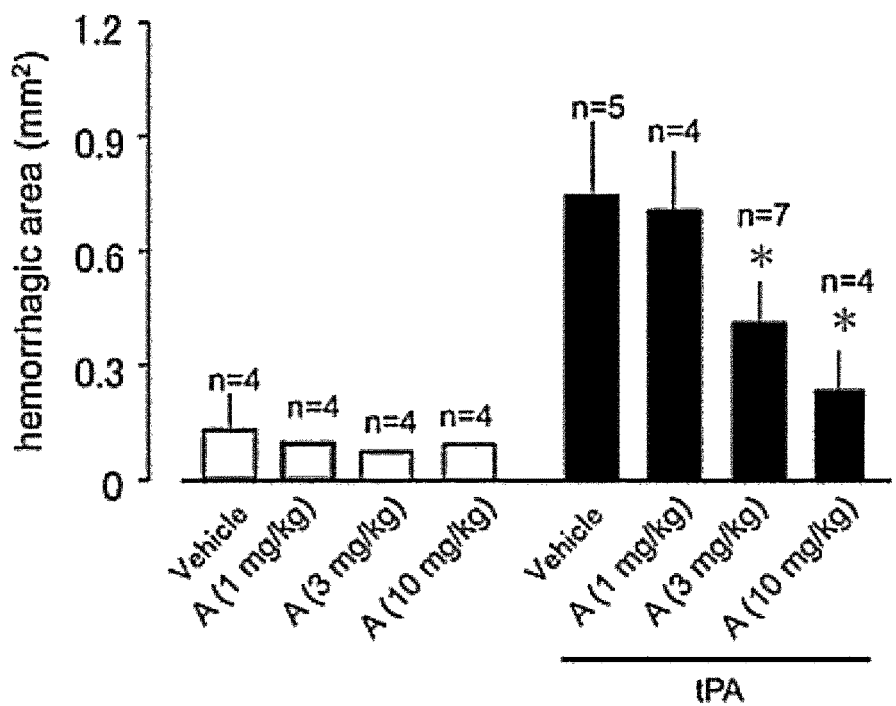
FIG. 18C shows a quantitative analysis of hemorrhagic action in the cerebral cortex and corpus striatum when 1, 3 and 10 mg/kg Peptide A is used alone, or each and tPA are used in combination after 4 hours of tMCAO ischemia.

FIG. 18B shows a quantitative analysis of evaluation scores (Clinical Score) of motor dysfunction at 24 hours after ischemia when 1, 3 and 10 mg/kg Peptide A was administered alone, or each and tPA were intravenously coadministered after 4 hours of tMCAO ischemia. FIG. 18B shows the evaluation scores in the cases of control, Peptide A 1 mg/kg administration, 3 mg/kg administration and 10 mg/kg administration, tPA-alone (control), and tPA and Peptide A 1 mg/kg administration, 3 mg/kg administration and 10 mg/kg administration. FIG. 18C shows a quantitative analysis of hemorrhagic action in the cerebral cortex and corpus striatum when 1, 3 and 10 mg/kg Peptide A was used alone, or each and tPA were used in combination after 4 hours of tMCAO ischemia. FIG. 18C shows hemorrhagic areas in the cases of control, Peptide A 1 mg/kg administration, 3 mg/kg administration and 10 mg/kg administration, tPA-alone (control), and tPA and Peptide A 1 mg/kg administration, 3 mg/kg administration and 10 mg/kg administration. As shown in FIG. 18B, the Peptide A-alone administration did not show a significant protective effect on ischemia for 4 hours, which is strong treatment, even in any dose (1 to 10 mg/kg intravenous administration). As shown in FIG. 18C, however, Peptide A was confirmed to dose-dependently inhibit the exacerbation of motor dysfunction and cerebral hemorrhage induced from tPA treatment.

From FIG. 18C, hemorrhage was slightly confirmed in the cerebral cortex region in the vehicle administered group ($0.1\pm0.1$ mm$^2$) in which PBS, a solvent of modified P6: A, was i.v. administered to a tMCAO model by middle cerebral artery occlusion for 4 hours, and the modified P6: A-alone administered group in which 1, 3 and 10 mg/kg modified P6: A was (i.v.) administered thereto (1 mg/kg: $0.09\pm0.01$ mm$^2$, 3 mg/kg: $0.06\pm0.01$ mm$^2$, and 10 mg/kg: $0.08\pm0.01$ mm$^2$). However, a declining trend in Clinical score and the significant expansion of the hemorrhagic region were confirmed in the tPA-alone administered group ($0.7\pm0.2$ mm$^2$), and further by using modified P6: A and tPA in combination, a dose-dependent improvement in Clinical score and the scale-down of hemorrhagic region were shown (tPA+1 mg/kg modified P6: A: $0.7\pm0.2$ mm$^2$, tPA+3 mg/kg modified P6: A: $0.4\pm0.1$ mm$^2$, and tPA+10 mg/kg modified P6: A: $0.2\pm0.1$ mm$^2$), which suggested that modified P6: A inhibited tPA-induced cerebral hemorrhage.

Example 12

Evaluation in a PIT Model

Reduction in the Protective Effect Due to Delay in Treatment Time by tPA

Evaluation was carried out in a thrombotic cerebral infarction PIT model to which the in vivo onset principle of cerebral infarction is closely analogous. Firstly, when protection of tPA on the PIT model was examined, a significant decrease in the infarct region was confirmed by treatment after an hour corresponding to the hyperacute phase after thrombus formation (infarction). This protective effect was reduced by delaying (2 to 4 hours) treatment time by tPA. In addition, when tPA was administered after 6 hours of ischemia, the protective effect was not confirmed. However, even when tPA was administered after 6 hours of ischemia, exacerbation of dysfunction, which can be said to be a side effect, was not confirmed. Thus, it is thought that examination is required in a system in which treatment time is more delayed. It is revealed that the PIT model is not appropriate for clinical scores evaluating motor dysfunction, and evaluation will be carried out by behavioristic techniques such as a Rota rod method.

Figure 19:
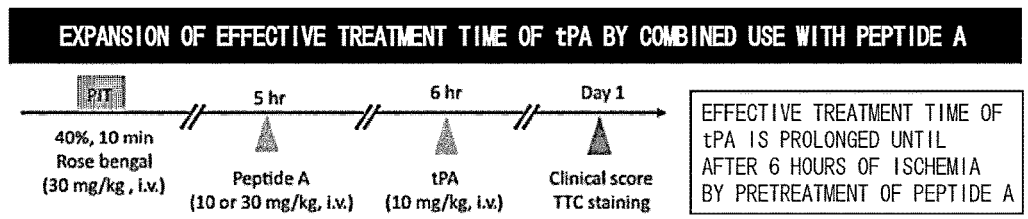
FIG. 19 shows the administration schedule of Peptide A and tPA in a PIT model.
Figure 20A:
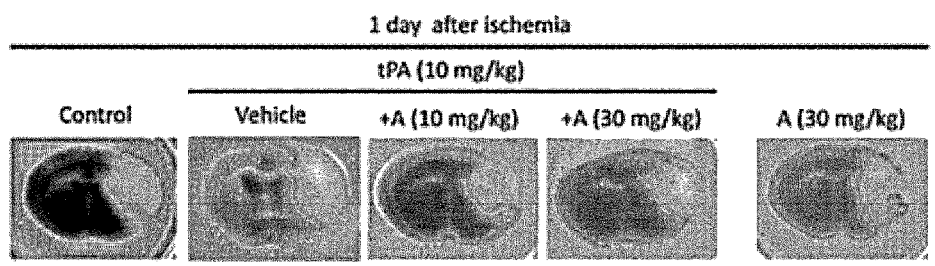
FIG. 20A shows photographs showing cerebral infarction in the cerebral cortex and corpus striatum region which was eventually recognized 24 hours after photochemical thrombus formation by causing a thrombus in the middle cerebral artery by photoirradiation immediately after administration of rose bengal, and after 5 hours, intravenously administering control, or 10 or 30 mg/kg Peptide A, and further after an hour, administering tPA.
Figure 20B:
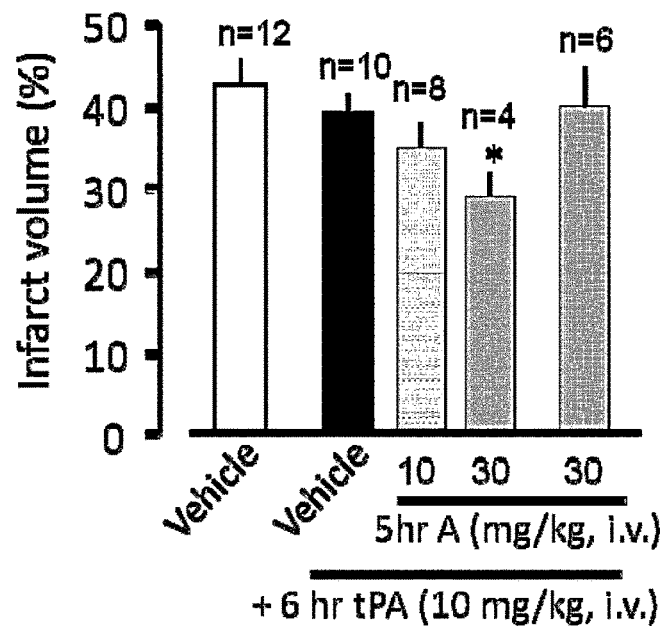
FIG. 20B shows quantification of the infarct region in FIG. 20A.
Figure 20C:
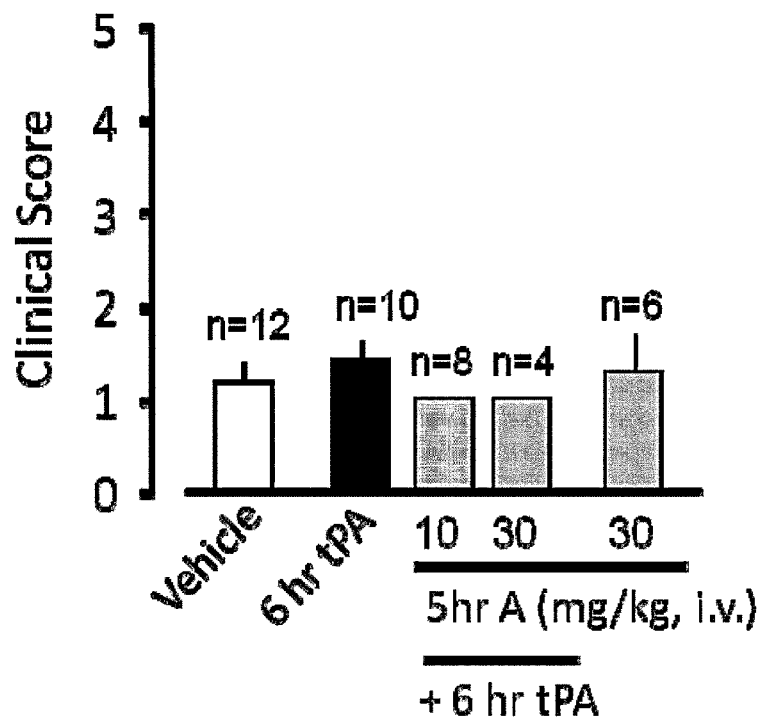
FIG. 20C summarizes the evaluation scores of motor dysfunction which was eventually recognized 24 hours after photochemical thrombus formation by causing a thrombus in the middle cerebral artery by photoirradiation immediately after administration of rose bengal, and after 5 hours, intravenously administering control, or 10 or 30 mg/kg Peptide A, and further after an hour, administering tPA.

Expansion of Effective Treatment Time by tPA by Using Peptide a and tPA in Combination The combined effect of Peptide A which has an inhibitory effect on side effects by tPA in the tMCAO model, and tPA in the PIT model of tPA was analyzed after 4 hours of ischemia. FIG. 19 shows the administration schedule of Peptide A and tPA in the PIT model. FIG. 20A shows photographs showing cerebral infarction in the cerebral cortex and corpus striatum region which was eventually recognized 24 hours after photochemical thrombus formation by causing a thrombus in the middle cerebral artery by photoirradiation immediately after administration of rose bengal, and after 5 hours, intravenously administering control, or 10 or 30 mg/kg Peptide A, and further after an hour, administering tPA. FIG. 20A shows the results of control, tPA-alone control, combined use with 10 or 30 mg/kg Peptide A, and 30 mg/kg Peptide A-alone. FIG. 20B shows quantification of the infarct region in FIG. 20A. FIG. 20C summarizes the evaluation scores of motor dysfunction which was eventually recognized 24 hours after photochemical thrombus formation by causing a thrombus in the middle cerebral artery by photoirradiation immediately after administration of rose bengal, and after 5 hours, intravenously administering control, or 10 or 30 mg/kg Peptide A, and further after an hour, administering tPA. FIG. 20C shows the results of control, tPA-alone control, combined use with 110 or 30 mg/kg Peptide A, and 30 mg/kg Peptide A-alone. From FIG. 20A, FIG. 20B and FIG. 20C, when Peptide A was administered an hour (after 5 hours of ischemia) before administration of tPA, a protective effect was recognized in the histochemical analysis. In addition, the effect of Peptide A was dose-dependent (10 mg/kg and 30 mg/kg). On the other hand, the protective effect was not recognized by the Peptide A-alone administration. It is thought that the protective effect is the synergistic effect of tPA and Peptide A.

The damaged cerebral region by TTC staining was $42\pm2.5\%$ in the PIT treatment-alone, and $40\pm1.8\%$ in the group in which tPA was administered alone after 6 hours of PIT treatment, and a significant change between two groups was not observed. In addition, a significant change in clinical scores between the PIT treatment-alone ($1.3\pm0.2$) and the tPA-alone administered group ($1.5\pm0.2$) was not observed.

The above results revealed that the tPA-alone administration in later stages of ischemia induced exacerbation of motor function disorders and hemorrhage but did not have an influence on the expansion of the damaged cerebral region.

Furthermore, in the Peptide A-alone administered group, the damaged cerebral region by TTC staining was $40\pm4.8\%$, and the Clinical score was $1.3\pm0.4$, and thus there were no changes as compared to the PIT treatment-alone. However, in the group in which tPA and Peptide A were coadministered after PIT treatment, a trend toward dose-dependent improvement in the damaged cerebral region was shown in the 10 mg/kg and 30 mg/kg administered groups (10 mg/kg: $37\pm2.7\%$, 30 mg/kg: $29\pm2.1\%$), and it was revealed that the 30 mg/kg Peptide A administered group significantly showed a decrease in the damaged cerebral region. In the clinical score, however, the improving effect was not recognized in the group in which tPA and Peptide A were coadministered (10 mg/kg: $1\pm0$, 30 mg/kg: $1\pm0$).

In the previous example, basic peptide P6 showed the greatest protective effect by 10 pmol/eye intravitreal administration. Because of this, one tenth of this dose, 1 pmol/eye, was regarded as the desired value in prototype peptides including Peptide A to Peptide E. Compared with P6, 14 samples of the produced 21 samples were highly active by 1 pmol/eye. Furthermore, it was found that 5 samples (Peptide A to Peptide E) were highly active by 0.1 pmol/eye, which means to have activity 100 times higher than P6.

Secondary Evaluation in an Animal Model

In the tMCAO model (ischemia for 60 minutes—reperfusion), P6 inhibited motor dysfunction by 1 mg/kg single administration into the caudal vein after an hour of ischemia. In the protective effect, however, an inhibitory effect in the case of high dose administration such as 3 mg/kg and 10 mg/kg was not as good as the case by 1 mg/kg single administration. An object of the present example was to find an active peptide showing a dose of 0.1 mg/kg as the desired value and a dose-dependent protective effect. When 5 highly active peptides were examined, it was revealed that 2 types of peptides showed the protective effects by 3 mg/kg (Peptide A) and 10 mg/kg (Peptide B) and further had dose-dependency. Their activities had differences and any activity was not recognized in the other 3 types of peptides, which are believed to be problems of in vivo stability and brain-migration by intravenous administration.

The protective effect on cerebral hemorrhage, a major side effect of a thrombolytic agent tPA, was examined. By reperfusion after 10 mg/kg tPA treatment to a tMCAO model (ischemia for 4 hours), motor dysfunction after a day was deteriorated (from score 2 to 3.5), which induced cerebral hemorrhage. It was revealed to protect against the exacerbating effect by treating Peptide A simultaneously with tPA. In addition, when basic peptide P6 was also examined, P6 was recognized to have a trend to exacerbate cerebral hemorrhage. From the above, Peptide A was regarded as the high-priority sample for the prototype of a therapeutic agent for cerebral infarction.

In the acute phase of cerebral infarction, a thrombolytic agent, tPA (tissue plasminogen activator), has been clinically put to practical use, however, the effective therapeutic time is within 4.5 hours after the onset of cerebral infarction, which means that the use of tPA is temporally limited. In the present example, it has been revealed by an inspection using a tMCAO model, an animal model of cerebral infarction, that the administration of tPA after 6 hours of cerebral ischemia induces cerebral hemorrhage, and also its protective effect on brain is not observed in the PIT model by TTC staining, which examines the activity of mitochondria. Furthermore, it was found that motor function was exacerbated as compared to that of the case of only PIT ischemia in the evaluation test of motor coordination using Rota rod in terms of motor behavioristics.

Example 13

Analyses of synergistically protective effects of prototype peptides with tPA by changing the treatment time and concentration (applying Rota rod test for analyses of motor function)

The Accelerated Rota rod test is a technique specialized for analyses of motor coordination and motor learning function. The motor coordination is known to decrease due to dysfunction of nerve cells mainly existing in the corpus striatum region. In addition, motor learning is mainly controlled in cerebellum and the motor learning function decreases due to dysfunction of cerebellar nerve cells.

The PIT model, an animal model of cerebral infarction, is a method by which active oxygen species can be generated specifically in a place where green light is irradiated by administering rose bengal, a photosensitive pigment, by administration into the caudal vein. The generated active oxygen species injure endothelial cells to form thrombi, which causes vascular occlusion. By irradiation of green light in the middle cerebral artery, in the cerebral cortex and corpus striatum under the control of its blood flow, ischemic injury can be caused. Therefore, it is believed that the main region responsible for clinical conditions in motor function disorders seen in the PIT model is the corpus stratum which controls motor coordination.

The Accelerated Rota rod test was carried out as an object to examine whether or not Peptide A found as a neuroprotective peptide can contribute to prolonging the effective therapeutic time of tPA in the PIT model in terms of motor coordination.

The Accelerated Rota rod test was carried out using ROTA-ROD TREADMILL FOR RATS & MICE (MK-610A, Muromachi Kikai Co., Ltd.). In the experiment, the condition of rod rotation was an acceleration of 4.5 rpm to 45 rpm for 5 minutes. Male mice (C57BL/J6) with a body weight of 20 to 25 g were placed on a rod, and the test was carried out by measuring time until the mice fell from the rod (fall latency). The trial was carried out 4 times a day with an interval of an hour every trial continuously for 3 days, and this was regarded as "Training".

Thereafter, the PIT operation was carried out, and after a week, motor function disorders were evaluated 4 trials/day and "Test" values were obtained. However, when mice did not fall down from the rotating Rota rod and rotated together with the mice clinging to the rod, dysbasia was decided at the time of continuous two rotations and measurement was finished and the time was decided as the fall time.

In the judgment test of an effect to prolong the effective therapeutic time of tPA by Peptide A, 3, 10 and 30 mg/kg Peptide A was administered into the caudal vein (i.v.) after 5 hours from the end of PIT ischemia and subsequently 10 mg/kg tPA was (i.v.) administered 6 hours after ischemia. The effect was examined after a week. The group in which rose bengal was i.v. administered and green light was not irradiated was regarded as the Sham group, and the group in which rose bengal was i.v. administered and green light was irradiated and treatments were carried out with a solvent PBS (100 μL/10 g, i.v.) after 5 hours and a physiological saline solution (i.v., 100 μL/10 g) after 6 hours was regarded as the vehicle group. The group in which treatments were carried out with a solvent PBS (100 L/10 g, i.v.) after 5 hours and tPA (10 mg/kg, i.v.) after 6 hours was regarded as the tPA-alone group, and the group in which treatments were carried out with Peptide A in a solvent (100 μL/10 g, i.v.) after 5 hours and tPA (10 mg/kg, i.v.) after 6 hours was regarded as the Peptide A+tPA treated group.

A statistical analysis between the sham group (n=6), the vehicle group (n=8), the tPA-alone administered group (n=10), the Peptide A+tPA treated group, Peptide A (3 mg/kg) (n=6), Peptide A (10 mg/kg) (n=6), and Peptide A (30 mg/kg) (n=6) was carried out every trial using one-way ANOVA post hoc Tukey-Kramer method.

Literature cited: Jung-Kil Lee et al. Photochemically induced cerebral ischemia in a mouse model. Surgical Neurology 67 (2007) 620-625

Figure 21:
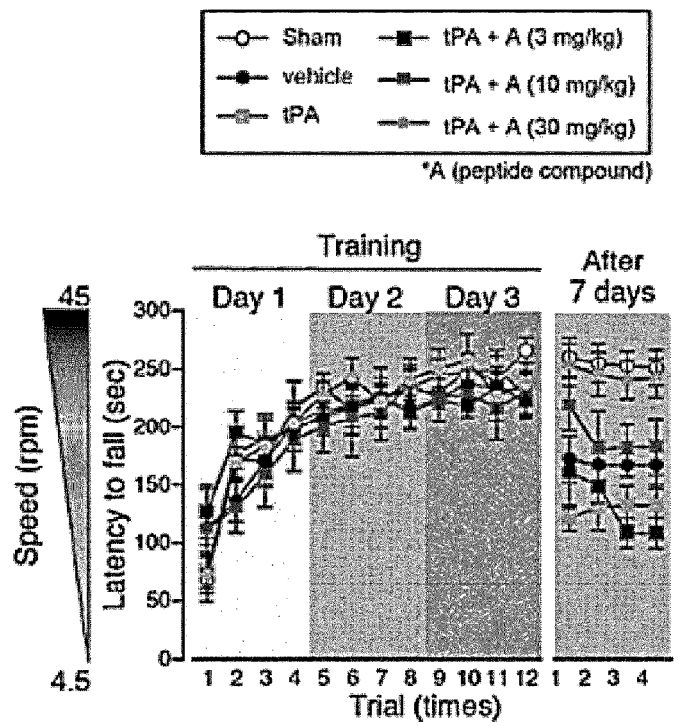
FIG. 21 shows the results of Accelerated Rota rod test, which is a line graph showing time until dysbasia.
Figures 22, 23:
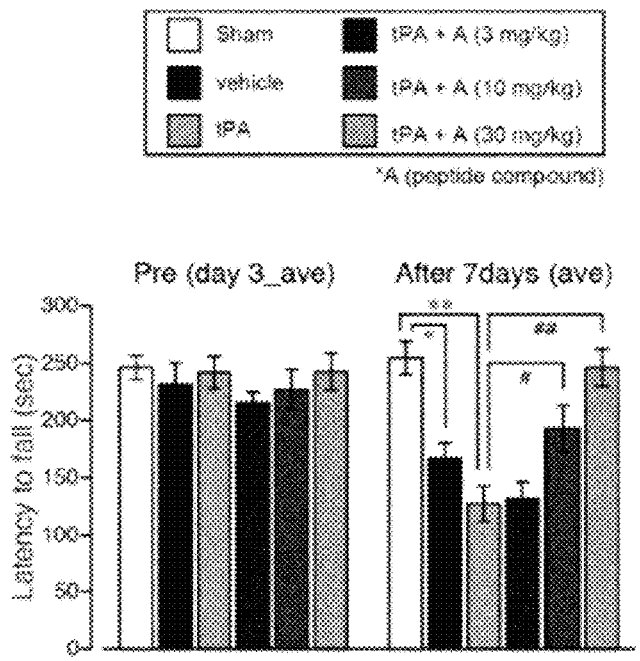
FIG. 22 is a bar graph showing the average values during the training period and the average values after 7 days.
FIG. 23 is a reference figure showing the sequences of P6, Peptide A to Peptide E, and the contents thereof are the same as in Table 1.

FIG. 21 shows the results of Accelerated Rota rod test, which is a line graph showing time until dysbasia. In FIG. 21, A indicates Peptide A. FIG. 22 is a bar graph showing the average values during the training period and the average values after 7 days.

From FIGS. 21 and 22, when only tPA was administered, deterioration in motor ability was observed. On the other hand, it has been shown that in the system in which 3 mg/kg Peptide A was administered, motor ability was slightly recovered, and in the systems in which 10 mg/kg and 30 mg/kg Peptide A was administered, motor ability was largely recovered.

In Training carried out continuously for 3 days until the previous day of PIT treatment, no changes were observed in all groups, and about motor function after 7 days of the administration of each drug after PIT treatment, a significant decrease in motor function was shown (167±13 sec) in the vehicle group in which only PIT treatment was carried out as compared to the Sham group, and further it was revealed that a further trend towards exacerbation was shown in the tPA-alone administered group (127±15 sec). In addition, in the group in which tPA and modified P6: A were coadministered after PIT treatment, a significant trend toward improvement was not recognized by 3 mg/kg modified P6: A administration (132±15 sec), but in the 10 mg/kg and 30 mg/kg administered groups, a dose-dependently improving effect on motor function could be found (10 mg/kg: 192±21 sec, 30 mg/kg: 246±16 sec). From the above results, exacerbation of motor function disorders induced by administering tPA after 6 hours of PIT treatment was improved by pre-treating modified P6: A, which suggested that modified P6: A was effective for inhibiting motor dysfunction induced by tPA.

As statistical processing, a significant test was carried out using the Dunnett's test after an analysis of variance by One-factor ANOVA. In addition, * indicated $p<0.05$ and ** indicated $p<0.01$ between the sham group and a group having significance thereto, and # indicated $p<0.05$ and ## indicated $p<0.01$ between the tPA-alone administered group and the modified P6: A coadministered groups having significance thereto.

FIG. 23 is a reference figure showing the sequences of P6 and Peptide A to Peptide E.

The results confirmed that Peptide A had an inhibitory action on side effects by tPA.

Figures 24, 25:
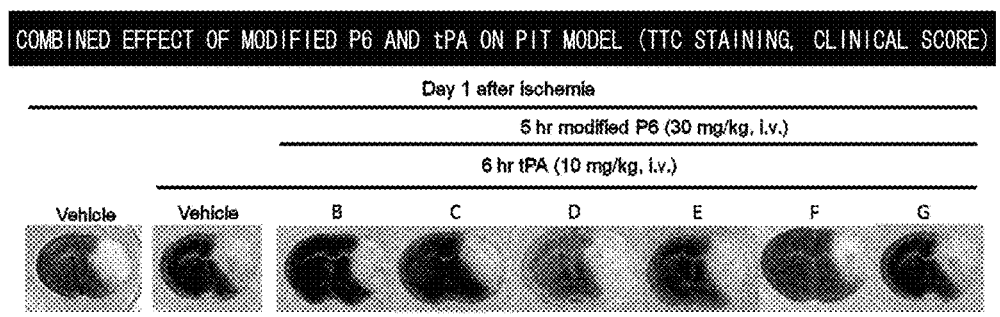
FIG. 24 is a reference figure showing the sequences of P6, Peptide A to Peptide U.
FIG. 25 shows photographs substituted for drawings, which show the corpus striatum when a peptide and tPA were suitably administered after 5 hours of ischemia.

FIG. 24 is a reference figure showing the sequences of P6 and Peptide A to Peptide U. In the figure,
indicates pyroglutamic acid,
Ac—N indicates acetylasparagine,
E-NH$_2$ indicates glutamic acid amide (isoglutamine),
Nva indicates norvaline, and
Nle indicates norleucine.

Example 13

Examination of Effects of Peptides Other than Peptide A in the PIT Model (Evaluation of the Damaged Cerebral Region by Clinical Score and TTC Staining)

Figure 26A:
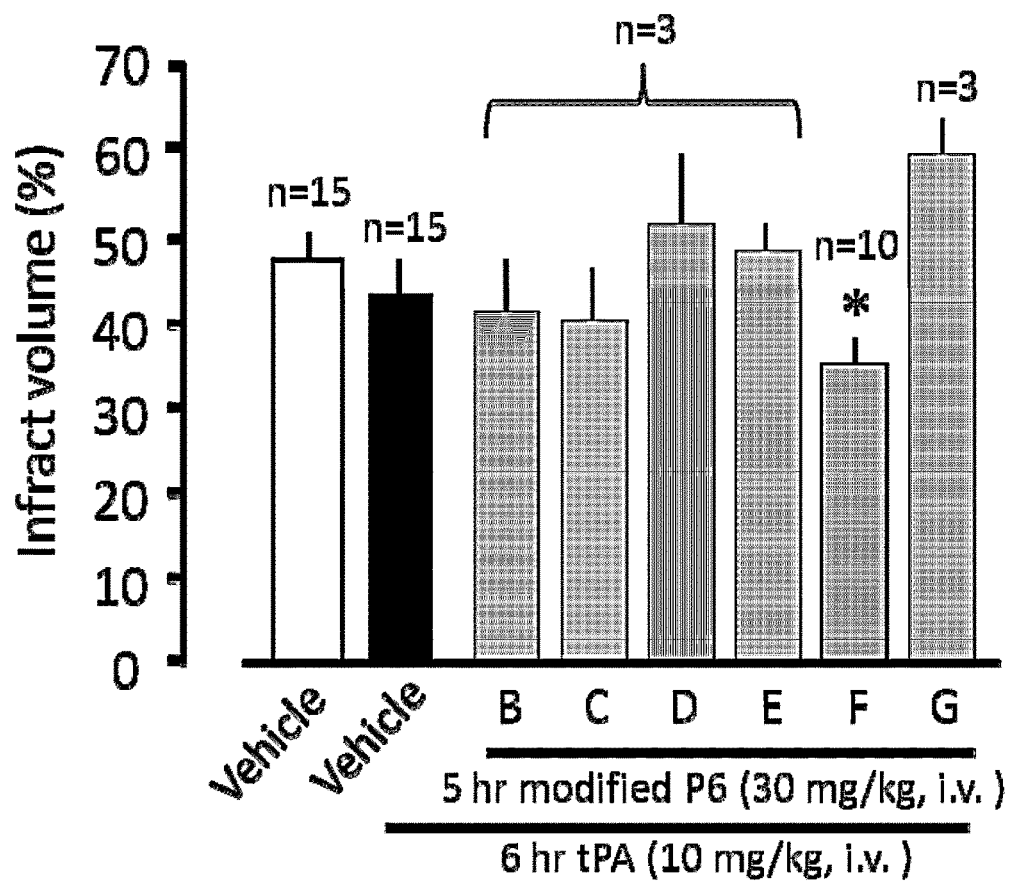
FIG. 26A is a graph showing the infract volume (%).
Figure 26B:
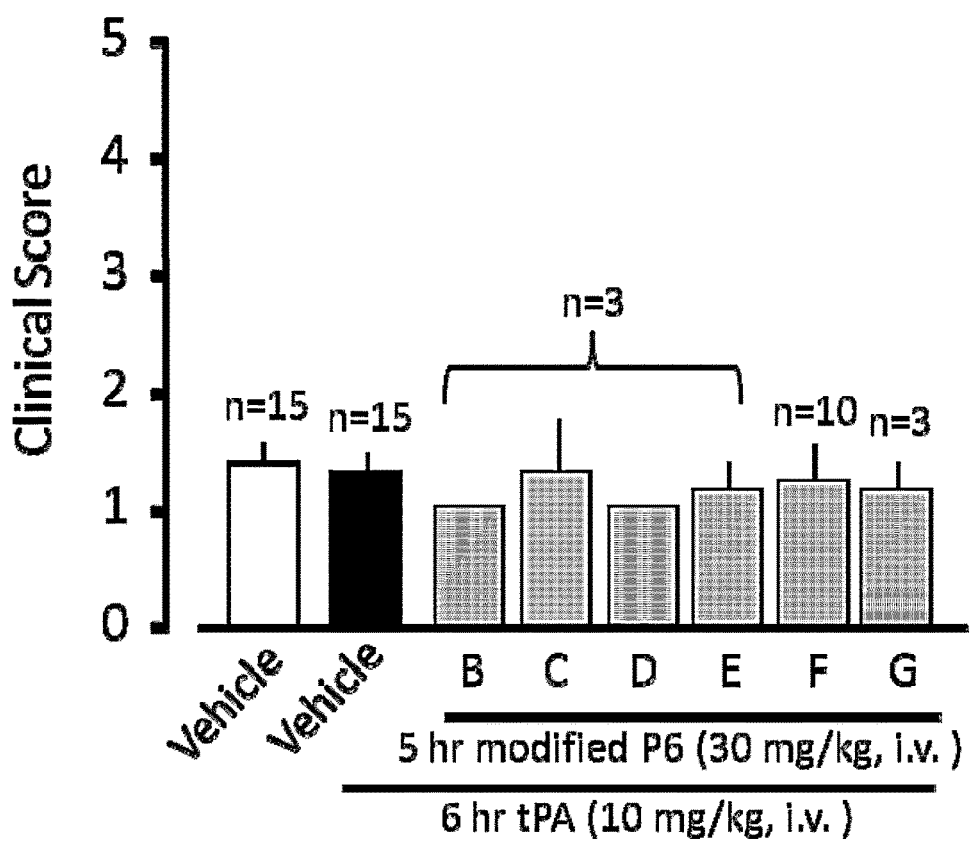
FIG. 26B is a graph showing the evaluation scores.

Peptides B to G other than Peptide A were evaluated in the same manner as in examples previously described in which used peptides were changed. FIG. 25 shows photographs substituted for drawings, which show the results of TTC staining of the corpus striatum when a peptide and tPA were suitably administered after 5 hours of ischemia. FIG. 26A is a graph showing the infract volume (%). FIG. 26B is a graph showing the evaluation scores.

The damaged cerebral region by TTC staining was 48±2.5% in the PIT treatment-alone, and 44±2.6% in the group in which tPA was administered alone after 6 hours of PIT treatment, and when modified P6: F was used in combination with tPA, a trend towards improvement was confirmed (tPA+F: 37±3%). In addition, when modified P6: B, C, D, E or G was combined, the following results were obtained (tPA+B: 42±6.1%, tPA+C: 42±4.5%, tPA+D: 52±7.2%, tPA+E: 50±2.6% and tPA+G: 60±3%). In addition, the Clinical score was 1.5±0.1 in the PIT treatment-alone, and 1.4±0.1 in the group in which tPA was administered alone after 6 hours of PIT treatment. In addition, when modified P6 was used in combination with tPA, no changes were observed (tPA+B: 1±0, tPA+C: 1.5±0.4, tPA+D: 1±0, tPA+E: 1.2±0.2, tPA+F: 1.2±0.2 and tPA+G: 1.2±0.2).

Figure 27:
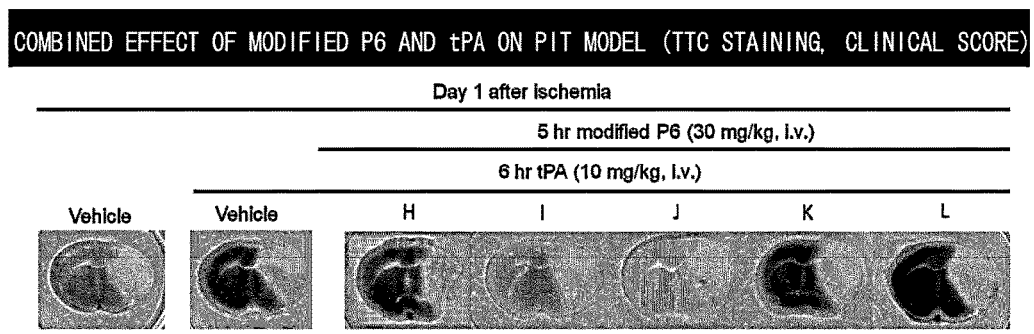
FIG. 27 shows photographs substituted for drawings, which show the corpus striatum when a peptide and tPA were suitably administered after 5 hours of ischemia.
Figure 28A:
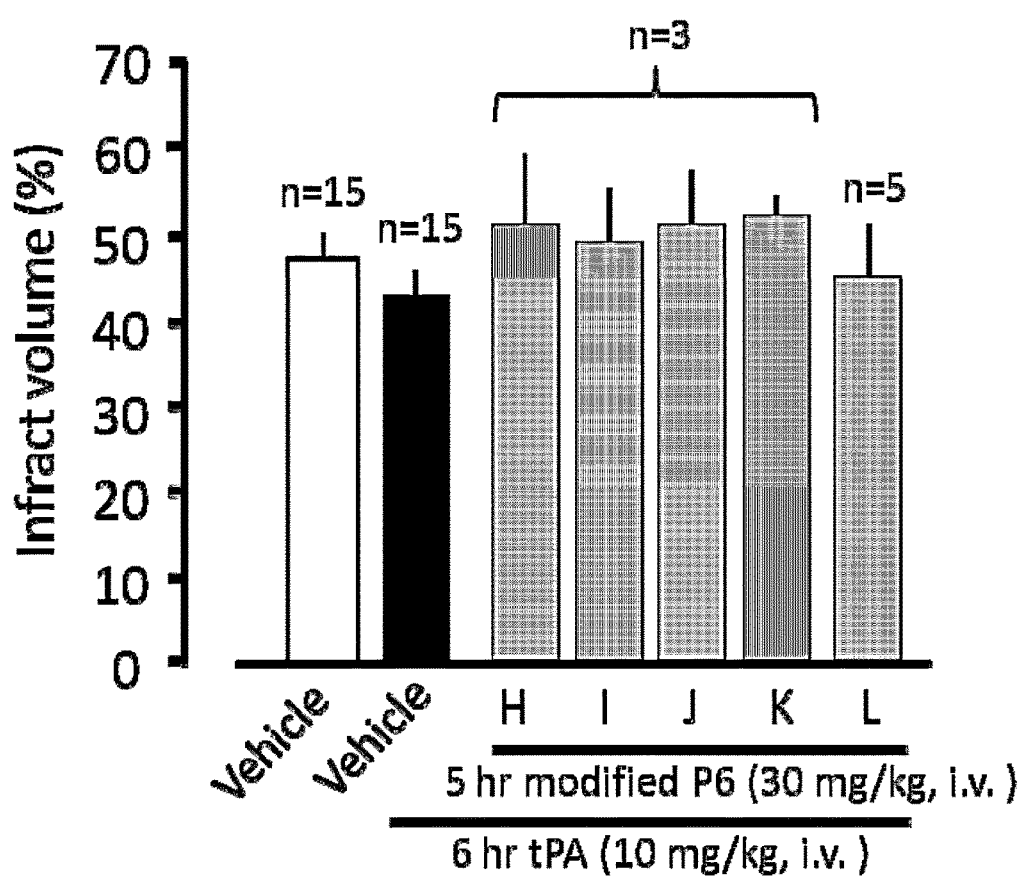
FIG. 28A is a graph showing the infract volume (%).
Figure 28B:
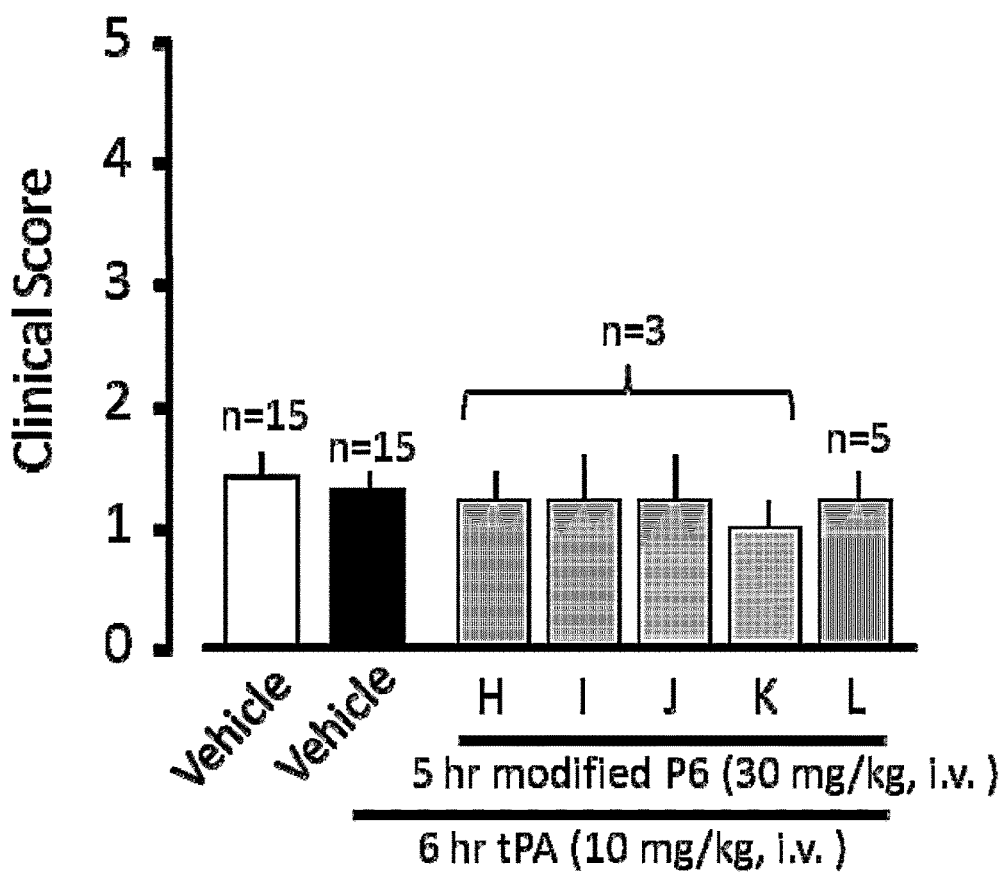
FIG. 28B is a graph showing the evaluation scores.

Peptides H to L other than Peptide A were evaluated in the same manner as in examples previously described in which used peptides were changed. FIG. 27 shows photographs substituted for drawings, which show the results of TTC staining of the corpus striatum when a peptide and tPA were suitably administered after 5 hours of ischemia. FIG. 28A is a graph showing the infract volume (%). FIG. 28B is a graph showing the evaluation scores.

The damaged cerebral region by TTC staining was 48±2.5% in the PIT treatment-alone, and 44±2.6% in the group in which tPA was administered alone after 6 hours of PIT treatment. In addition, when Peptides: H, I, J, K or L was combined, the following results were obtained (tPA+H: 51±8.3%, tPA+I: 48±7.8%, tPA+J: 51±4.1%, tPA+K: 53±1.7% and tPA+L: 46±5.6%). The clinical score was 1.5±0.1 in the PIT treatment-alone, and 1.4±0.1 in the group in which tPA was administered alone after 6 hours of PIT treatment. In addition, when modified P6 was used in combination with tPA, no changes in clinical score were observed (tPA+H: 1.3±0.2, tPA+I: 1.3±0.3, tPA+J: 1.3±0.3, tPA+K: 1.1±0.2 and tPA+L: 1.3±0.2).

Figure 29:
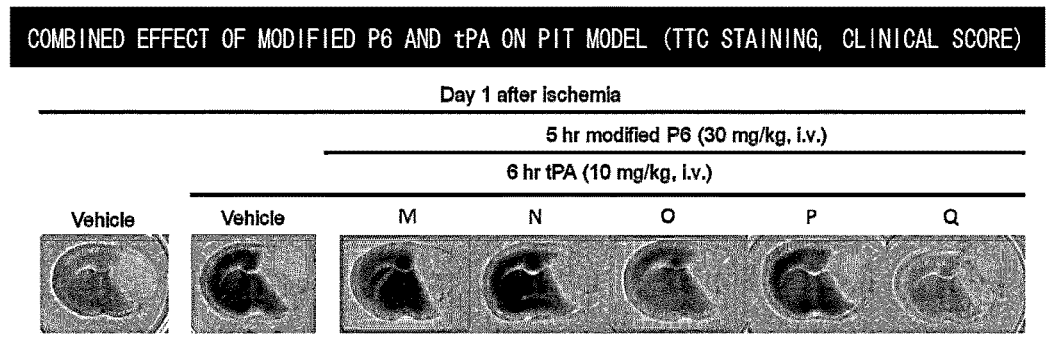
FIG. 29 shows photographs substituted for drawings, which show the corpus striatum when a peptide and tPA were suitably administered after 5 hours of ischemia.
Figure 30A:
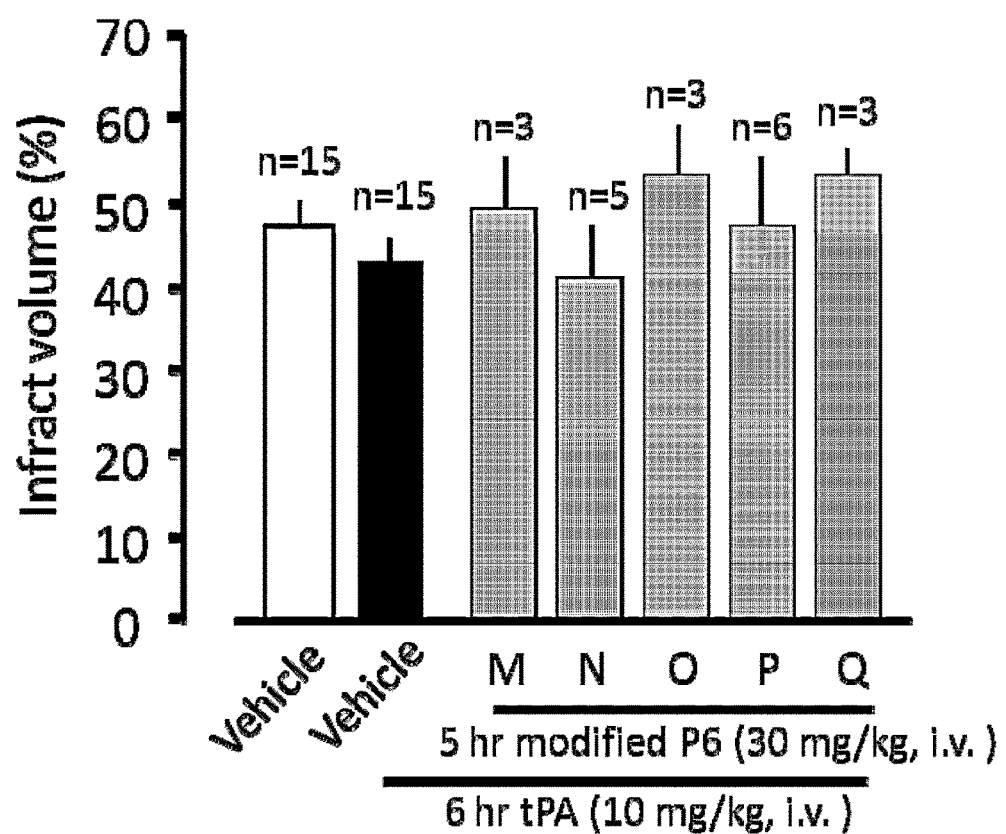
FIG. 30A is a graph showing the infract volume (%).
Figure 30B:
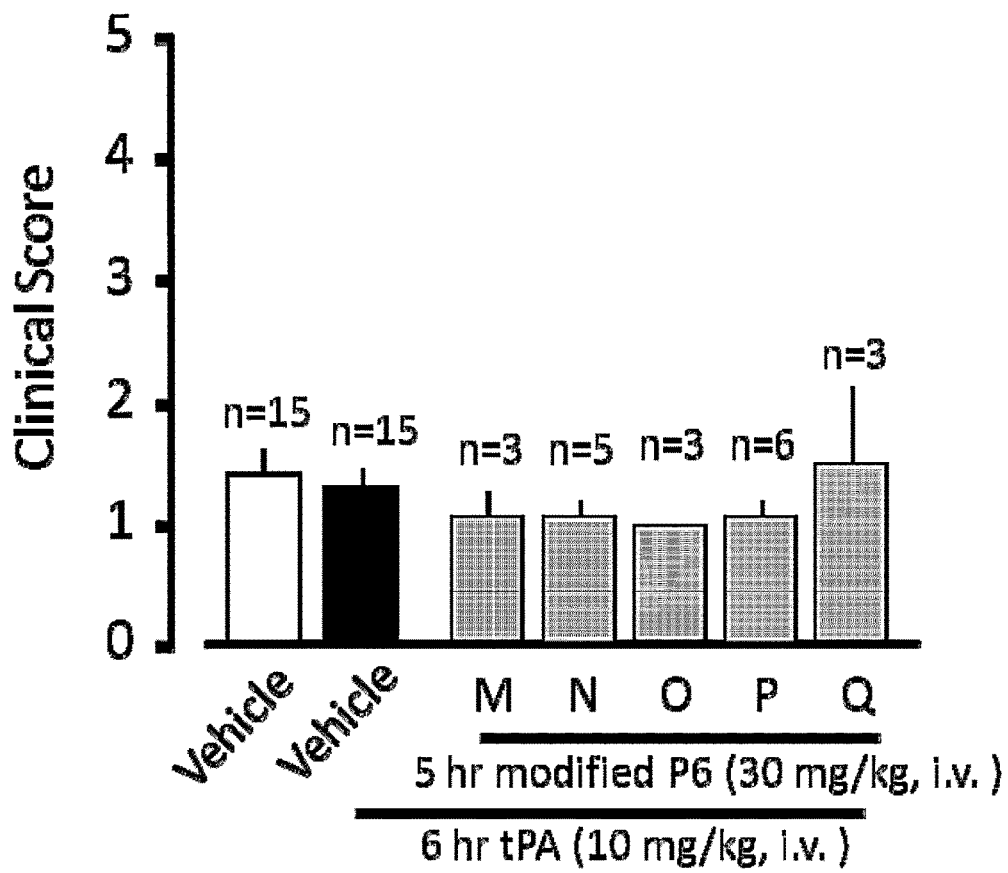
FIG. 30B is a graph showing the evaluation scores.

Peptides M to Q other than Peptide A were evaluated in the same manner as in examples previously described in which used peptides were changed. FIG. 29 shows photographs substituted for drawings, which show the results of TTC staining of the corpus striatum when a peptide and tPA were suitably administered after 5 hours of ischemia. FIG. 30A is a graph showing the infract volume (%). FIG. 30B is a graph showing the evaluation scores.

The damaged cerebral region by TTC staining was 48±2.5% in the PIT treatment-alone, and 44±2.6% in the group in which tPA was administered alone after 6 hours of PIT treatment. In addition, when Peptides: M, N, O, P or Q was combined, the following results were obtained (tPA+M: 50±5.9%, tPA+N: 43±4.9%, tPA+O: 54±5.8%, tPA+P: 47±5.1% and tPA+Q: 55±1.4%).

In addition, the clinical score was 1.5±0.1 in the PIT treatment-alone, and 1.4±0.1 in the group in which tPA was administered alone after 6 hours of PIT treatment. In addition, when modified P6 was used in combination with tPA, no changes in clinical score were observed (tPA+M: 1.1±0.2, tPA+N: 1.1±0.1, tPA+O: 1±0, tPA+P: 1.1±0.1 and tPA+Q: 1.7±0.5).

Figure 31:
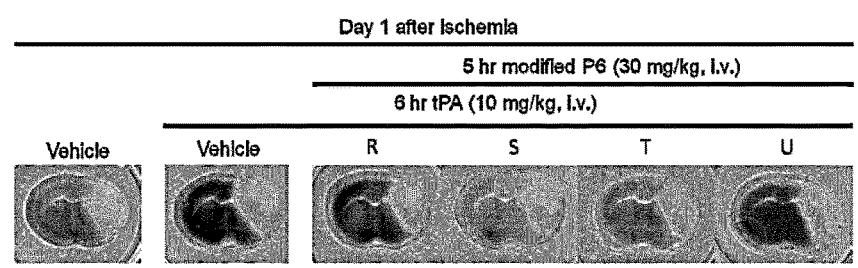
FIG. 31 shows photographs substituted for drawings, which show the corpus striatum when a peptide and tPA were suitably administered after 5 hours of ischemia.
Figure 32A:
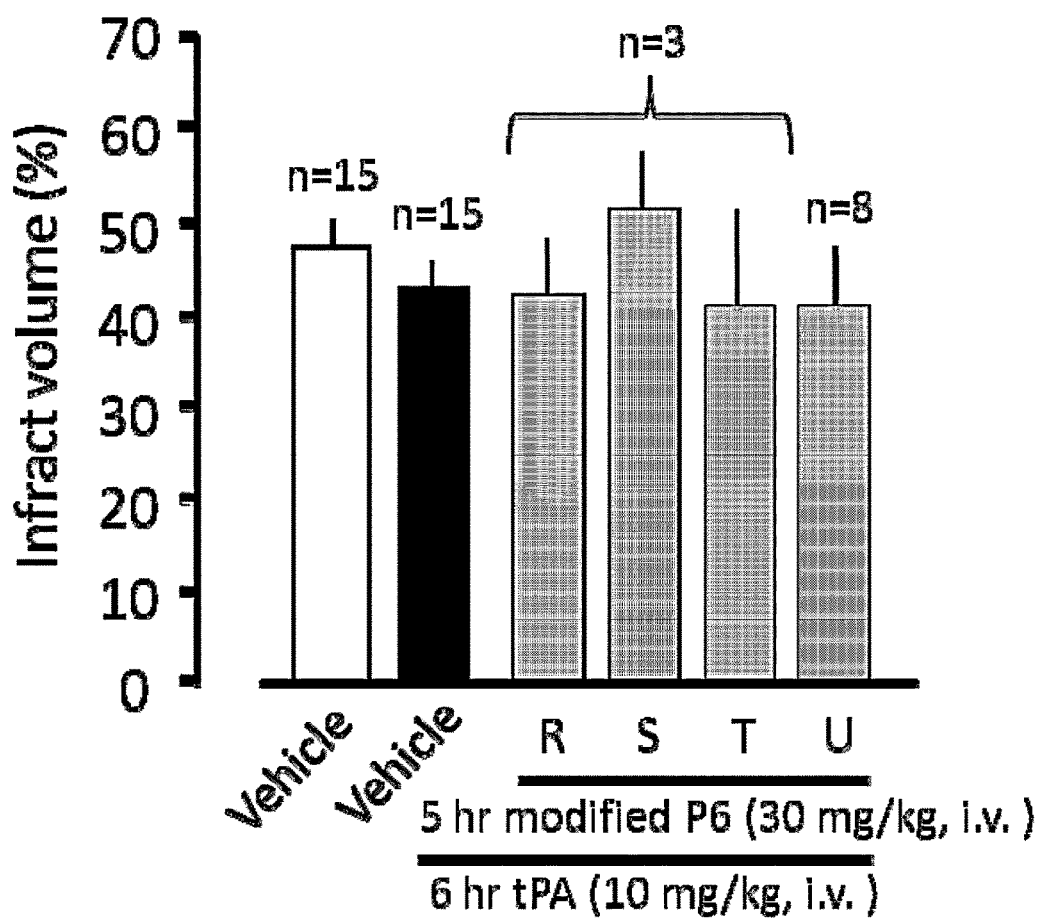
FIG. 32A is a graph showing the infract volume (%).
Figure 32B:
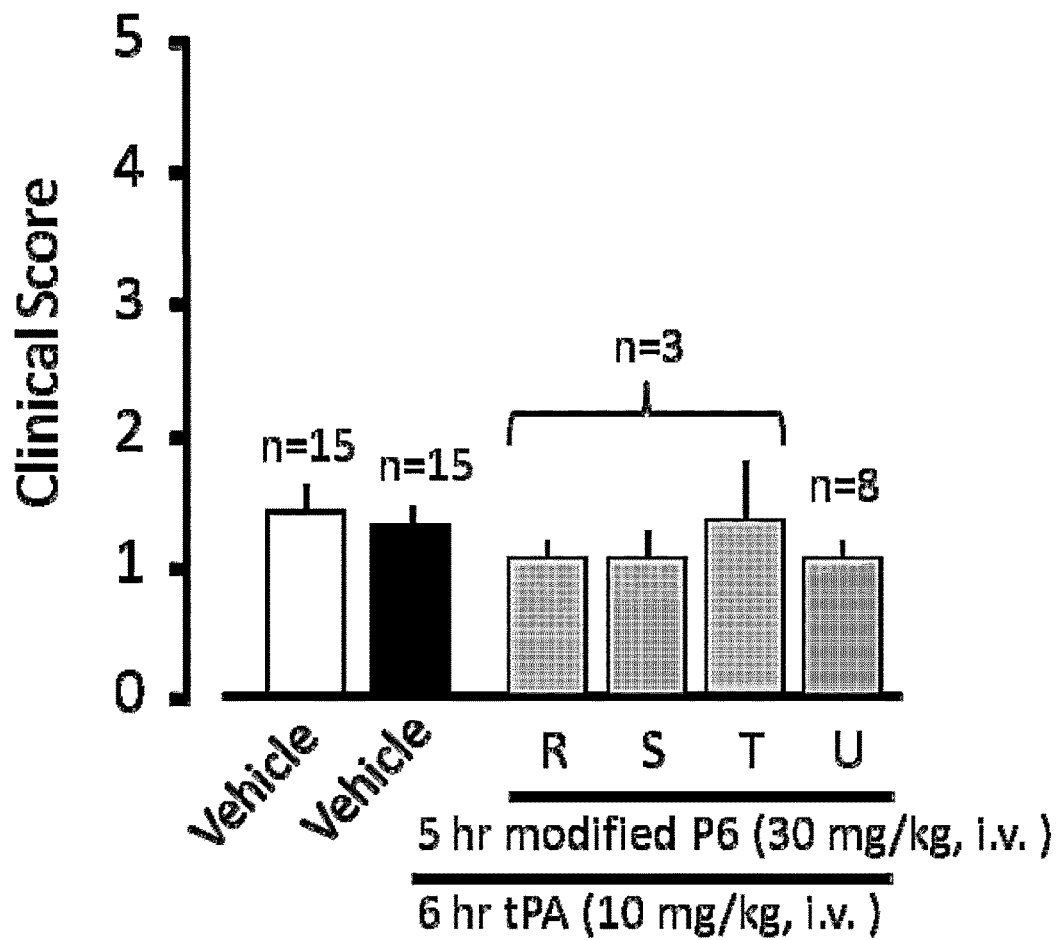
FIG. 32B is a graph showing the evaluation scores.

Peptides R to U other than Peptide A were evaluated in the same manner as in examples previously described in which used peptides were changed. FIG. 31 shows photographs substituted for drawings, which show the results of TTC staining of the corpus striatum when a peptide and tPA were suitably administered after 5 hours of ischemia. FIG. 32A is a graph showing the infract volume (%). FIG. 32B is a graph showing the evaluation scores.

The damaged cerebral region by TTC staining was 48±2.5% in the PIT treatment-alone, and 44±2.6% in the group in which tPA was administered alone after 6 hours of PIT treatment. In addition, when modified P6: R, S, T or U was combined, the following results were obtained (tPA+R: 54±4.5%, tPA+S: 51±5.7%, tPA+T: 41±9.4% and tPA+U: 41±6.3%).

In addition, the Clinical score was 1.5±0.1 in the PIT treatment-alone, and 1.4±0.1 in the group in which tPA was administered alone after 6 hours of PIT treatment. In addition, when modified P6 was used in combination with tPA, no changes in clinical score were observed (tPA+R: 1.1±0.1, tPA+S: 1.1±0.2, tPA+T: 1.4±0.4 and tPA+U: 1.1±0.1).

It is believed from the above that among P6 derivatives, Peptide A is superior followed by Peptide F.

The contents described in all publications mentioned in the present description are incorporated herein by reference herein in the same degree in which the entirety is expressed clearly.

INDUSTRIAL APPLICABILITY

The ameliorating agent for blood-brain barrier dysfunction of the present invention can ameliorate a weakening in a blood-brain barrier which can be caused by cerebral ischemia. The agent of the present invention, therefore, can be a therapeutic agent for diseases resulting from blood-brain barrier dysfunction.

SEQUENCE LISTING FREE TEXT

SEQ ID NO:1: ProTa6 (P6)
SEQ ID NO:2: P6 derivative peptide (Peptide A)
SEQ ID NO:3: P6 derivative peptide (Peptide B)
SEQ ID NO:4: P6 derivative peptide (Peptide C)
SEQ ID NO:5: P6 derivative peptide (Peptide D)
SEQ ID NO:6: P6 derivative peptide (Peptide E)
SEQ ID NO:7: Full length human prothymosin α
SEQ ID NO:8: Full length mouse prothymosin α
SEQ ID NO:9: Full length rat prothymosin α
SEQ ID NO:10: ProTh30
SEQ ID NO:11: ProTa9
SEQ ID NO:12: Peptide comprising 7 amino acids from position 50 to 56 in rat and mouse prothymosin α
SEQ ID NO:13: Peptide comprising 7 amino acids from position 51 to 57 in rat and mouse prothymosin α
SEQ ID NO:14: P6 derivative peptide (Peptide F)
SEQ ID NO:15: P6 derivative peptide (Peptide G)
SEQ ID NO:16: P6 derivative peptide (Peptide H)
SEQ ID NO:17: P6 derivative peptide (Peptide I)
SEQ ID NO:18: P6 derivative peptide (Peptide J)
SEQ ID NO:19: P6 derivative peptide (Peptide K)
SEQ ID NO:20: P6 derivative peptide (Peptide L)
SEQ ID NO:21: P6 derivative peptide (Peptide M)
SEQ ID NO:22: P6 derivative peptide (Peptide N)
SEQ ID NO:23: P6 derivative peptide (Peptide O)
SEQ ID NO:24: P6 derivative peptide (Peptide P)
SEQ ID NO:25: P6 derivative peptide (Peptide Q)
SEQ ID NO:26: P6 derivative peptide (Peptide R)
SEQ ID NO:27: P6 derivative peptide (Peptide S)
SEQ ID NO:28: P6 derivative peptide (Peptide T)
SEQ ID NO:29: P6 derivative peptide (Peptide U)
SEQ ID NO:30: P+1N/−1C
SEQ ID NO:31: P+2N/−2C
SEQ ID NO:32: ProTα7

The invention claimed is:

1. A peptide consisting of SEQ ID NO:2 or a peptide salt thereof.

2. The therapeutic agent for a disease associated with blood-brain barrier dysfunction, which contains the peptide or a salt thereof according to claim 1 as the active ingredient,
wherein the disease associated with blood-brain barrier dysfunction is infarction resulting from thrombosis.

3. A therapeutic agent for cerebral infarction, wherein the therapeutic agent comprises the peptide or a salt thereof according to claim 1.

4. A therapeutic agent for cerebral infarction, wherein the therapeutic agent comprises tissue plasminogen activator (tPA), and wherein the therapeutic agent further comprises the peptide or a salt thereof according to claim 1.

5. A method for treating cerebral infarction, the method comprising the step of administering the peptide or a salt thereof according to claim 1 and tissue plasminogen activator (tPA), to a human patient who suffers from cerebral infarction.

6. A method for treating cerebral infarction, the method comprising the step of administering the peptide or a salt thereof according to claim 1 to a human patient who suffers from cerebral infarction.

* * * * *